United States Patent
Parry et al.

(10) Patent No.: US 10,829,529 B2
(45) Date of Patent: Nov. 10, 2020

(54) COMPOSITIONS AND METHODS FOR DELIVERING CFTR POLYPEPTIDES

(71) Applicant: Krystal Biotech, Inc., Pittsburgh, PA (US)

(72) Inventors: Trevor Parry, San Diego, CA (US); Suma Krishnan, San Francisco, CA (US); Pooja Agarwal, Mars, PA (US)

(73) Assignee: KRYSTAL BIOTECH, INC., Pittsburgh, PA (US)

( * ) Notice: Subject to any disclaimer, the term of this patent is extended or adjusted under 35 U.S.C. 154(b) by 0 days.

(21) Appl. No.: 16/784,599

(22) Filed: Feb. 7, 2020

(65) Prior Publication Data

US 2020/0254060 A1   Aug. 13, 2020

Related U.S. Application Data

(60) Provisional application No. 62/802,871, filed on Feb. 8, 2019.

(51) Int. Cl.

| | | |
|---|---|---|
| *A61K 38/17* | (2006.01) | |
| *A61K 48/00* | (2006.01) | |
| *A61P 11/00* | (2006.01) | |
| *C07K 14/47* | (2006.01) | |
| *C12N 15/63* | (2006.01) | |
| *C12N 15/86* | (2006.01) | |
| *A61K 9/00* | (2006.01) | |

(52) U.S. Cl.
CPC ........ *C07K 14/4712* (2013.01); *A61K 9/0073* (2013.01); *A61K 38/1709* (2013.01); *A61K 48/0075* (2013.01); *A61P 11/00* (2018.01); *C12N 15/86* (2013.01); *A61K 9/0075* (2013.01); *A61K 9/0078* (2013.01); *C12N 2710/16011* (2013.01); *C12N 2710/16041* (2013.01); *C12N 2710/16043* (2013.01); *C12N 2710/16071* (2013.01); *C12N 2710/16111* (2013.01); *C12N 2710/16511* (2013.01); *C12N 2710/16611* (2013.01); *C12N 2710/16621* (2013.01); *C12N 2710/16632* (2013.01); *C12N 2710/16643* (2013.01); *C12N 2710/16671* (2013.01); *C12N 2710/16711* (2013.01)

(58) Field of Classification Search
CPC ...... A61K 38/17; A61K 48/00; A61K 48/005; A61K 48/0075; A61K 9/073; A61K 9/0075; A61K 9/0078; A61P 11/00; C07K 14/47; C07K 14/4712; C12N 15/63; C12N 15/86; C12N 15/869; C12N 2710/16011; C12N 2710/16041; C12N 2710/16043; C12N 2710/16071; C12N 2710/16511; C12N 2710/16611; C12N 2710/16711

See application file for complete search history.

(56) References Cited

U.S. PATENT DOCUMENTS

| | | |
|---|---|---|
| 5,658,724 A | 8/1997 | Deluca |
| 5,998,174 A | 12/1999 | Glorioso |
| 6,106,826 A | 8/2000 | Brandt |
| 6,719,982 B1 | 4/2004 | Coffin |
| 6,846,670 B2 | 1/2005 | Schwartz |
| 6,887,490 B1 | 5/2005 | Jahoda |
| 7,731,952 B2 * | 6/2010 | Mohr ................ A61P 37/00 424/93.2 |
| 9,314,505 B2 | 4/2016 | Wise |
| 9,713,626 B2 * | 7/2017 | Heartlein ........... A61K 48/005 |
| 9,840,709 B2 | 12/2017 | Hastings |
| 9,877,990 B2 | 1/2018 | Krishnan |
| 10,155,016 B2 | 12/2018 | Krishnan |
| 10,441,614 B2 | 10/2019 | Krishnan |
| 10,525,090 B2 | 1/2020 | Krishnan |
| 2003/0082142 A1 | 5/2003 | Coffin |
| 2008/0226601 A1 * | 9/2008 | Federoff ............. C12N 15/86 424/93.2 |
| 2008/0299182 A1 | 12/2008 | Zhang |
| 2013/0331547 A1 | 12/2013 | Hall |
| 2014/0256798 A1 | 9/2014 | Osborn |
| 2014/0288155 A1 | 9/2014 | Hovnanian |
| 2014/0341877 A1 | 11/2014 | Kolattukudy |
| 2015/0352191 A1 | 12/2015 | South |
| 2016/0153000 A1 * | 6/2016 | Glorioso ............. A61P 21/04 514/44 R |
| 2017/0290866 A1 * | 10/2017 | Krishnan ............ A61K 35/763 |

(Continued)

FOREIGN PATENT DOCUMENTS

| | | |
|---|---|---|
| CN | 102212559 B | 4/2014 |
| WO | WO 1998/027216 | 6/1998 |

(Continued)

OTHER PUBLICATIONS

Brooks et al, Surgery 129: 324-334, 2001.*

(Continued)

*Primary Examiner* — Kevin K Hill

(74) *Attorney, Agent, or Firm* — Morrison & Foerster LLP

(57) ABSTRACT

The present disclosure provides recombinant nucleic acids comprising one or more polynucleotides encoding a cystic fibrosis transmembrane conductance regulator (CFTR) polypeptide (e.g., a human CFTR polypeptide); viruses comprising the recombinant nucleic acids; compositions and formulations comprising the recombinant nucleic acids and/or viruses; methods of their use (e.g., for the treatment of a chronic lung disease, such as cystic fibrosis); and articles of manufacture or kits thereof.

18 Claims, 19 Drawing Sheets
(12 of 19 Drawing Sheet(s) Filed in Color)
Specification includes a Sequence Listing.

(56) References Cited

U.S. PATENT DOCUMENTS

| | | | |
|---|---|---|---|
| 2019/0160122 A1 | 5/2019 | Krishnan | |
| 2019/0328644 A1 | 10/2019 | Krishnan | |
| 2020/0093874 A1 | 3/2020 | Agarwal | |
| 2020/0101123 A1 | 4/2020 | Krishnan et al. | |

FOREIGN PATENT DOCUMENTS

| | | | |
|---|---|---|---|
| WO | WO9964094 A1 | 12/1999 | |
| WO | WO0040734 A1 | 7/2000 | |
| WO | WO2013121202 A1 | 8/2013 | |
| WO | WO2015009952 A1 | 1/2015 | |
| WO | WO2015117021 A1 | 8/2015 | |
| WO | WO2017165813 A1 | 9/2017 | |
| WO | WO 2017/176336 | 10/2017 | |
| WO | WO2017187321 A1 | 11/2017 | |
| WO | WO2017201347 A1 | 11/2017 | |
| WO | WO2019200163 A1 | 10/2019 | |
| WO | WO2019210219 A1 | 10/2019 | |
| WO | WO2020006486 A1 | 1/2020 | |

OTHER PUBLICATIONS

Benda, J. Hyg. Epidemiol. Microbiol. Immunol. 10(1):105-108, 1966.*
Aldawsari et al., "Progress in Topical siRNA Delivery Approaches for Skin Disorders," Curr Pharm Des. (2015) 21(31): 4594-4605.
Alton et al., "A Phase I/IIa Safety and Efficacy Study of Nebulized Liposome-mediated Gene Therapy for Cystic Fibrosis Supports a Multidose Trial," Am J Respir Crit Care Med (2015) 192(11): 1389-1392.
Alton et al., "Preparation for a First-In-Man Lentivirus Trial in Patients With Cystic Fibrosis," Thorax (2017) 72(2): 137-147.
Alton et al., "Repeated nebulisation of non-viral CFTR gene therapy in patients with cystic fibrosis: a randomised, double-blind, placebo-controlled, phase 2b trial," Lancet Respir Med (2015) 3(9): 684-691.
Andtbacka et. al., "Talimogene Laherparepvec Improves Durable Response Rate in Patients With Advanced Melanoma," J Clin Oncol. (2015) 33(25): 2780-2788.
Armstrong, M. "Krystal gets a flying start in epidermolysis bullosa gene therapy" Vantage. Oct. 17, 2018.
Armstrong, M. "Krystal gets more skin in the epidermolysis bullosa game." Vantage. Mar. 5, 2019.
Bastian et al., "Herpes simplex virus type 1 immediate-early protein ICP22 is required for VICE domain formation during productive viral infection." J Viral. Mar. 2010;84(5):2384-94. doi: 10.1128/JVI.01686-09. Epub Dec. 23, 2009.
Berkers et al., "Rectal Organoids Enable Personalized Treatment of Cystic Fibrosis," Cell Rep (2019) 26(7): 1701-1708.e3.
Birket et al., "Development of an airway mucus defect in the cystic fibrosis rat," JCI Insight (2018) 3(1): e97199.
Boj et al., "Forskolin-induced Swelling in Intestinal Organoids: An In Vitro Assay for Assessing Drug Response in Cystic Fibrosis Patients," J Vis Exp (2017) 120: e55159 (12 pages).
Burton et al., "Gene delivery using herpes simplex virus vectors." DNA Cell Biol. (2002) 21(12): 915-936.
Chamorro et al., "Gene Editing for the Efficient Correction of a Recurrent COL7A1 Mutation in Recessive Dystrophic Epidermolysis Bullosa Keratinocytes", Molecular Therapy—Nucleic Acids, vol. 5, 2016, pp. 1-13.
Christiano AM. Collagen, type VII, alpha 1 (epidermolysis bullosa, dystrophic, dominant and recessive) [*Homo sapiens*]. NCBI Reference Sequence: NP_000085.1. Dep. Mar. 19, 1999.
Clancy et al., "CFTR Modulator Theratyping: Current Status, Gaps and Future Directions," J Cyst Fibros (2019) 18 (1): 22-34.
Clancy et al., "Personalized Medicine in Cystic Fibrosis: Dawning of a New Era," Am J Respir Crit Care Med (2012) 186(7): 593-597.
Clinicaltrials.gov. NCT03536143: Topical Bercolagene Telserpavec (KB103) Gene Therapy to Restore Functional Collagen VII for the Treatment of Dystrophic Epidermolysis Bullosa (GEM-1). May 24, 2018.

Clinicaltrials.gov. NCT04047732: Topical KB105 Gene Therapy for the Treatment of TGM1-deficient Autosonnal Recessive Congenital Ichthyosis (ARCI). Aug. 7, 2019.
Clinicaltrials.gov. NCT04214002: The Natural History of Wounds in Patients with Dystrophic Epidermolysis Bullosa (DEB). Dec. 30, 2019.
Collawn et al., "CFTR and Lung Homeostasis," Am J Physiol Lung Cell Mol Physiol (2014) 307(12): L917-923.
Communication pursuant to Article 94(3) EPC for EP 16826873.8, dated Apr. 17, 2019, 7 pages.
Cooney et al., "Cystic Fibrosis Gene Therapy: Looking Back, Looking Forward," Genes (Basel) (2018) 9(11): 538.
Cutting, G. "Cystic Fibrosis Genetics: From Molecular Understanding to Clinical Application," Nat Rev Genet (2015) 16(1): 45-56.
Dekkers et al., "A Functional CFTR Assay Using Primary Cystic Fibrosis Intestinal Organoids," Nat Med (2013) 19 (7): 939-945.
Deluca et al., "Isolation and Characterization of Deletion Mutants of Herpes Simplex Virus Type 1 in the Gene Encoding Immediate-Early Regulatory Protein ICP4", Journal of Virology, (1985) 56(2): 558-570.
Derichs et al., "Hyperviscous Airway Periciliary and Mucous Liquid Layers in Cystic Fibrosis Measured by Confocal Fluorescence Photobleaching," FASEB J (2011) 25(7): 2325-2332.
Eming et al. "Gene therapy and wound healing," Clin Dermatol. (2007) 25(1): 79-92.
Estrada-Veras et al., "Palliative Care for Patients With Cystic Fibrosis #265," J Palliat Med (2013) 16(4): 446-447.
Examination Report No. 1 received for Australian Patent Application No. 2016401692, , dated Jul. 12, 2019, 4 pages.
Final Office Action received for U.S. Appl. No. 15/393,151, dated Aug. 31, 2017, 13 pages.
Georgiadis et al., "Lentiviral Engineered Fibroblasts Expressing Codon-Optimized COL7A1 Restore Anchoring Fibrils in RDEB", Journal of Investigative Dermatology, (2016) 136: 284-292.
Gill et al., "Delivery of Genes Into the CF Airway," Thorax (2014) 69(10): 962-964.
Glorioso JC. "Herpes simplex viral vectors: late bloomers with big potential." Hum Gene Ther. (2014) 25(2): 83-91.
Goins et al. "Engineering HSV-1 Vectors for Gene Therapy," Methods Mol Biol (2014) 1144: 63-79.
Goto et al., "Fibroblasts Show More Potential as Target Cells than Keratinocytes in COL7A1 Gene Therapy of Dystrophic Epidermolysis Bullosa", Journal of Investigative Dermatology, (2006) 126: 766-772.
Grant, Kyle, "Production and Purification of Highly Replication Defective Hsv-1 Based Gene Therapy Vectors", Doctoral Dissertation, University of Pittsburgh, 2008, 137 pages.
Gurevich et. al. 759 "Successful in vivo COL7A1 gene delivery and correction of recessive dystrophic epidermolysis bullosa (RDEB) skin using an off the shelf HSV-1 vector (KB103)." J Invest Derm. vol. 138, Iss. 5 Supp. May 2018, p. S129. Available online Apr. 19, 2018.
Heikkinen et al., "Diremerization of human lysyl hydroxylase 3 (LH3) is mediated by the amino acids 541 547," Matrix Biology (2010) 30(1):27-33.
Hennig et al., "HEK293-based production platform for y-retroviral (self-inactivating) vectors: application for safe and efficient transfer of COL7A1 cDNA". Hum Gene Ther Clin Dev. (2014) 25(4): 218-228.
Hyde et al., "Repeat Administration of DNA/liposomes to the Nasal Epithelium of Patients With Cystic Fibrosis," Gene Ther (2000) 7(13): 1156-1165.
International Preliminary Report on Patentability received for PCT Patent Application No. PCT/US2016/068974, dated Oct. 18, 2018, 11 pages.
International Search Report and Written Opinion received for PCT Patent Application No. PCT/US2016/068974, dated May 18, 2017, 18 pages.
Invitation to Pay Additional Fee received for PCT Patent Application No. PCT/US2016/068974, dated Mar. 27, 2017, 8 pages.
Kerem et al., "Identification of the Cystic Fibrosis Gene: Genetic Analysis," Science (1989) 245(4922): 1073-1080.

(56) References Cited

OTHER PUBLICATIONS

Kim et al., "Barriers to Inhaled Gene Therapy of Obstructive Lung Diseases: A Review," J Control Release (2016) 240: 465-488.
Kim et al., "Microneedles for Drug and Vaccine Delivery", Advanced Drug Delivery Reviews, vol. 64, 2012, pp. 1547-1568.
Knowles et al., "A Controlled Study of Adenoviral-Vector-Mediated Gene Transfer in the Nasal Epithelium of Patients With Cystic Fibrosis," N Engl J Med (1995) 333(13): 823-831.
Kopecki et al., "Commentary: New advances in the development of therapies for treating inherited skin fragility disorders," Wound Practice and Research (2015) 23(4): 184.
Lachmann, R. "Herpes simplex virus-based vectors," Int J Exp Pathol. (2004) 85(4): 177-190.
Lewin et al., "Gene therapy for autosomal dominant disorders of keratin," J Investig Dermatol Symp Proc. (2005) 10 (1): 47-61.
Liou et al., "Year-to-year Changes in Lung Function in Individuals With Cystic Fibrosis," J Cyst Fibros (2010) 9(4): 250-256.
Lommatzsch et al., "The Combination of Tezacaftor and Ivacaftor in the Treatment of Patients With Cystic Fibrosis: Clinical Evidence and Future Prospects in Cystic Fibrosis Therapy," Ther Adv Respir Dis (2019) 13: 1-13. https://doi.org/10.1177/1753466619844424.
Lu et al., "Topical Application of Viral Vectors for Epidermal Gene Transfer", J Invest Dermatol. (1997) 108(5): 803-808.
Maiuri et al., "The Holy Grail of Cystic Fibrosis Research: Pharmacological Repair of the F508del-CFTR Mutation," Ann Transl Med (2015) 3 (Suppl 1), S24.
Mall et al., "CFTR: Cystic Fibrosis and Beyond," Eur Respir J (2014) 44(4): 1042-1054.
Marconi et al., "HSV as a Vector in Vaccine Development and Gene Therapy." In: Madame Curie Bioscience Database [Internet]. Austin (TX): Landes Bioscience; 2000-2013. 30 pages.
Mayr et al., "Gene Therapy for the COL7A1 Gene", Chapter 23, Intech, 2013, pp. 561-589.
McLachlan et al., "Pre-clinical Evaluation of Three Non-Viral Gene Transfer Agents for Cystic Fibrosis After Aerosol Delivery to the Ovine Lung," Gene Ther (2011) 18(10): 996-1005.
Mitomo et al., "Toward Gene Therapy for Cystic Fibrosis Using a Lentivirus Pseudotyped With Sendai Virus Envelopes," Mol Ther (2010) 18(6): 1173-1182.
Moss et al., "Repeated Adeno-Associated Virus Serotype 2 Aerosol-Mediated Cystic Fibrosis Transmembrane Regulator Gene Transfer to the Lungs of Patients With Cystic Fibrosis: A Multicenter, Double-Blind, Placebo-Controlled Trial," Chest (2004) 125 (2): 509-521.
Moss et al., "Repeated Aerosolized AAV-CFTR for Treatment of Cystic Fibrosis: A Randomized Placebo-Controlled Phase 2B Trial," Hum Gene Ther (2007) 18(8): 726-732.
Neuberger et al., "Use of Primary Cultures of Human Bronchial Epithelial Cells Isolated From Cystic Fibrosis Patients for the Pre-Clinical Testing of CFTR Modulators," Methods Mol Biol (2011) 741: 39-54.
NG et al., "Fibroblast-Derived Dermal Matrix Drives Development of Aggressive Cutaneous Squamous Cell Carcinoma in Patients with Recessive Dystrophic Epidermolysis Bullosa", Cancer Research, (2012) 72(14): 3522-3534.
Non-Final Office Action received for U.S. Appl. No. 15/393,151, dated Apr. 14, 2017, 13 pages.
Non-Final Office Action received for U.S. Appl. No. 15/851,488, dated May 14, 2018, 10 pages.
Non-Final Office Action received for U.S. Appl. No. 16/177,153, dated May 9, 2019, 13 pages.
Notice of Allowance received for U.S. Appl. No. 15/393,151, dated Dec. 6, 2017, 11 pages.
Notice of Allowance received for U.S. Appl. No. 15/851,488, dated Oct. 29, 2018, 11 pages.
Notice of Allowance received for U.S. Appl. No. 16/177,153, dated Aug. 30, 2019, 10 pages.
Ortiz-Urda et al., "Injection of Genetically Engineered Fibroblasts Corrects Regenerated Human Epidermolysis Bullosa Skin Tissue", The Journal of Clinical Investigation,(2003) 111(2): 251-255.
Pacheco, M., "CFTR Modulators: Shedding Light on Precision Medicine for Cystic Fibrosis," Front Pharmacol (2016) 7: 275 (20 pages).
Patil et al., "Pulmonary Drug Delivery Strategies: A Concise, Systematic Review," Lung India (2012) 29(1): 44-49.
Pezzulo et al., Reduced Airway Surface pH Impairs Bacterial Killing in the Porcine Cystic Fibrosis Lung, Nature (2012) 487(7405): 109-113.
Pilewski et al., "Role of CFTR in Airway Disease," Physiol Rev (1999) 79 (1 Suppl): S215-255.
Quinton, P. "Physiological Basis of Cystic Fibrosis: A Historical Perspective," Physiol Rev (1999) 79 (1 Suppl): S3-S22.
Randell et al., "Primary Epithelial Cell Models for Cystic Fibrosis Research," Methods Mol Biol (2011) 742: 285-310.
Salam A. "Krystal's KB103 splits experts' thoughts on potential for HSV-1 risk in dystrophic epidermolysis bullosa patients, but final Phase I/II efficacy assured." Nov. 7, 2018. Biopharm Insight.
Salmon-Ehr et al., "Implication of Interleukin-4 in Wound Healing", Laboratory Investigation, (2000) 80,(8): 1337-1343.
Samaniego et al., "Persistence and Expression of the Herpes Simplex Virus Genome in the Absence of Immediate-Early Proteins", Journal of Virology, (1998) 72(4): 3307-3320.
Sankar et al., "A novel role for keratin 17 in coordinating oncogenic transformation and cellular adhersion in eqing sarcoma," Molecular and Cellular Biology (2013) 33(22):4448-4460.
Scanlin et al., "Glycosylation and the Cystic Fibrosis Transmembrane Conductance Regulator," Respir Res (2001) 2 (5): 276-279.
Shen et al., "Herpes simplex virus 1 (HSV-1) for cancer treatment," Cancer Gene Therapy (2006) 13: 975-992.
Silva et al., "Herpes Virus Amplicon Vectors", Viruses, (2000) vol. 1, pp. 594-629.
Siprashvili et al., "Long-term type VII collagen restoration to human epidermolysis bullosa skin tissue," Hum Gene Ther. (2010) 21(10): 1299-1310.
Steines et al., "CFTR Gene Transfer With AAV Improves Early Cystic Fibrosis Pig Phenotypes," JCI Insight (2016) 1 (14): e88728.
Stoltz et al., "Origins of Cystic Fibrosis Lung Disease," N Engl J Med (2015) 372(4): 351-362.
Stow et al., Isolation and characterization of a herpes simplex virus type 1 mutant containing a deletion within the gene encoding the immediate early polypeptide Vmw110. J Gen Viral. Dec. 1986;67 (Pt 12): 2571-85.
Strong et al., "Current Approaches to the Discovery of Novel Inhaled Medicines," Drug Discov Today (2018) 23(10): 1705-1717.
Suk et al., "N-acetylcysteine Enhances Cystic Fibrosis Sputum Penetration and Airway Gene Transfer by Highly Compacted DNA Nanoparticles," Mol Ther (2011) 19(11): 1981-1989.
Tarran et al., "The CF Salt Controversy: In Vivo Observations and Therapeutic Approaches," Mol Cell (2001) 8(1): 149-158.
Toietta et al., "Reduced Inflammation and Improved Airway Expression Using Helper-Dependent Adenoviral Vectors With a K18 Promoter," Mol Ther (2003) 7(5 Pt 1), 649-658.
Tuggle et al., "Characterization of Defects in Ion Transport and Tissue Development in Cystic Fibrosis Transmembrane Conductance Regulator (CFTR)-knockout Rats," PLoS One (2014) 9(3): e91253.
Unpublished U.S. Appl. No. 16/598,982, filed Oct. 10, 2019, by Suma et al. titled "Compositions and Methods for the Treatment of Wounds, Disorders, and Diseases of the Skin" (Copy not provided)(Copy not submitted herewith pursuant to the waiver of 37 C.F. R. § 1.98(a)(2)(iii) issued by the Office on Sep. 21, 2004).
Uitto et al., "Progress toward Treatment and Cure of Epidermolysis Bullosa: Summary of the DEBRA International Research Symposium EB2015", Journal of Investigative Dermatology, (2016) 136: 352-358.
Unpublished U.S. Appl. No. 16/734,156, filed Jan. 3, 2020, titled "Compositions and Methods for the Treatment of Autosomal Recessive Congenital Ichthyosis" by Krishnan. (Copy not provided). (Copy not submitted herewith pursuant to the waiver of 37 C.F. R. § 1.98(a)(2)(iii) issued by the Office on Sep. 21, 2004).
Veit et al., "From CFTR Biology Toward Combinatorial Pharmacotherapy: Expanded Classification of Cystic Fibrosis Mutations," Mol Biol Cell (2016) 27(3): 424-433.

(56) References Cited

OTHER PUBLICATIONS

Vidovic et al., "rAAV-CFTRΔR Rescues the Cystic Fibrosis Phenotype in Human Intestinal Organoids and Cystic Fibrosis Mice," Am J Respir Crit Care Med (2016) 193(3): 288-298.

Walters et al., "Basolateral Localization of Fiber Receptors Limits Adenovirus Infection From the Apical Surface of Airway Epithelia," J Biol Chem (1999) 274(15): 10219-10226.

Wang et al., "Comparative Effectiveness of Antinociceptive Gene Therapies in Animal Models of Diabetic Neuropathic Pain", Gene Therapy, (2013) 20: 742-750.

Watanabe et al., "Properties of a Herpes Simplex Virus Multiple Immediate-early Gene-Deleted Recombinant as a Vaccine Vector", Virology, vol. (2007) 357: 186-198.

Watt et al., "Lysyl Hydroxylase 3 Localizes to Epidermal Basement Membrane and is Reduced in Patients with Recessive Dystrophic Epidermolysis Bullosa", Plos One, (2015) 10(9): e0137639.

Weiss et al., "The Role of Interleukin 10 in the Pathogenesis and Potential Treatment of Skin Diseases", Journal of the American Academy of Dermatology, (2004) 50(5): 657-675.

Wersto et al., "Uptake of Fluorescent Dyes Associated With the Functional Expression of the Cystic Fibrosis Transmembrane Conductance Regulator in Epithelial Cells," Proc Natl Acad Sci U S A (1996) 93(3): 1167-1172.

White et al., "Evaluation and optimization of the administration of a selectively replicating herpes simplex viral vector to the brain by convection-enhanced delivery," Cancer Gene Ther. (2011) 18(5): 358-69. doi: 10.1038/ cgt.2011.2. Epub Mar. 4, 2011.

Wilschanski, M., "Class 1 CF Mutations," Front in Pharm (2012) 3:117 (3pgs).

Wolfe et al., "Engineering Herpes Simplex Viral Vectors for Therapeutic Gene Transfer", Gene and Cell Therapy, (2004) Chapter 6, pp. 103-129.

Woodley et al., "Normal and Gene-Corrected Dystrophic Epidermolysis Bullosa Fibroblasts Alone Can Produce Type VII Collagen at the Basement Membrane Zone", The Journal of Investigative Dermatology, (2003) 121(5): 1021-1028.

Woodley, et al., "Intradermal Injection of Lentiviral Vectors Corrects Regenerated Human Dystrophic Epidermolysis Bullosa Skin Tissue in Vivo", Molecular Therapy, (2004) 10(2): 318-326.

Zhou et al., "Correction of Lethal Intestinal Defect in a Mouse Model of Cystic Fibrosis by Human CFTR," Science (1994) 266(5191): 1705-1708.

Zuckerman, J. "Safety and Tolerability of a Single Dose of MRT5005, a Nebulized CFTR mRNA Therapeutic, in Adult CF Patients," 33rd Annual North American Cystic Fibrosis Conference (NACFC) Nashville, TN; Oct. 31-Nov. 2, 2019, Presentation, Abs 515.

International Search Report and Written Opinion for PCT/US2020/017191, dated May 13, 2020, 16 pages.

Simoons-Smit et al., "Herpes simplex virus type 1 and respiratory disease in critically-ill patients: real pathogen or innocent bystander?" Clin Microbiol Infect (2006) 12:1050-1059.

Theopold et al., "A novel replication-defective HSV-1 vector for regulatable gene delivery to wounds," Journal of the American College of Surgeons (2004) 199(3):57-58.

Zielenski et al., "Genomic DNA sequence of the cystic gibrosis transmembrane conductance regulator (CFTR) gene," Genomics (1991) 10(1):214-228.

\* cited by examiner

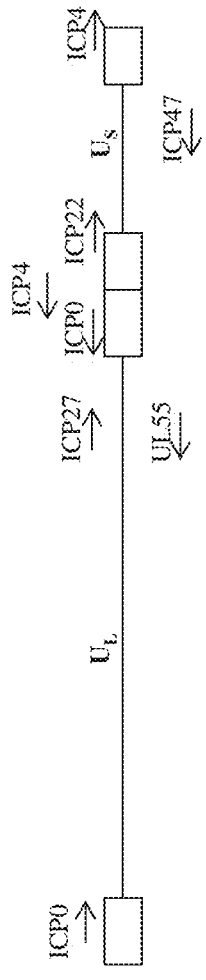
FIG. 1A
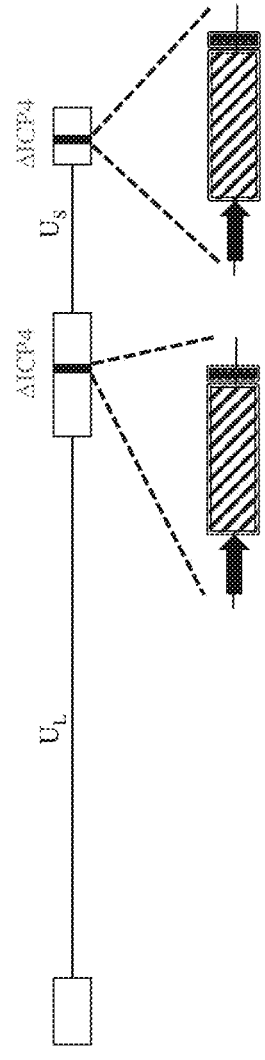
FIG. 1B
 = heterologous promoter
 = coding sequence of human cystic fibrosis transmembrane conductance regulator (CFTR) polypeptide
= regulatory elements

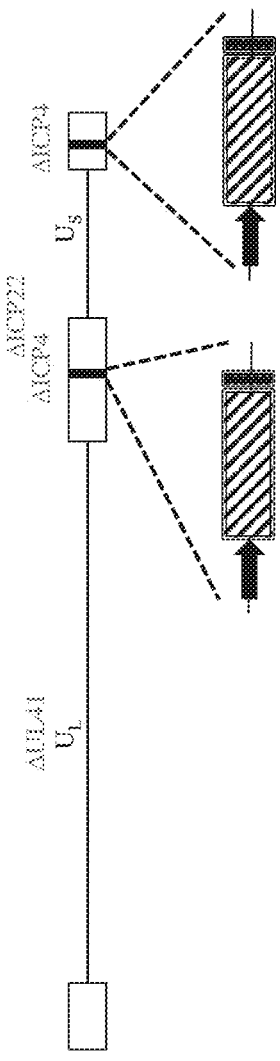
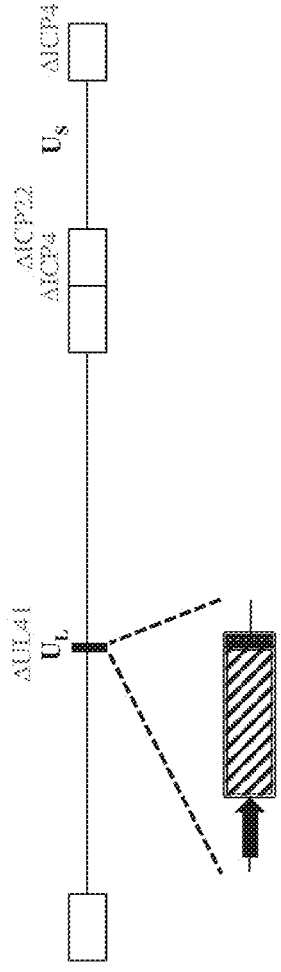
FIG. 1G
FIG. 1H

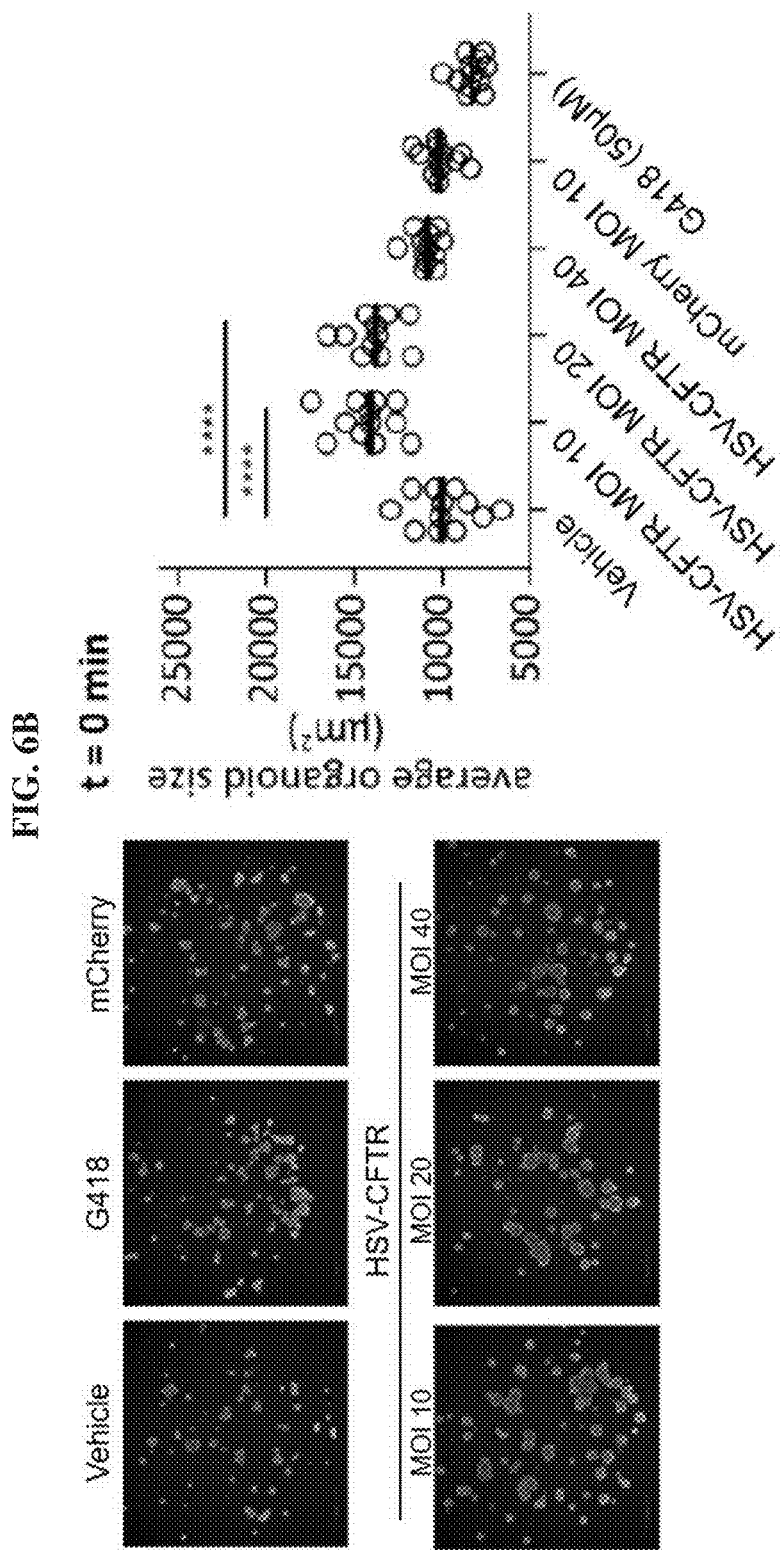

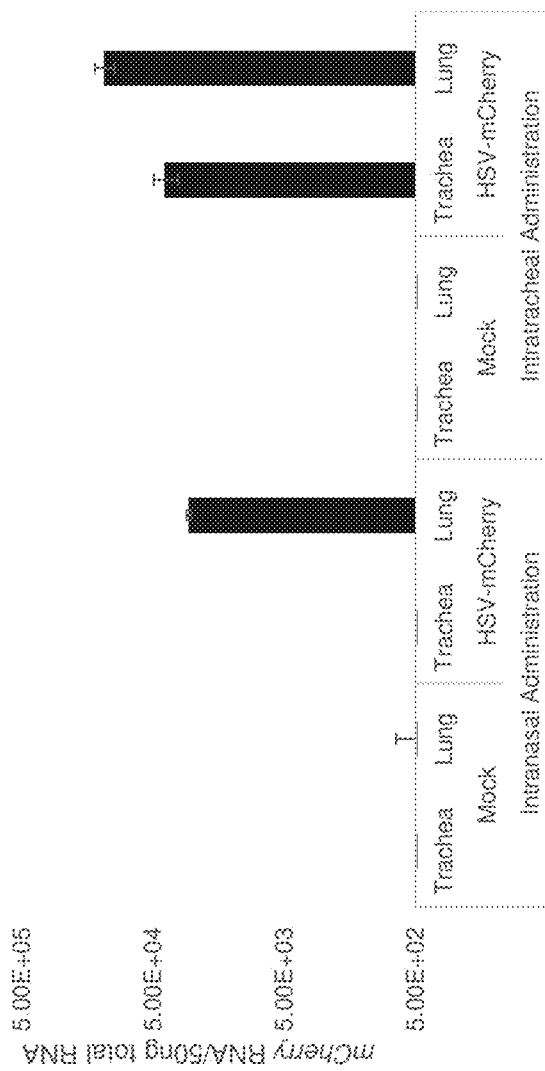

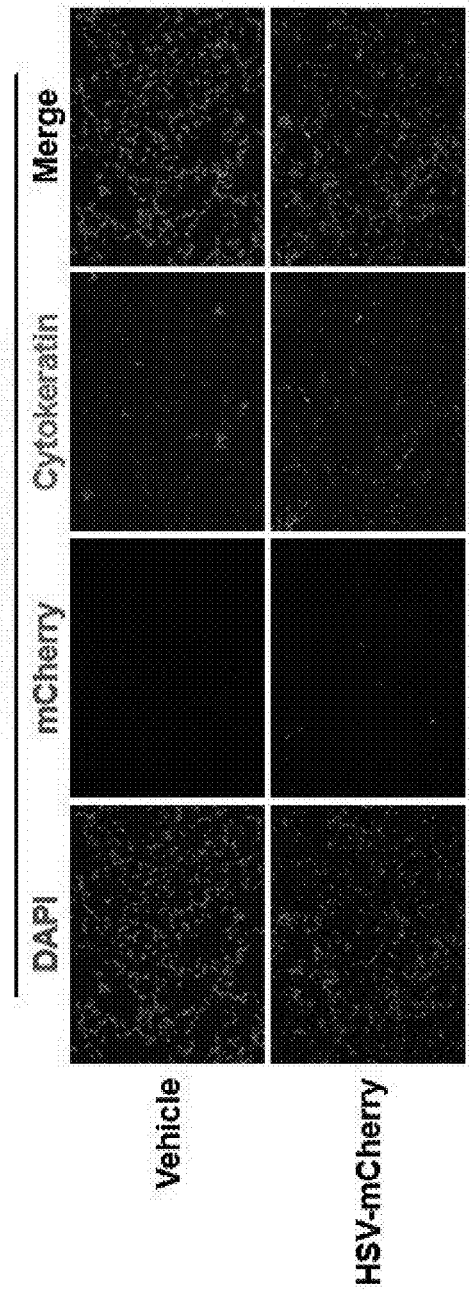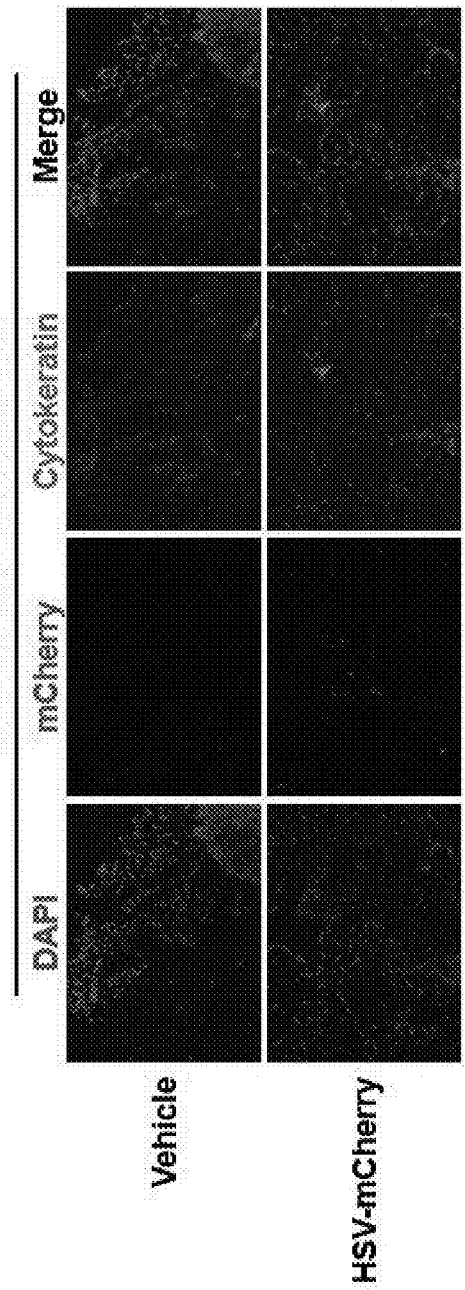

SEQUENCE LISTING

<160> NUMBER OF SEQ ID NOS: 6

<210> SEQ ID NO 1
<211> LENGTH: 4443
<212> TYPE: DNA
<213> ORGANISM: Homo sapiens

<400> SEQUENCE: 1

```
atgcagaggt cgcctctgga aaaggccagc gttgtctcca aactttttt cagctggacc      60 agaccaattt tgaggaaagg atacagacag cgcctggaat tgtcagacat ataccaaatc     120
ccttctgttg attctgctga caatctatct gaaaaattgg aaagagaatg ggatagagag     180
ctggcttcaa agaaaaatcc taaactcatt aatgcccttc ggcgatgttt ttctggaga      240 tttatgttct atggaatctt tttatattta ggggaagtca ccaaagcagt acagcctctc     300
ttactgggaa gaatcatagc ttcctatgac ccggataaca aggaggaacg ctctatcgcg     360
atttatctag gcataggctt atgccttctc tttattgtga ggacactgct cctacaccca     420
```

```
gccattttg   gccttcatca   cattggaatg   cagatgagaa   tagctatgtt   tagtttgatt      480
tataagaaga  ctttaaagct   gtcaagccgt   gttctagata   aaataagtat   tggacaactt      540
gttagtctcc  tttccaacaa   cctgaacaaa   tttgatgaag   acttgcatt    ggcacatttc      600 gtgtggatcg  ctcctttgca   agtggcactc   ctcatgggc    taatctggga   gttgttacag      660
gcgtctgcct  tctgtggact   tggtttcctg   atagtccttg   ccctttttca   ggctgggcta      720
gggagaatga  tgatgaagta   cagagatcag   agagctggga   agatcagtga   aagacttgtg      780
attacctcag  aaatgattga   aaatatccaa   tctgttaagg   catactgctg   ggaagaagca      840
atggaaaaaa  tgattgaaaa   cttaagacaa   acagaactga   aactgactcg   gaaggcagcc      900
tatgtgagat  acttcaatag   ctcagccttc   ttcttctcag   ggttctttgt   ggtgttttta      960
tctgtgcttc  cctatgcact   aatcaaagga   atcatcctcc   ggaaaatatt   caccaccatc     1020
tcattctgca  ttgttctgcg   catggcggtc   actcggcaat   tccctgggc    tgtacaaaca     1080 tggtatgact  ctcttggagc   aataaacaaa   atacaggatt   tcttacaaaa   gcaagaatat     1140
aagacattgg  aatataactt   aacgactaca   gaagtagtga   tggagaatgt   aacagccttc     1200
tgggaggagg  gatttgggga   attatttgag   aaagcaaaac   aaaacaataa   caatagaaaa     1260
acttctaatg  gtgatgacag   cctcttcttc   agtaatttct   cacttcttgg   tactcctgtc     1320
ctgaaagata  ttaatttcaa   gatagaaaga   ggacagttgt   tggcggttgc   tggatccact     1380
ggagcaggca  agacttcact   tctaatggtg   attatgggag   aactggagcc   ttcagagggt     1440
aaaattaagc  acagtggaag   aatttcattc   tgttctcagt   tttcctggat   tatgcctggc     1500
accattaaag  aaaatatcat   ctttggtgtt   tcctatgatg   aatatagata   cagaagcgtc     1560
atcaaagcat  gccaactaga   agaggacatc   tccaagtttg   cagagaaaga   caatatagtt     1620
cttggagaag  gtggaatcac   actgagtgga   ggtcaacgag   caagaatttc   tttagcaaga     1680
gcagtataca  aagatgctga   tttgtattta   ttagactctc   cttttggata   cctagatgtt     1740
ttaacagaaa  aagaaatatt   tgaaagctgt   gtctgtaaac   tgatggctaa   caaaactagg     1800
attttggtca  cttctaaaat   ggaacattta   agaaagctg    acaaaatatt   aattttgcat     1860
gaaggtagca  gctatttta    tgggacattt   tcagaactcc   aaaatctaca   gccagacttt     1920
agctcaaaac  tcatgggatg   tgattctttc   gaccaattta   gtgcagaaag   aagaaattca     1980
atcctaactg  agaccttaca   ccgtttctca   ttagaaggag   atgctcctgt   ctcctggaca     2040
gaaacaaaaa  aacaatcttt   taaacagact   ggagagtttg   gggaaaaaag   gaagaattct     2100
attctcaatc  caatcaactc   tatacgaaaa   ttttccattg   tgcaaaagac   tcccttacaa     2160
atgaatggca  tcgaagagga   ttctgatgag   cctttagaga   aaggctgtc    cttagtacca     2220 gattctgagc  agggagaggc   gatactgcct   cgcatcagcg   tgatcagcac   tggccccacg     2280
cttcaggcac  gaaggaggca   gtctgtcctg   aacctgatga   cacactcagt   taaccaaggt     2340
cagaacattc  accgaaagac   aacagcatcc   acacgaaaag   tgtcactggc   ccctcaggca     2400
aacttgactg  aactggatat   atattcaaga   aggttatctc   aagaaactgg   cttggaaata     2460
agtgaagaaa  ttaacgaaga   agacttaaag   gagtgctttt   ttgatgatat   ggagagcata     2520
ccagcagtga  ctacatggaa   cacataccct   cgatatatta   ctgtccacaa   gagcttaatt     2580
tttgtgctaa  tttggtgctt   agtaattttt   ctggcagagg   tggctgcttc   tttggttgtg     2640
ctgtggctcc  ttgaaacac    tcctcttcaa   gacaaaggga   atagtactca   tagtagaaat     2700
aacagctatg  cagtgattat   caccagcacc   agttcgtatt   atgtgtttta   catttacgtg     2760
```

| | |
|---|---|
| ggagtagccg acactttgct tgctatggga ttcttcagag gtctaccact ggtgcatact | 2820 |
| ctaatcacag tgtcgaaaat tttacaccac aaaatgttac attctgttct tcaagcacct | 2880 |
| atgtcaaccc tcaacacgtt gaaagcaggt gggattctta atagattctc caaagatata | 2940 |
| gcaattttgg atgaccttct gcctcttacc atatttgact tcatccagtt gttattaatt | 3000 |
| gtgattggag ctatagcagt tgtcgcagtt ttacaaccct acatctttgt tgcaacagtg | 3060 |
| ccagtgatag tggcttttat tatgttgaga gcatatttcc tccaaacctc acagcaactc | 3120 |
| aaacaactgg aatctgaagg caggagtcca attttcactc atcttgttac aagcttaaaa | 3180 |
| ggactatgga cacttcgtgc cttcggacgg cagccttact tgaaactct gttccacaaa | 3240 |
| gctctgaatt tacatactgc caactggttc ttgtacctgt caacactgcg ctggttccaa | 3300 |
| atgagaatag aaatgatttt tgtcatcttc ttcattgctg ttaccttcat ttccattta | 3360 |
| acaacaggag aaggagaagg aagagttggt attatcctga ctttagccat gaatatcatg | 3420 |
| agtacattgc agtgggctgt aaactccagc atagatgtgg atagcttgat gcgatctgtg | 3480 |
| agccgagtct ttaagttcat tgacatgcca acagaaggta aacctaccaa gtcaaccaaa | 3540 |
| ccatacaaga atggccaact ctcgaaagtt atgattattg agaattcaca cgtgaagaaa | 3600 |
| gatgacatct ggccctcagg gggccaaatg actgtcaaag atctcacagc aaaatacaca | 3660 |
| gaaggtggaa atgccatatt agagaacatt tccttctcaa taagtcctgg ccagagggtg | 3720 |
| ggcctcttgg gaagaactgg atcagggaag agtactttgt tatcagcttt tttgagacta | 3780 |
| ctgaacactg aaggagaaat ccagatcgat ggtgtgtctt gggattcaat aactttgcaa | 3840 |
| cagtggagga aagcctttgg agtgatacca cagaaagtat ttatttttc tggaacattt | 3900 |
| agaaaaaact tggatcccta tgaacagtgg agtgatcaag aaatatggaa agttgcagat | 3960 |
| gaggttgggc tcagatctgt gatagaacag tttcctggga agcttgactt tgtccttgtg | 4020 |
| gatgggggct gtgtcctaag ccatggccac aagcagttga tgtgcttggc tagatctgtt | 4080 |
| ctcagtaagg cgaagatctt gctgcttgat gaacccagtg ctcatttgga tccagtaaca | 4140 |
| taccaaataa ttagaagaac tctaaaacaa gcatttgctg attgcacagt aattctctgt | 4200 |
| gaacacagga tagaagcaat gctggaatgc caacaatttt tggtcataga agagaacaaa | 4260 |
| gtgcggcagt acgattccat ccagaaactg ctgaacgaga ggagcctctt ccggcaagcc | 4320 |
| atcagcccct ccgacagggt gaagctcttt ccccaccgga actcaagcaa gtgcaagtct | 4380 |
| aagccccaga ttgctgctct gaaagaggag acagaagaag aggtgcaaga tacaaggctt | 4440 |
| tag | 4443 |

<210> SEQ ID NO 2
<211> LENGTH: 4443
<212> TYPE: DNA
<213> ORGANISM: Artificial Sequence
<220> FEATURE:
<223> OTHER INFORMATION: Synthetic Construct

<400> SEQUENCE: 2

| | |
|---|---|
| atgcagagaa gccctctgga aaaggccagc gtggtgtcca agctgttctt cagctggacc | 60 |
| cggcctatcc tgcggaaggg ctatagacag agactggaac tgagcgacat ctatcagatc | 120 |
| cccagcgtgg acagcgccga caacctgtct gagaagctgg aaagagagtg gacagagag | 180 |
| ctggcctcca agaagaaccc caagctgatc aacgccctgc ggcggtgctt cttctggcgg | 240 |
| tttatgttct acggcatctt cctgtacctg ggcgaagtga ccaaagccgt gcagcctctg | 300 |
| ctgctgggca gaatcattgc cagctacgac cccgacaaca agaggaacg gtctatcgcc | 360 |

```
atctacctcg gcatcggcct gtgcctgctg tttatcgtca gaaccctgct gctgcacccc    420
gccatctttg gactgcacca catcggcatg cagatgcgga tcgccatgtt cagcctgatc    480
tacaagaaaa ccctgaagct gtccagcaga gtgctggaca agatcagcat cggacagctg    540
gtgtccctgc tgagcaacaa cctgaacaag ttcgacgaag gcctggctct ggcccacttc    600
gtgtggattg ctcctctgca agtggccctg ctgatgggcc tgatttggga actgctgcag    660
gccagcgcct tttgcggact gggatttctg attgtgctgg ccctgttcca ggccggactg    720
gggagaatga tgatgaagta ccgggaccag agagccggca agatctccga gagactggtc    780
atcaccagcg agatgatcga gaacatccag agcgtgaagg cctactgctg ggaagaggcc    840
atggaaaaga tgattgagaa tctgcggcag accgagctga agctgacaag aaaggccgcc    900
tacgtgcgct acttcaacag cagcgccttc ttcttctccg gcttcttcgt ggtgttcctg    960
agcgtgctgc cctacgctct gatcaagggc atcatcctga aaagatttt caccaccatt   1020 tctttctgca tcgtgctgcg gatggccgtg accagacagt tccttgggc tgtgcagact   1080 tggtacgata gcctgggcgc catcaacaag atccaggact tcctgcagaa gcaagagtac   1140
aagaccctcg agtacaacct gaccaccacc gaggtggtca tggaaaacgt gaccgccttc   1200
tgggaggaag gcttcggcga gctgtttgag aaggccaagc agaacaacaa caaccgcaag   1260
accagcaacg cgacgacag cctgttcttc tccaacttct ccctgctggg acccctgtg    1320 ctgaaggaca tcaacttcaa gatcgagcgg ggacagctgc tggccgtggc tggatctaca   1380
ggcgccggaa aaaccagcct gctcatggtc atcatgggcg agctggaacc tagcgagggc   1440
aagatcaagc acagcggcag gatcagcttc tgtagccagt tctcctggat catgcccggc   1500
accatcaaag agaacatcat cttcggcgtg tcctacgacg agtacagata ccgcagcgtg   1560
atcaaggcct gccagctgga agaggacatc agcaagttcg ccgagaagga caacatcgtg   1620
ctcggcgaag cggcatcac actgtctggg ggacagaggg ccagaatctc tctggctaga   1680
gccgtgtaca aggacgccga tctgtacctg ctggatagcc ccttcggcta cctggatgtg   1740
ctgaccgaga aagagatctt cgagagctgc gtgtgcaagc tgatggccaa caagaccaga   1800
atcctggtca cctccaagat ggaacacctg aagaaggccg acaagatcct gattctgcac   1860
gagggcagca gctactttta cggcaccttc agcgagctgc agaacctgca gcctgacttc   1920
agcagcaaac tgatgggctg cgactccttc gaccagttca cgccgagcg agaaacagc    1980 atcctgacag agacactgca ccggttctcc ctggaaggcg acgtcctgt gtcttggacc    2040 gagacaaaga agcagagctt caagcagacc ggcgagtttg gcgagaagcg gaagaactcc   2100
attctgaacc ccatcaactc catccggaag ttcagcatcg tccagaaaac ccctctgcag   2160
atgaacggca tcgaagagga tagcgacgag ccctggaaa acggctgtc tctggtgcct    2220 gatagcgaac agggcgaagc catcctgcct cggatctccg tgattagcac aggccctaca   2280
ctgcaggctc ggagaaggca gagtgtgctg aacctgatga cccacagcgt gaaccaggga   2340
cagaatatcc acagaaagac caccgccagc acacggaaag tgtcactggc ccctcaggcc   2400
aacctgactg agctggacat ctacagcaga cggctgagcc aagagacagg cctggaaatc   2460
agcgaggaaa tcaacgaaga ggacctgaaa gagtgctttt tcgacgacat ggaatctatc   2520
cccgccgtga caacctggaa tacctacctg cggtacatca ccgtgcacaa gtccctgatc   2580
ttcgtgctga tctggtgtct cgtgatcttc ctggccgaag tggccgcttc tctggtggtt   2640
ctgtggctgc tcggaaacac cccactgcag gacaagggca atagcaccca cagccggaac   2700
```

| | | |
|---|---|---|
| aacagctacg ccgtgatcat cacctccacc agctcctact acgtgttcta catctacgtg | 2760 | |
| ggcgtcgccg acactctgct cgccatgggc ttttttagag gactgcccct ggtgcacacc | 2820 | |
| ctgatcaccg tgtctaagat cctgcaccat aagatgctgc acagcgtcct gcaggcccct | 2880 | |
| atgagcacac tgaacaccct gaaagccggc ggaatcctga acagattcag caaggacatt | 2940 | |
| gccatcctgg acgacctgct gcctctgacc atcttcgact tcatccagct gctgctgatc | 3000 | |
| gtgatcggcg ccattgctgt ggtggctgtg ctgcagcctt acatcttcgt ggccaccgtg | 3060 | |
| cctgtgatcg tggccttcat tatgctgcgg gcctactttc tgcagacctc tcagcagctg | 3120 | |
| aagcagctcg agtctgaggg cagaagcccc atctttaccc acctcgtgac cagcctgaaa | 3180 | |
| ggcctgtgga ccctgagagc ctttggcaga cagccctact cgagacact gttccacaag | 3240 | |
| gccctgaacc tgcacaccgc caactggttt ctgtatctga gcaccctgcg gtggttccag | 3300 | |
| atgaggatcg agatgatttt cgtcatcttc tttatcgccg tgaccttcat cagcatcctc | 3360 | |
| accactggcg aaggcgaggg cagagtggga atcattctga ccctggccat gaacatcatg | 3420 | |
| tccacactcc agtgggccgt gaacagcagc atcgatgtgg acagcctgat gcggagcgtg | 3480 | |
| tcccgggtgt tcaagttcat cgacatgccc acagagggca agcccaccaa gagcaccaag | 3540 | |
| ccttacaaga acgccagct gagcaaagtc atgatcatcg agaactccca cgtcaagaag | 3600 | |
| gacgacattt ggcccagcgg aggccagatg accgtgaagg atctgaccgc caagtacacc | 3660 | |
| gaaggcggaa acgccattct ggaaaacatc agctttagca tcagccctgg ccagcgcgtg | 3720 | |
| ggactccttg gaagaaccgg aagcggcaag tctactctgc tgagcgcctt cctgagactg | 3780 | |
| ctgaataccg agggcgagat ccagatcgat ggggtgtcct gggacagcat caccctgcaa | 3840 | |
| caatggcgga aggcctttgg cgtgatccct cagaaggtgt tcattttcag cggcacgttc | 3900 | |
| cggaagaatc tggaccccta cgagcagtgg agcgaccaag agatttggaa ggtggccgat | 3960 | |
| gaagtgggac tgagaagcgt gatcgagcag tttcccggca agctggattt cgtgctggtg | 4020 | |
| gatgcgggct gtgtgctgtc tcacggacac aagcagctga tgtgcctggc cagatccgtg | 4080 | |
| ctgtccaagg ccaagattct gctgctcgac gagcctagcg ctcacctcga tcctgtgacc | 4140 | |
| taccagatca tccggcggac actgaagcag gcctttgccg attgcaccgt gatcctgtgc | 4200 | |
| gagcacagaa ttgaggccat gctggaatgc cagcagtttc tggttatcga agagaacaaa | 4260 | |
| gtgcggcagt acgacagcat ccagaagctg ctgaacgagc ggagcctgtt cagacaggcc | 4320 | |
| atctctccca gcgacagagt gaagctgttc cctcaccgga acagctccaa gtgcaagagc | 4380 | |
| aagcctcaga tcgccgctct gaaagaagaa accgaggaag aggtgcagga cacacggctg | 4440 | |
| taa | 4443 | |

```
<210> SEQ ID NO 3
<211> LENGTH: 4260
<212> TYPE: DNA
<213> ORGANISM: Homo sapiens

<400> SEQUENCE: 3
```

| | | |
|---|---|---|
| atgcagaggt cgcctctgga aaaggccagc gttgtctcca aacttttttt cagctggacc | 60 | |
| agaccaattt tgaggaaagg atacagacag cgcctggaat tgtcagacat ataccaaatc | 120 | |
| ccttctgttg attctgctga caatctatct gaaaaattgg aaagagaatg ggatagagag | 180 | |
| ctggcttcaa agaaaaatcc taaactcatt aatgcccttc ggcgatgttt tttctggaga | 240 | |
| tttatgttct atggaatctt tttatattta ggggaagtca ccaaagcagt acagcctctc | 300 | |
| ttactgggaa gaatcatagc ttcctatgac ccggataaca aggaggaacg ctctatcgcg | 360 | |

```
atttatctag gcataggctt atgccttctc tttattgtga ggacactgct cctacaccca      420
gccatttttg gccttcatca cattggaatg cagatgagaa tagctatgtt tagtttgatt      480
tataagaaga ctttaaagct gtcaagccgt gttctagata aaataagtat tggacaactt      540
gttagtctcc tttccaacaa cctgaacaaa tttgatgaag gacttgcatt ggcacatttc      600
gtgtggatcg ctccttttgca agtggcactc ctcatggggc taatctggga gttgttacag      660
gcgtctgcct tctgtggact tggtttcctg atagtccttg ccctttttca ggctgggcta      720
gggagaatga tgatgaagta cagagatcag agagctggga agatcagtga aagacttgtg      780
attacctcag aaatgattga aaatatccaa tctgttaagg catactgctg ggaagaagca      840
atggaaaaaa tgattgaaaa cttaagacaa acagaactga aactgactcg gaaggcagcc      900
tatgtgagat acttcaatag ctcagccttc ttcttctcag gttctttgt ggtgttttta      960 tctgtgcttc cctatgcact aatcaaagga atcatcctcc ggaaaatatt caccaccatc     1020
tcattctgca ttgttctgcg catggcggtc actcggcaat ttccctgggc tgtacaaaca     1080
tggtatgact ctcttggagc aataaacaaa atacaggatt tcttacaaaa gcaagaatat     1140
aagacattgg aatataactt aacgactaca gaagtagtga tggagaatgt aacagccttc     1200
tgggaggaga cttcacttct aatggtgatt atgggagaac tggagccttc agagggtaaa     1260
attaagcaca gtgaagaat tcattctgt tctcagtttt cctggattat gcctggcacc     1320
attaaagaaa atatcatctt tggtgtttcc tatgatgaat atagatacag aagcgtcatc     1380
aaagcatgcc aactagaaga ggacatctcc aagtttgcag agaaagacaa tatagttctt     1440
ggagaaggtg aatcacact gagtggaggt caacgagcaa gaatttcttt agcaagagca     1500
gtatacaaag atgctgattt gtatttatta gactctcctt ttggataccT agatgtttta     1560
acagaaaaag aaatatttga aagctgtgtc tgtaaactga tggctaacaa aactaggatt     1620
ttggtcactt ctaaaatgga acatttaaag aaagctgaca aaatattaat tttgcatgaa     1680
ggtagcagct atttttatgg gacattttca gaactccaaa atctacagcc agactttagc     1740
tcaaaactca tgggatgtga ttctttcgac caatttagtg cagaaagaag aaattcaatc     1800
ctaactgaga ccttacaccg tttctcatta gaaggagatg ctcctgtctc ctggacagaa     1860
acaaaaaaac aatctttaa acagactgga gagtttgggg aaaaaaggaa gaattctatt     1920
ctcaatccaa tcaactctat acgaaaattt tccattgtgc aaaagactcc cttacaaatg     1980
aatggcatcg aagaggattc tgatgagcct ttagagagaa ggctgtcctt agtaccagat     2040
tctgagcagg gagaggcgat actgcctcgc atcagcgtga tcagcactgg ccccacgctt     2100
caggcacgaa ggaggcagtc tgtcctgaac ctgatgacac actcagttaa ccaaggtcag     2160
aacattcacc gaaagacaac agcatccaca cgaaaagtgt cactggcccc tcaggcaaac     2220
ttgactgaac tggatatata ttcaagaagg ttatctcaag aaactggctt ggaaataagt     2280
gaagaaatta cgaagaaga cttaaaggag tgctttttg atgatatgga gagcatacca     2340
gcagtgacta catggaacac ataccttcga tatattactg tccacaagag cttaattttt     2400
gtgctaattt ggtgcttagt aatttttctg gcagaggtgg ctgcttcttt ggttgtgctg     2460
tggctccttg gaaacactcc tcttcaagac aaagggaata gtactcatag tagaaataac     2520
agctatgcag tgattatcac cagcaccagt tcgtattatg tgttttacat ttacgtggga     2580
gtagccgaca ctttgcttgc tatgggattc ttcagaggtc taccactggt gcatactcta     2640
atcacagtgt cgaaaatttt acaccacaaa atgttacatt ctgttcttca agcacctatg     2700
```

```
tcaaccctca acacgttgaa agcaggtggg attcttaata gattctccaa agatatagca    2760
attttggatg accttctgcc tcttaccata tttgacttca tccagttgtt attaattgtg    2820
attggagcta tagcagttgt cgcagtttta caaccctaca tctttgttgc aacagtgcca    2880
gtgatagtgg cttttattat gttgagagca tatttcctcc aaacctcaca gcaactcaaa    2940
caactggaat ctgaaggcag gagtccaatt ttcactcatc ttgttacaag cttaaaagga    3000
ctatggacac ttcgtgcctt cggacggcag ccttactttg aaactctgtt ccacaaagct    3060
ctgaatttac atactgccaa ctggttcttg tacctgtcaa cactgcgctg gttccaaatg    3120
agaatagaaa tgattttttgt catcttcttc attgctgtta ccttcatttc cattttaaca    3180
acaggagaag gagaaggaag agttggtatt atcctgactt tagccatgaa tatcatgagt    3240
acattgcagt gggctgtaaa ctccagcata gatgtggata gcttgatgcg atctgtgagc    3300
cgagtcttta gttcattga catgccaaca gaaggtaaac ctaccaagtc aaccaaacca    3360
tacaagaatg ccaactctc gaaagttatg attattgaga attcacacgt gaagaaagat    3420
gacatctggc cctcagggg ccaaatgact gtcaaagatc tcacagcaaa atacacagaa    3480
ggtggaaatg ccatattaga gaacatttcc ttctcaataa gtcctggcca gagggtgggc    3540
ctcttgggaa gaactggatc agggaagagt actttgttat cagcttttttt gagactactg    3600 aacactgaag gagaaatcca gatcgatggt gtgtcttggg attcaataac tttgcaacag    3660
tggaggaaag cctttggagt gataccacag aaagtattta tttttttctgg aacatttaga    3720 aaaaacttgg atccctatga acagtggagt gatcaagaaa tatggaaagt tgcagatgag    3780
gttgggctca gatctgtgat agaacagttt cctgggaagc ttgactttgt ccttgtggat    3840
gggggctgtg tcctaagcca tggccacaag cagttgatgt gcttggctag atctgttctc    3900
agtaaggcga gatcttgct gcttgatgaa cccagtgctc atttggatcc agtaacatac    3960
caaataatta gaagaactct aaaacaagca tttgctgatt gcacagtaat tctctgtgaa    4020
cacaggatag aagcaatgct ggaatgccaa caatttttgg tcatagaaga gaacaaagtg    4080
cggcagtacg attccatcca gaaactgctg aacgagagga gcctcttccg gcaagccatc    4140 agccctccg acagggtgaa gctctttccc caccggaact caagcaagtg caagtctaag    4200
ccccagattg ctgctctgaa agaggagaca gaagaagagg tgcaagatac aaggctttag    4260
```

<210> SEQ ID NO 4
<211> LENGTH: 4260
<212> TYPE: DNA
<213> ORGANISM: Artificial Sequence
<220> FEATURE:
<223> OTHER INFORMATION: Synthetic Construct

<400> SEQUENCE: 4

```
atgcagagaa gccctctgga aaaggccagc gtggtgtcca agctgttctt cagctggacc      60
cggcctatcc tgcggaaggg ctatagacag agactggaac tgagcgacat ctatcagatc     120
cccagcgtgg acagcgccga caacctgtct gagaagctgg aaagagagtg ggacagagag     180
ctggcctcca agaagaaccc caagctgatc aacgccctgc ggcggtgctt cttctggcgg     240
tttatgttct acggcatctt cctgtacctg ggcgaagtga ccaaagccgt gcagcctctg     300
ctgctgggca gaatcattgc cagctacgac cccgacaaca agaggaacg tctatcgcc     360 atctacctcg cgatcggcct gtgcctgctg tttatcgtca gaaccctgct gctgcacccc     420
gccatctttg gactgcacca catcggcatg cagatgcgga tcgccatgtt cagcctgatc     480
tacaagaaaa ccctgaagct gtccagcaga gtgctggaca agatcagcat cggacagctg     540
```

```
gtgtccctgc tgagcaacaa cctgaacaag ttcgacgaag gcctggctct ggcccacttc    600
gtgtggattg ctcctctgca gtggccctg ctgatgggcc tgatttggga actgctgcag     660
gccagcgcct tttgcggact gggatttctg attgtgctgg ccctgttcca ggccggactg    720
gggagaatga tgatgaagta ccgggaccag agagccggca agatctccga gagactggtc    780
atcaccagcg agatgatcga gaacatccag agcgtgaagg cctactgctg ggaagaggcc    840
atggaaaaga tgattgagaa tctgcggcag accgagctga agctgacaag aaaggccgcc    900
tacgtgcgct acttcaacag cagcgccttc ttcttctccg gcttcttcgt ggtgttcctg    960
agcgtgctgc cctacgctct gatcaagggc atcatcctga aaagattttt caccaccatt   1020
tctttctgca tcgtgctgcg gatggccgtg accagacagt ttccttgggc tgtgcagact   1080
tggtacgata gcctgggcgc catcaacaag atccaggact tcctgcagaa gcaagagtac   1140
aagaccctcg agtacaacct gaccaccacc gaggtggtca tggaaaacgt gaccgccttc   1200
tgggaagaaa ccagcctgct catggtcatc atgggcgagc tgaacctag cgagggcaag    1260 atcaagcaca gcggcaggat cagcttctgt agccagttct cctggatcat gcccggcacc   1320
atcaaagaga acatcatctt cggcgtgtcc tacgacgagt acagataccg cagcgtgatc   1380
aaggcctgcc agctggaaga ggacatcagc aagttcgccg agaaggacaa catcgtgctc   1440
ggcgaaggcg gcatcacact gtctggcgga cagagggcca gaatctctct ggctagagcc   1500
gtgtacaagg acgccgatct gtacctgctg gatagcccct tcggctacct ggatgtgctg   1560
accgagaaag agatcttcga gagctgcgtg tgcaagctga tggccaacaa gaccagaatc   1620
ctggtcacct ccaagatgga acacctgaag aaggccgaca agatcctgat tctgcacgag   1680
ggcagcagct acttttacgg cacccttcag gagctgcaga acctgcagcc tgacttcagc   1740
agcaaactga tgggctgcga ctccttcgac cagttcagcg ccgagcggag aaacagcatc   1800
ctgacagaga cactgcaccg gttctccctg gaaggcgacg ctcctgtgtc ttggaccgag   1860
acaaagaagc agagcttcaa gcagaccggc gagtttggcg agaagcggaa gaactccatt   1920 ctgaaccca tcaactccat ccggaagttc agcatcgtcc agaaaacccc tctgcagatg   1980
aacggcatcg aagaggatag cgacgagccc ctggaaagac ggctgtctct ggtgcctgat   2040
agcgaacagg gcgaagccat cctgcctcgg atctccgtga ttagcacagg ccctacactg   2100
caggctcgga gaaggcagtc tgtgctgaac ctgatgaccc acagcgtgaa ccagggacag   2160
aatatccaca gaaagaccac cgccagcaca cggaaagtgt cactggcccc tcaggccaac   2220
ctgactgagc tggacatcta cagcagacgg ctgagccaag agacaggcct ggaaatcagc   2280
gaggaaatca cgaagagga cctgaaagag tgcttttttcg acgacatgga atctatcccc   2340
gccgtgacaa cctggaatac ctacctgcgg tacatcaccg tgcacaagtc cctgatcttc   2400
gtgctgatct ggtgtctcgt gatcttcctg gccgaagtgg ccgcttctct ggtggttctg   2460
tggctgctgg gaataccccc actgcaggac aagggcaata gcaccacag ccggaacaac    2520 agctacgccg tgatcatcac ctccaccagc tcctactacg tgttctacat ctacgtgggc   2580
gtcgccgaca ctctgctcgc catgggcttt tttagaggac tgcccctggt gcacaccctg   2640
atcaccgtgt ctaagatcct gcaccataag atgctgcaca cgtcctgca ggcccctatg    2700 agcacactga acaccctgaa agccggcgga atcctgaaca gattcagcaa ggacattgcc   2760
atcctggacg acctgctgcc tctgaccatc ttcgacttca tccagctgct gctgatcgtg   2820
atcggcgcca ttgctgtggt ggctgtgctg cagccttaca tcttcgtggc caccgtgcct   2880
```

-continued

```
gtgatcgtgg ccttcattat gctgcgggcc tactttctgc agaccagcca gcagctgaag    2940
cagctcgagt ctgagggcag aagccccatc tttacccacc tcgtgaccag cctgaaaggc    3000
ctgtggaccc tgagagcctt tggcagacag ccctacttcg agacactgtt ccacaaggcc    3060
ctgaacctgc acaccgccaa ctggtttctg tatctgagca ccctgcggtg gttccagatg    3120
aggatcgaga tgattttcgt catcttcttt atcgccgtga ccttcatcag catcctcacc    3180
actggcgaag gcgagggcag agtgggaatc attctgaccc tggccatgaa catcatgtcc    3240
acactccagt gggccgtgaa cagcagcatc gatgtggaca gcctgatgcg agcgtgtcc    3300 cgggtgttca gttcatcga catgcccaca gagggcaagc ccaccaagag caccaagcct    3360
tacaagaacg ccagctgag caaagtcatg atcatcgaga ctcccacgt caagaaggac     3420 gacatttggc ccagcggagg ccagatgacc gtgaaggatc tgaccgccaa gtacaccgaa    3480
ggcggaaacg ccattctgga aaacatcagc tttagcatca gccctggcca gcgcgtggga    3540
ctgcttggaa gaacaggatc tgcaagtct actctgctga gcgccttcct gagactgctg    3600
aataccgagg gcgagatcca gatcgatggg gtgtcctggg acagcatcac cctgcaacaa    3660
tggcggaagg cctttggcgt gatccctcag aaggtgttca ttttcagcgg cacgttccgg    3720
aagaatctgg accgctacga gcagtggagc gaccaagaga tttggaaggt ggccgatgaa    3780
gtgggactga agcgtgat cgagcagttt cccggcaagc tggatttcgt gctggtggat     3840
ggcggctgtg tgctgtctca cggacacaag cagctgatgt gcctggccag aagcgtgctg    3900
tctaaggcca agatcctcct gctggacgag ccctctgctc acctcgatcc tgtgacctac    3960
cagatcatcc ggcggacact gaagcaggcc tttgccgatt gcaccgtgat cctgtgcgag    4020
cacagaatcg aggccatgct ggaatgccag cagtttctgg ttatcgaaga gaacaaagtg    4080
cggcagtacg acagcattca gaagctgctg aacgagcgga gcctgttcag acaggccatc    4140
tctcccagcg acagagtgaa gctgttccct caccggaaca gctccaagtg caagagcaag    4200
cctcagatcg ccgctctgaa agaagaaacc gaggaagagg tgcaggacac acggctgtaa    4260
```

```
<210> SEQ ID NO 5
<211> LENGTH: 1480
<212> TYPE: PRT
<213> ORGANISM: Homo sapiens

<400> SEQUENCE: 5

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
```

-continued

```
            130             135                 140
Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560
```

```
Ala Val Tyr Lys Asp Ala Asp Leu Tyr Leu Leu Asp Ser Pro Phe Gly
            565                 570                 575

Tyr Leu Asp Val Leu Thr Glu Lys Glu Ile Phe Glu Ser Cys Val Cys
        580                 585                 590

Lys Leu Met Ala Asn Lys Thr Arg Ile Leu Val Thr Ser Lys Met Glu
    595                 600                 605

His Leu Lys Lys Ala Asp Lys Ile Leu Ile Leu His Glu Gly Ser Ser
610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
            645                 650                 655

Arg Arg Asn Ser Ile Leu Thr Glu Thr Leu His Arg Phe Ser Leu Glu
        660                 665                 670

Gly Asp Ala Pro Val Ser Trp Thr Glu Thr Lys Lys Gln Ser Phe Lys
    675                 680                 685

Gln Thr Gly Glu Phe Gly Glu Lys Arg Lys Asn Ser Ile Leu Asn Pro
690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
            725                 730                 735

Ser Leu Val Pro Asp Ser Glu Gln Gly Glu Ala Ile Leu Pro Arg Ile
        740                 745                 750

Ser Val Ile Ser Thr Gly Pro Thr Leu Gln Ala Arg Arg Arg Gln Ser
    755                 760                 765

Val Leu Asn Leu Met Thr His Ser Val Asn Gln Gly Gln Asn Ile His
770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
            805                 810                 815

Gly Leu Glu Ile Ser Glu Glu Ile Asn Glu Glu Asp Leu Lys Glu Cys
        820                 825                 830

Phe Phe Asp Asp Met Glu Ser Ile Pro Ala Val Thr Thr Trp Asn Thr
    835                 840                 845

Tyr Leu Arg Tyr Ile Thr Val His Lys Ser Leu Ile Phe Val Leu Ile
850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
            885                 890                 895

His Ser Arg Asn Asn Ser Tyr Ala Val Ile Ile Thr Ser Thr Ser Ser
        900                 905                 910

Tyr Tyr Val Phe Tyr Ile Tyr Val Gly Val Ala Asp Thr Leu Leu Ala
    915                 920                 925

Met Gly Phe Phe Arg Gly Leu Pro Leu Val His Thr Leu Ile Thr Val
930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
            965                 970                 975
```

```
Ser Lys Asp Ile Ala Ile Leu Asp Asp Leu Pro Leu Thr Ile Phe
            980                 985                 990

Asp Phe Ile Gln Leu Leu Leu Ile Val Ile Gly Ala Ile Ala Val Val
            995                1000                1005

Ala Val Leu Gln Pro Tyr Ile Phe Val Ala Thr Val Pro Val Ile Val
            1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
            1045                1050                1055

Thr Ser Leu Lys Gly Leu Trp Thr Leu Arg Ala Phe Gly Arg Gln Pro
            1060                1065                1070

Tyr Phe Glu Thr Leu Phe His Lys Ala Leu Asn Leu His Thr Ala Asn
            1075                1080                1085

Trp Phe Leu Tyr Leu Ser Thr Leu Arg Trp Phe Gln Met Arg Ile Glu
            1090                1095                1100

Met Ile Phe Val Ile Phe Phe Ile Ala Val Thr Phe Ile Ser Ile Leu
1105                1110                1115                1120

Thr Thr Gly Glu Gly Glu Gly Arg Val Gly Ile Ile Leu Thr Leu Ala
            1125                1130                1135

Met Asn Ile Met Ser Thr Leu Gln Trp Ala Val Asn Ser Ser Ile Asp
            1140                1145                1150

Val Asp Ser Leu Met Arg Ser Val Ser Arg Val Phe Lys Phe Ile Asp
            1155                1160                1165

Met Pro Thr Glu Gly Lys Pro Thr Lys Ser Thr Lys Pro Tyr Lys Asn
            1170                1175                1180

Gly Gln Leu Ser Lys Val Met Ile Ile Glu Asn Ser His Val Lys Lys
1185                1190                1195                1200

Asp Asp Ile Trp Pro Ser Gly Gly Gln Met Thr Val Lys Asp Leu Thr
            1205                1210                1215

Ala Lys Tyr Thr Glu Gly Gly Asn Ala Ile Leu Glu Asn Ile Ser Phe
            1220                1225                1230

Ser Ile Ser Pro Gly Gln Arg Val Gly Leu Leu Gly Arg Thr Gly Ser
            1235                1240                1245

Gly Lys Ser Thr Leu Leu Ser Ala Phe Leu Arg Leu Leu Asn Thr Glu
1250                1255                1260

Gly Glu Ile Gln Ile Asp Gly Val Ser Trp Asp Ser Ile Thr Leu Gln
1265                1270                1275                1280

Gln Trp Arg Lys Ala Phe Gly Val Ile Pro Gln Lys Val Phe Ile Phe
            1285                1290                1295

Ser Gly Thr Phe Arg Lys Asn Leu Asp Pro Tyr Glu Gln Trp Ser Asp
            1300                1305                1310

Gln Glu Ile Trp Lys Val Ala Asp Glu Val Gly Leu Arg Ser Val Ile
            1315                1320                1325

Glu Gln Phe Pro Gly Lys Leu Asp Phe Val Leu Val Asp Gly Gly Cys
            1330                1335                1340

Val Leu Ser His Gly His Lys Gln Leu Met Cys Leu Ala Arg Ser Val
1345                1350                1355                1360

Leu Ser Lys Ala Lys Ile Leu Leu Leu Asp Glu Pro Ser Ala His Leu
            1365                1370                1375

Asp Pro Val Thr Tyr Gln Ile Ile Arg Arg Thr Leu Lys Gln Ala Phe
            1380                1385                1390

Ala Asp Cys Thr Val Ile Leu Cys Glu His Arg Ile Glu Ala Met Leu
```

```
                1395                1400                1405
Glu Cys Gln Gln Phe Leu Val Ile Glu Glu Asn Lys Val Arg Gln Tyr
        1410                1415                1420
Asp Ser Ile Gln Lys Leu Leu Asn Glu Arg Ser Leu Phe Arg Gln Ala
1425                1430                1435                1440
Ile Ser Pro Ser Asp Arg Val Lys Leu Phe Pro His Arg Asn Ser Ser
            1445                1450                1455
Lys Cys Lys Ser Lys Pro Gln Ile Ala Ala Leu Lys Glu Glu Thr Glu
                1460                1465                1470
Glu Glu Val Gln Asp Thr Arg Leu
        1475            1480

<210> SEQ ID NO 6
<211> LENGTH: 1419
<212> TYPE: PRT
<213> ORGANISM: Homo sapiens

<400> SEQUENCE: 6

Met Gln Arg Ser Pro Leu Glu Lys Ala Ser Val Val Ser Lys Leu Phe
1               5                   10                  15
Phe Ser Trp Thr Arg Pro Ile Leu Arg Lys Gly Tyr Arg Gln Arg Leu
            20                  25                  30
Glu Leu Ser Asp Ile Tyr Gln Ile Pro Ser Val Asp Ser Ala Asp Asn
        35                  40                  45
Leu Ser Glu Lys Leu Glu Arg Glu Trp Asp Arg Glu Leu Ala Ser Lys
    50                  55                  60
Lys Asn Pro Lys Leu Ile Asn Ala Leu Arg Arg Cys Phe Phe Trp Arg
65                  70                  75                  80
Phe Met Phe Tyr Gly Ile Phe Leu Tyr Leu Gly Glu Val Thr Lys Ala
                85                  90                  95
Val Gln Pro Leu Leu Leu Gly Arg Ile Ile Ala Ser Tyr Asp Pro Asp
            100                 105                 110
Asn Lys Glu Glu Arg Ser Ile Ala Ile Tyr Leu Gly Ile Gly Leu Cys
        115                 120                 125
Leu Leu Phe Ile Val Arg Thr Leu Leu Leu His Pro Ala Ile Phe Gly
    130                 135                 140
Leu His His Ile Gly Met Gln Met Arg Ile Ala Met Phe Ser Leu Ile
145                 150                 155                 160
Tyr Lys Lys Thr Leu Lys Leu Ser Ser Arg Val Leu Asp Lys Ile Ser
                165                 170                 175
Ile Gly Gln Leu Val Ser Leu Leu Ser Asn Asn Leu Asn Lys Phe Asp
            180                 185                 190
Glu Gly Leu Ala Leu Ala His Phe Val Trp Ile Ala Pro Leu Gln Val
        195                 200                 205
Ala Leu Leu Met Gly Leu Ile Trp Glu Leu Leu Gln Ala Ser Ala Phe
    210                 215                 220
Cys Gly Leu Gly Phe Leu Ile Val Leu Ala Leu Phe Gln Ala Gly Leu
225                 230                 235                 240
Gly Arg Met Met Met Lys Tyr Arg Asp Gln Arg Ala Gly Lys Ile Ser
                245                 250                 255
Glu Arg Leu Val Ile Thr Ser Glu Met Ile Glu Asn Ile Gln Ser Val
            260                 265                 270
Lys Ala Tyr Cys Trp Glu Glu Ala Met Glu Lys Met Ile Glu Asn Leu
        275                 280                 285
```

```
Arg Gln Thr Glu Leu Lys Leu Thr Arg Lys Ala Ala Tyr Val Arg Tyr
    290                 295                 300

Phe Asn Ser Ser Ala Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
                355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Thr Ser Leu Leu Met Val Ile Met Gly Glu Leu Glu Pro
                405                 410                 415

Ser Glu Gly Lys Ile Lys His Ser Gly Arg Ile Ser Phe Cys Ser Gln
                420                 425                 430

Phe Ser Trp Ile Met Pro Gly Thr Ile Lys Glu Asn Ile Ile Phe Gly
    435                 440                 445

Val Ser Tyr Asp Glu Tyr Arg Tyr Arg Ser Val Ile Lys Ala Cys Gln
450                 455                 460

Leu Glu Glu Asp Ile Ser Lys Phe Ala Glu Lys Asp Asn Ile Val Leu
465                 470                 475                 480

Gly Glu Gly Gly Ile Thr Leu Ser Gly Gly Gln Arg Ala Arg Ile Ser
                485                 490                 495

Leu Ala Arg Ala Val Tyr Lys Asp Ala Asp Leu Tyr Leu Leu Asp Ser
                500                 505                 510

Pro Phe Gly Tyr Leu Asp Val Leu Thr Glu Lys Glu Ile Phe Glu Ser
    515                 520                 525

Cys Val Cys Lys Leu Met Ala Asn Lys Thr Arg Ile Leu Val Thr Ser
    530                 535                 540

Lys Met Glu His Leu Lys Lys Ala Asp Lys Ile Leu Ile Leu His Glu
545                 550                 555                 560

Gly Ser Ser Tyr Phe Tyr Gly Thr Phe Ser Glu Leu Gln Asn Leu Gln
                565                 570                 575

Pro Asp Phe Ser Ser Lys Leu Met Gly Cys Asp Ser Phe Asp Gln Phe
                580                 585                 590

Ser Ala Glu Arg Arg Asn Ser Ile Leu Thr Glu Thr Leu His Arg Phe
    595                 600                 605

Ser Leu Glu Gly Asp Ala Pro Val Ser Trp Thr Glu Thr Lys Lys Gln
610                 615                 620

Ser Phe Lys Gln Thr Gly Glu Phe Gly Glu Lys Arg Lys Asn Ser Ile
625                 630                 635                 640

Leu Asn Pro Ile Asn Ser Ile Arg Lys Phe Ser Ile Val Gln Lys Thr
                645                 650                 655

Pro Leu Gln Met Asn Gly Ile Glu Glu Asp Ser Asp Glu Pro Leu Glu
                660                 665                 670

Arg Arg Leu Ser Leu Val Pro Asp Ser Glu Gln Gly Glu Ala Ile Leu
    675                 680                 685

Pro Arg Ile Ser Val Ile Ser Thr Gly Pro Thr Leu Gln Ala Arg Arg
    690                 695                 700

Arg Gln Ser Val Leu Asn Leu Met Thr His Ser Val Asn Gln Gly Gln
```

-continued

```
            705                 710                 715                 720
Asn Ile His Arg Lys Thr Thr Ala Ser Thr Arg Lys Val Ser Leu Ala
                    725                 730                 735

Pro Gln Ala Asn Leu Thr Glu Leu Asp Ile Tyr Ser Arg Arg Leu Ser
                    740                 745                 750

Gln Glu Thr Gly Leu Glu Ile Ser Glu Glu Ile Asn Glu Glu Asp Leu
                    755                 760                 765

Lys Glu Cys Phe Phe Asp Asp Met Glu Ser Ile Pro Ala Val Thr Thr
                    770                 775                 780

Trp Asn Thr Tyr Leu Arg Tyr Ile Thr Val His Lys Ser Leu Ile Phe
785                 790                 795                 800

Val Leu Ile Trp Cys Leu Val Ile Phe Leu Ala Glu Val Ala Ala Ser
                    805                 810                 815

Leu Val Val Leu Trp Leu Leu Gly Asn Thr Pro Leu Gln Asp Lys Gly
                    820                 825                 830

Asn Ser Thr His Ser Arg Asn Asn Ser Tyr Ala Val Ile Ile Thr Ser
                    835                 840                 845

Thr Ser Ser Tyr Tyr Val Phe Tyr Ile Tyr Val Gly Val Ala Asp Thr
                    850                 855                 860

Leu Leu Ala Met Gly Phe Phe Arg Gly Leu Pro Leu Val His Thr Leu
865                 870                 875                 880

Ile Thr Val Ser Lys Ile Leu His His Lys Met Leu His Ser Val Leu
                    885                 890                 895

Gln Ala Pro Met Ser Thr Leu Asn Thr Leu Lys Ala Gly Gly Ile Leu
                    900                 905                 910

Asn Arg Phe Ser Lys Asp Ile Ala Ile Leu Asp Asp Leu Leu Pro Leu
                    915                 920                 925

Thr Ile Phe Asp Phe Ile Gln Leu Leu Leu Ile Val Ile Gly Ala Ile
                    930                 935                 940

Ala Val Val Ala Val Leu Gln Pro Tyr Ile Phe Val Ala Thr Val Pro
945                 950                 955                 960

Val Ile Val Ala Phe Ile Met Leu Arg Ala Tyr Phe Leu Gln Thr Ser
                    965                 970                 975

Gln Gln Leu Lys Gln Leu Glu Ser Glu Gly Arg Ser Pro Ile Phe Thr
                    980                 985                 990

His Leu Val Thr Ser Leu Lys Gly Leu Trp Thr Leu Arg Ala Phe Gly
                    995                 1000                1005

Arg Gln Pro Tyr Phe Glu Thr Leu Phe His Lys Ala Leu Asn Leu His
            1010                1015                1020

Thr Ala Asn Trp Phe Leu Tyr Leu Ser Thr Leu Arg Trp Phe Gln Met
1025                1030                1035                1040

Arg Ile Glu Met Ile Phe Val Ile Phe Phe Ile Ala Val Thr Phe Ile
                    1045                1050                1055

Ser Ile Leu Thr Thr Gly Glu Gly Glu Gly Arg Val Gly Ile Ile Leu
                    1060                1065                1070

Thr Leu Ala Met Asn Ile Met Ser Thr Leu Gln Trp Ala Val Asn Ser
            1075                1080                1085

Ser Ile Asp Val Asp Ser Leu Met Arg Ser Val Ser Arg Val Phe Lys
            1090                1095                1100

Phe Ile Asp Met Pro Thr Glu Gly Lys Pro Thr Lys Ser Thr Lys Pro
1105                1110                1115                1120

Tyr Lys Asn Gly Gln Leu Ser Lys Val Met Ile Ile Glu Asn Ser His
            1125                1130                1135
```

-continued

```
Val Lys Lys Asp Asp Ile Trp Pro Ser Gly Gly Gln Met Thr Val Lys
            1140             1145             1150

Asp Leu Thr Ala Lys Tyr Thr Glu Gly Gly Asn Ala Ile Leu Glu Asn
            1155             1160             1165

Ile Ser Phe Ser Ile Ser Pro Gly Gln Arg Val Gly Leu Leu Gly Arg
            1170             1175             1180

Thr Gly Ser Gly Lys Ser Thr Leu Leu Ser Ala Phe Leu Arg Leu Leu
1185             1190             1195             1200

Asn Thr Glu Gly Glu Ile Gln Ile Asp Gly Val Ser Trp Asp Ser Ile
            1205             1210             1215

Thr Leu Gln Gln Trp Arg Lys Ala Phe Gly Val Ile Pro Gln Lys Val
            1220             1225             1230

Phe Ile Phe Ser Gly Thr Phe Arg Lys Asn Leu Asp Pro Tyr Glu Gln
            1235             1240             1245

Trp Ser Asp Gln Glu Ile Trp Lys Val Ala Asp Glu Val Gly Leu Arg
            1250             1255             1260

Ser Val Ile Glu Gln Phe Pro Gly Lys Leu Asp Phe Val Leu Val Asp
1265             1270             1275             1280

Gly Gly Cys Val Leu Ser His Gly His Lys Gln Leu Met Cys Leu Ala
            1285             1290             1295

Arg Ser Val Leu Ser Lys Ala Lys Ile Leu Leu Leu Asp Glu Pro Ser
            1300             1305             1310

Ala His Leu Asp Pro Val Thr Tyr Gln Ile Ile Arg Arg Thr Leu Lys
            1315             1320             1325

Gln Ala Phe Ala Asp Cys Thr Val Ile Leu Cys Glu His Arg Ile Glu
            1330             1335             1340

Ala Met Leu Glu Cys Gln Gln Phe Leu Val Ile Glu Glu Asn Lys Val
1345             1350             1355             1360

Arg Gln Tyr Asp Ser Ile Gln Lys Leu Leu Asn Glu Arg Ser Leu Phe
            1365             1370             1375

Arg Gln Ala Ile Ser Pro Ser Asp Arg Val Lys Leu Phe Pro His Arg
            1380             1385             1390

Asn Ser Ser Lys Cys Lys Ser Lys Pro Gln Ile Ala Ala Leu Lys Glu
            1395             1400             1405

Glu Thr Glu Glu Glu Val Gln Asp Thr Arg Leu
            1410             1415
```

COMPOSITIONS AND METHODS FOR DELIVERING CFTR POLYPEPTIDES

CROSS REFERENCE TO RELATED APPLICATIONS

This application claims the priority benefit of U.S. Provisional Application Ser. No. 62/802,871, filed Feb. 8, 2019, which is incorporated herein by reference in its entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 7613420001100SEQLIST.txt, date recorded: Feb. 4, 2020, size: 44 KB).

FIELD OF THE INVENTION

The present disclosure relates, in part, to recombinant nucleic acids comprising one or more polynucleotides encoding a cystic fibrosis transmembrane conductance regulator (CFTR) polypeptide, viruses comprising the same, pharmaceutical compositions and formulations thereof, and methods of their use (e.g., for providing prophylactic, palliative, or therapeutic relief of one or more signs or symptoms of a chronic lung disease, such as cystic fibrosis).

BACKGROUND

Cystic fibrosis transmembrane conductance regulator (CFTR) is a cAMP-activated chloride and bicarbonate channel that is critical for lung homeostasis. Reduction or loss of CFTR channel function often leads to mucus stasis, chronic bacterial infections, and the accompanying chronic inflammatory responses that promote progressive lung destruction. Decreases in CFTR expression have been suggested to be a component of the lung pathology observed in chronic obstructive pulmonary disease (COPD) patients, and loss-of-function mutations in the CFTR gene lead to the dire consequences associated with cystic fibrosis (CF). 2,000+ unique mutations in the CFTR gene have been described.

CF is an inherited disease characterized by the buildup of thick, sticky mucus that can damage many of the body's organs; however, the most severe pathological consequences are lung-associated. CF patients present with dehydrated mucus in the lungs that leads to airway obstruction, chronic bacterial infections (and associated inflammatory responses), bronchiectasis, and ultimately, respiratory failure. Presently, more than 70,000 people are living with cystic fibrosis worldwide. Historically, children born with CF died as infants, and as recently as 1980 the median survival was less than 20 years. While medical advances in the past three decades have drastically improved both the quality-of-life and life expectancy of CF patients (40.6 years in the United States as of 2013), there exists a clear need for novel treatment options targeting molecular correction of CFTR deficiencies observed in CF patients, as well as in patients suffering from other chronic lung diseases like COPD.

BRIEF SUMMARY

In order to meet these and other needs, provided herein are recombinant nucleic acids (e.g., recombinant herpes virus genomes) encoding one or more CFTR polypeptides for use in viruses (e.g., herpes viruses), pharmaceutical compositions and formulations, medicaments, and/or methods useful for treating CFTR deficiencies in a subject in need thereof and/or for providing prophylactic, palliative, or therapeutic relief of one or more signs or symptoms of a chronic lung disease, such as cystic fibrosis.

The present inventors have shown that the recombinant viruses described herein were capable of effectively transducing airway epithelial cells derived from a CF patient and successfully expressing their encoded exogenous human CFTR polypeptides (see e.g., Example 2). In addition, the present inventors have shown that the recombinant viruses described herein expressed full-length, functional human CFTR which was appropriately trafficked to the plasma membrane (see e.g., Example 2). Furthermore, the present inventors have shown that the recombinant viruses described herein rescued the diseased phenotype in clinically relevant 3D organotypic cultures prepared from biopsies harvested from multiple CF patients harboring various underlying CFTR mutations (see e.g., Example 3). Moreover, the present inventors have shown that recombinant HSV vectors can be administered to the lungs of immunocompetent animals via multiple routes, and further, that a non-invasive inhaled route of administration expressed similar levels of an encoded transgene in, while inducing less cell invasion into, the lungs (see e.g., Example 4). Without wishing to be bound by theory, it is believed that increasing, augmenting, and/or supplementing the levels of CFTR polypeptides in one or more cells (e.g., one or more airway epithelial cells and/or one or more cells of the submucosal glands) of an individual in need thereof by administering one or more of the recombinant nucleic acids, viruses, medicaments, and/or compositions described herein will: 1) reduce or prevent mucus buildup in one or more organs (e.g., the lungs) of the individual; 2) reduce or prevent airway obstruction in the individual; 3) reduce or prevent chronic bacterial infections and/or the associated chronic inflammation in the lungs of the individual; 4) reduce or prevent bronchiectasis in the individual; 5) reduce, inhibit, or treat progressive lung destruction in the individual; and/or 6) provide prophylactic, palliative, or therapeutic relief of one or more signs or symptoms of a chronic lung disease (e.g., cystic fibrosis, COPD, etc.).

Accordingly, certain aspects of the present disclosure relate to a recombinant herpes virus genome comprising one or more polynucleotides encoding a cystic fibrosis transmembrane conductance regulator (CFTR) polypeptide. In some embodiments, the recombinant herpes virus genome is replication competent. In some embodiments, the recombinant herpes virus genome is replication defective. In some embodiments that may be combined with any of the preceding embodiments, the recombinant herpes virus genome comprises the one or more polynucleotides encoding the CFTR polypeptide within one or more viral gene loci. In some embodiments that may be combined with any of the preceding embodiments, the recombinant herpes virus genome is selected from a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any combinations or derivatives thereof.

In some embodiments that may be combined with any of the preceding embodiments, the CFTR polypeptide is a human CFTR polypeptide. In some embodiments that may be combined with any of the preceding embodiments, the CFTR polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 5 or SEQ ID NO: 6. In some embodiments that may be combined with any of the preceding embodiments, the CFTR polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 5. In some embodiments, the CFTR polypeptide comprises the amino acid sequence of SEQ ID NO: 5.

In some embodiments that may be combined with any of the preceding embodiments, the recombinant herpes virus genome is a recombinant herpes simplex virus genome. In some embodiments, the recombinant herpes simplex virus genome is a recombinant type 1 herpes simplex virus (HSV-1) genome, a recombinant type 2 herpes simplex virus (HSV-2) genome, or any derivatives thereof. In some embodiments, the recombinant herpes simplex virus genome is a recombinant HSV-1 genome.

In some embodiments that may be combined with any of the preceding embodiments, the recombinant herpes simplex virus genome comprises an inactivating mutation. In some embodiments, the inactivating mutation is in a herpes simplex virus gene. In some embodiments, the inactivating mutation is a deletion of the coding sequence of the herpes simplex virus gene. In some embodiments, the herpes simplex virus gene is selected from the Infected Cell Protein (ICP) 0 (one or both copies), ICP4 (one or both copies), ICP22, ICP27, ICP47, thymidine kinase (tk), Long Unique Region (UL) 41, and UL55. In some embodiments that may be combined with any of the preceding embodiments, the recombinant herpes simplex virus genome comprises an inactivating mutation in one or both copies of the ICP4 gene. In some embodiments that may be combined with any of the preceding embodiments, the recombinant herpes simplex virus genome comprises an inactivating mutation in the ICP22 gene. In some embodiments that may be combined with any of the preceding embodiments, the recombinant herpes simplex virus genome comprises an inactivating mutation in the UL41 gene. In some embodiments that may be combined with any of the preceding embodiments, the recombinant herpes simplex virus genome comprises an inactivating mutation in one or both copies of the ICP0 gene. In some embodiments that may be combined with any of the preceding embodiments, the recombinant herpes simplex virus genome comprises an inactivating mutation in the ICP27 gene. In some embodiments that may be combined with any of the preceding embodiments, the recombinant herpes simplex virus genome comprises an inactivating mutation in the ICP47 gene. In some embodiments that may be combined with any of the preceding embodiments, the recombinant herpes simplex virus genome comprises an inactivating mutation in the UL55 gene. In some embodiments that may be combined with any of the preceding embodiments, the recombinant herpes simplex virus genome comprises an inactivating mutation in the Joint region. In some embodiments, the recombinant herpes simplex virus genome comprises a deletion of the Joint region.

In some embodiments that may be combined with any of the preceding embodiments, the recombinant herpes simplex virus genome comprises the one or more polynucleotides encoding the CFTR polypeptide within one or more viral gene loci. In some embodiments that may be combined with any of the preceding embodiments, the recombinant herpes simplex virus genome comprises the one or more polynucleotides encoding the CFTR polypeptide within one or both of the ICP4 viral gene loci. In some embodiments that may be combined with any of the preceding embodiments, the recombinant herpes simplex virus genome comprises the one or more polynucleotides encoding the CFTR polypeptide within the ICP22 viral gene locus. In some embodiments that may be combined with any of the preceding embodiments, the recombinant herpes simplex virus genome comprises the one or more polynucleotides encoding the CFTR polypeptide within the UL41 viral gene locus. In some embodiments that may be combined with any of the preceding embodiments, the recombinant herpes simplex virus genome comprises the one or more polynucleotides encoding the CFTR polypeptide within one or both of the ICP0 viral gene loci. In some embodiments that may be combined with any of the preceding embodiments, the recombinant herpes simplex virus genome comprises the one or more polynucleotides encoding the CFTR polypeptide within the ICP27 viral gene locus. In some embodiments that may be combined with any of the preceding embodiments, the recombinant herpes simplex virus genome comprises the one or more polynucleotides encoding the CFTR polypeptide within the ICP47 viral gene locus. In some embodiments that may be combined with any of the preceding embodiments, the recombinant herpes simplex virus genome comprises the one or more polynucleotides encoding the CFTR polypeptide within the UL55 viral gene locus.

In some embodiments that may be combined with any of the preceding embodiments, the recombinant herpes virus genome has reduced cytotoxicity when introduced into a target cell as compared to a corresponding wild-type herpes virus genome. In some embodiments, the target cell is a human cell. In some embodiments that may be combined with any of the preceding embodiments, the target cell is a cell of the respiratory tract. In some embodiments that may be combined with any of the preceding embodiments, the target cell is an airway epithelial cell or a cell of the submucosal glands.

Other aspects of the present disclosure relate to a herpes virus comprising any of the recombinant herpes virus genomes described herein. In some embodiments, the herpes virus is replication competent. In some embodiments, the herpes virus is replication defective. In some embodiments that may be combined with any of the preceding embodiments, the herpes virus has reduced cytotoxicity as compared to a corresponding wild-type herpes virus. In some embodiments, the herpes virus has reduced cytotoxicity when introduced into a target cell as compared to a corresponding wild-type herpes virus. In some embodiments, the target cell is a human cell. In some embodiments that may be combined with any of the preceding embodiments, the target cell is a cell of the respiratory tract. In some embodiments that may be combined with any of the preceding embodiments, the target cell is an airway epithelial cell or a cell of the submucosal glands. In some embodiments that may be combined with any of the preceding embodiments, the herpes virus is selected from a herpes simplex virus, a varicella zoster virus, a human cytomegalovirus, a herpesvirus 6A, a herpesvirus 6B, a herpesvirus 7, a Kaposi's sarcoma-associated herpesvirus, and any combinations or derivatives thereof. In some embodiments that may be combined with any of the preceding embodiments, the herpes virus is a herpes simplex virus. In some embodiments, the herpes simplex virus is an HSV-1, an HSV-2, or any derivatives thereof. In some embodiments, the herpes simplex virus is an HSV-1.

Other aspects of the present disclosure relate to a pharmaceutical composition comprising any of the recombinant herpes virus genomes described herein and/or any of the herpes viruses described herein and a pharmaceutically acceptable excipient. In some embodiments, the pharmaceutical composition is suitable for topical, transdermal, subcutaneous, intradermal, oral, intranasal, intratracheal, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, and/or epicutaneous administration. In some embodiments, the pharmaceutical composition is suitable for oral, intranasal, intratracheal, and/or inhaled administration. In some embodiments, the pharmaceutical composition is suitable for inhaled administration. In some embodiments, the pharmaceutical composition is suitable for non-invasive inhaled administration. In some embodiments, the pharmaceutical composition is suitable for use in a dry powder inhaler, a pressurized metered dose inhaler, a soft mist inhaler, a nebulizer, an electrohydrodynamic aerosol device, or any combinations thereof. In some embodiments, the pharmaceutical composition is suitable for nebulization (e.g., using a vibrating mesh nebulizer). In some embodiments that may be combined with any of the preceding embodiments, the pharmaceutical composition comprises a phosphate buffer. In some embodiments that may be combined with any of the preceding embodiments, the pharmaceutical composition comprises glycerol. In some embodiments that may be combined with any of the preceding embodiments, the pharmaceutical composition comprises a lipid carrier. In some embodiments that may be combined with any of the preceding embodiments, the pharmaceutical composition comprises a nanoparticle carrier.

Other aspects of the present disclosure relate to the use of any of the recombinant nucleic acids, herpes viruses, and/or pharmaceutical compositions described herein as a medicament.

Other aspects of the present disclosure relate to the use of any of the recombinant nucleic acids, herpes viruses, and/or pharmaceutical compositions described herein in a therapy.

Other aspects of the present disclosure relate to the use of any of the recombinant nucleic acids, herpes viruses, and/or pharmaceutical composition described herein in the production or manufacture of a medicament for treating one or more signs or symptoms of a CFTR deficiency and/or a chronic lung disease (e.g., cystic fibrosis, COPD, etc.).

Other aspects of the present disclosure relate to a method of enhancing, increasing, augmenting, and/or supplementing the levels of a CFTR polypeptide in one or more cells of a subject, the method comprising administering to the subject an effective amount of any of the recombinant herpes virus genomes described herein, any of the herpes viruses described herein, and/or any of the pharmaceutical compositions described herein. In some embodiments, the one or more cells are one or more cells of the respiratory tract. In some embodiments, the one or more cells are one or more airway epithelial cells and/or one or more cells of the submucosal glands. In some embodiments that may be combined with any of the preceding embodiments, the subject suffers from a chronic lung disease. In some embodiments, the chronic lung disease is cystic fibrosis or chronic obstructive pulmonary disease (COPD). In some embodiments that may be combined with any of the preceding embodiments, the subject is a human. In some embodiments that may be combined with any of the preceding embodiments, the subject's genome comprises a loss-of-function mutation in a CFTR gene. In some embodiments that may be combined with any of the preceding embodiments, the recombinant herpes virus genome, the herpes virus, and/or the pharmaceutical composition is administered orally, intranasally, intratracheally, sublingually, buccally, topically, rectally, via inhalation, transdermally, subcutaneously, intradermally, intravenously, intraarterially, intramuscularly, intracardially, intraosseously, intraperitoneally, transmucosally, vaginally, intravitreally, intraorbitally, subretinally, intraarticularly, peri-articularly, locally, and/or epicutaneously to the subject. In some embodiments, the recombinant herpes virus genome, the herpes virus, and/or the pharmaceutical composition is administered orally, intranasally, intratracheally, or via inhalation to the subject. In some embodiments, the recombinant herpes virus genome, the herpes virus, and/or the pharmaceutical composition is administered via inhalation to the subject. In some embodiments, the recombinant herpes virus genome, the herpes virus, and/or the pharmaceutical composition is administered via non-invasive inhalation to the subject. In some embodiments, the recombinant herpes virus genome, the herpes virus, and/or the pharmaceutical composition is administered using a dry powder inhaler, a pressurized metered dose inhaler, a soft mist inhaler, a nebulizer, or an electrohydrodynamic aerosol device. In some embodiments, the recombinant herpes virus genome, the herpes virus, and/or the pharmaceutical composition is administered via a nebulizer (e.g., a vibrating mesh nebulizer).

Other aspects of the present disclosure relate to a method of reducing or inhibiting progressive lung destruction in a subject in need thereof, the method comprising administering to the subject an effective amount of any of the recombinant herpes virus genomes described herein, any of the herpes viruses described herein, and/or any of the pharmaceutical compositions described herein. In some embodiments, the subject suffers from a chronic lung disease. In some embodiments, the chronic lung disease is cystic fibrosis or chronic obstructive pulmonary disease (COPD). In some embodiments that may be combined with any of the preceding embodiments, the subject is a human. In some embodiments that may be combined with any of the preceding embodiments, the subject's genome comprises a loss-of-function mutation in a CFTR gene. In some embodiments that may be combined with any of the preceding embodiments, the recombinant herpes virus genome, the herpes virus, and/or the pharmaceutical composition is administered orally, intranasally, intratracheally, sublingually, buccally, topically, rectally, via inhalation, transdermally, subcutaneously, intradermally, intravenously, intraarterially, intramuscularly, intracardially, intraosseously, intraperitoneally, transmucosally, vaginally, intravitreally, intraorbitally, subretinally, intraarticularly, peri-articularly, locally, and/or epicutaneously to the subject. In some embodiments, the recombinant herpes virus genome, the herpes virus, and/or the pharmaceutical composition is administered orally, intranasally, intratracheally, or via inhalation to the subject. In some embodiments, the recombinant herpes virus genome, the herpes virus, and/or the pharmaceutical composition is administered via inhalation to the subject. In some embodiments, the recombinant herpes virus genome, the herpes virus, and/or the pharmaceutical composition is administered via non-invasive inhalation to the subject. In some embodiments, the recombinant herpes virus genome, the herpes virus, and/or the pharmaceutical composition is administered using a dry powder inhaler, a pressurized metered dose inhaler, a soft mist inhaler, a nebulizer, or an electrohydrodynamic aerosol device. In some embodiments, the recombinant herpes virus genome, the herpes virus, and/or the pharmaceutical composition is administered via a nebulizer (e.g., a vibrating mesh nebulizer).

Other aspects of the present disclosure relate to a method of providing prophylactic, palliative, or therapeutic relief of one or more signs or symptoms of cystic fibrosis in a subject in need thereof, the method comprising administering to the subject an effective amount of any of the recombinant herpes virus genomes described herein, any of the herpes viruses described herein, and/or any of the pharmaceutical compositions described herein. In some embodiments, the one or more signs or symptoms of cystic fibrosis are selected from a persistent cough that produces thick mucus, thick sticky mucus that builds up in the airways, wheezing, breathlessness, sinusitis, repeated lung infections, inflamed nasal passages, bronchiectasis, nasal polyps, hemoptysis, pneumothorax, pancreatitis, recurring pneumonia, respiratory failure, and any combinations thereof. In some embodiments that may be combined with any of the preceding embodiments, the subject is a human. In some embodiments that may be combined with any of the preceding embodiments, the subject's genome comprises a loss-of-function mutation in a CFTR gene. In some embodiments that may be combined with any of the preceding embodiments, the recombinant herpes virus genome, the herpes virus, and/or the pharmaceutical composition is administered orally, intranasally, intratracheally, sublingually, buccally, topically, rectally, via inhalation, transdermally, subcutaneously, intradermally, intravenously, intraarterially, intramuscularly, intracardially, intraosseously, intraperitoneally, transmucosally, vaginally, intravitreally, intraorbitally, subretinally, intraarticularly, peri-articularly, locally, and/or epicutaneously to the subject. In some embodiments, the recombinant herpes virus genome, the herpes virus, and/or the pharmaceutical composition is administered orally, intranasally, intratracheally, or via inhalation to the subject. In some embodiments, the recombinant herpes virus genome, the herpes virus, and/or the pharmaceutical composition is administered via inhalation to the subject. In some embodiments, the recombinant herpes virus genome, the herpes virus, and/or the pharmaceutical composition is administered via non-invasive inhalation to the subject. In some embodiments, the recombinant herpes virus genome, the herpes virus, and/or the pharmaceutical composition is administered using a dry powder inhaler, a pressurized metered dose inhaler, a soft mist inhaler, a nebulizer, or an electrohydrodynamic aerosol device. In some embodiments, the recombinant herpes virus genome, the herpes virus, and/or the pharmaceutical composition is administered via a nebulizer (e.g., a vibrating mesh nebulizer).

Other aspects of the present disclosure relate to a method of providing prophylactic, palliative, or therapeutic relief of one or more signs or symptoms of COPD in a subject in need thereof, the method comprising administering to the subject an effective amount of any of the recombinant herpes virus genomes described herein, any of the herpes viruses described herein, and/or any of the pharmaceutical compositions described herein. In some embodiments, the one or more signs or symptoms of COPD are selected from shortness of breath, wheezing, chest tightness, excess mucus in the lungs, a chronic cough, cyanosis, frequent respiratory infections, and any combinations thereof. In some embodiments that may be combined with any of the preceding embodiments, the subject is a human. In some embodiments that may be combined with any of the preceding embodiments, the subject's genome comprises a loss-of-function mutation in a CFTR gene. In some embodiments that may be combined with any of the preceding embodiments, the recombinant herpes virus genome, the herpes virus, and/or the pharmaceutical composition is administered orally, intranasally, intratracheally, sublingually, buccally, topically, rectally, via inhalation, transdermally, subcutaneously, intradermally, intravenously, intraarterially, intramuscularly, intracardially, intraosseously, intraperitoneally, transmucosally, vaginally, intravitreally, intraorbitally, subretinally, intraarticularly, peri-articularly, locally, and/or epicutaneously to the subject. In some embodiments, the recombinant herpes virus genome, the herpes virus, and/or the pharmaceutical composition is administered orally, intranasally, intratracheally, or via inhalation to the subject. In some embodiments, the recombinant herpes virus genome, the herpes virus, and/or the pharmaceutical composition is administered via inhalation to the subject. In some embodiments, the recombinant herpes virus genome, the herpes virus, and/or the pharmaceutical composition is administered via non-invasive inhalation to the subject. In some embodiments, the recombinant herpes virus genome, the herpes virus, and/or the pharmaceutical composition is administered using a dry powder inhaler, a pressurized metered dose inhaler, a soft mist inhaler, a nebulizer, or an electrohydrodynamic aerosol device. In some embodiments, the recombinant herpes virus genome, the herpes virus, and/or the pharmaceutical composition is administered via a nebulizer (e.g., a vibrating mesh nebulizer).

Other aspects of the present disclosure relate to an article of manufacture or kit comprising any of the recombinant herpes virus genomes, herpes viruses, medicaments, and/or pharmaceutical compositions described herein and instructions for administering the recombinant herpes virus genome, herpes virus, medicament, or pharmaceutical composition. In some embodiments, the article of manufacture or kit further comprises a device for aerosolizing the recombinant herpes virus genome, herpes virus, medicament, and/or pharmaceutical composition. In some embodiments, the device is a dry powder inhaler, a pressurized metered dose inhaler, a soft mist inhaler, a nebulizer, or an electrohydrodynamic aerosol device. In some embodiments, the device is a nebulizer (e.g., a vibrating mesh nebulizer).

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-1I show schematics of wild-type and modified herpes simplex virus genomes. FIG. 1A shows a wild-type herpes simplex virus genome. FIG. 1B shows a modified herpes simplex virus genome comprising deletions of the coding sequence of ICP4 (both copies), with an expression cassette containing a nucleic acid encoding a human CFTR polypeptide integrated at each of the ICP4 loci. FIG. 1C shows a modified herpes simplex virus genome comprising deletions of the coding sequences of ICP4 (both copies) and UL41, with an expression cassette containing a nucleic acid encoding a human CFTR polypeptide integrated at each of the ICP4 loci. FIG. 1D shows a modified herpes simplex virus genome comprising deletions of the coding sequences of ICP4 (both copies) and UL41, with an expression cassette containing a nucleic acid encoding a CFTR polypeptide integrated at the UL41 locus. FIG. 1E shows a modified herpes simplex virus genome comprising deletions of the coding sequences of ICP4 (both copies) and ICP22, with an expression cassette containing a nucleic acid encoding a human CFTR polypeptide integrated at each of the ICP4 loci. FIG. 1F shows a modified herpes simplex virus genome comprising deletions of the coding sequences of ICP4 (both copies) and ICP22, with an expression cassette containing a nucleic acid encoding a CFTR polypeptide integrated at the ICP22 locus. FIG. 1G shows a modified herpes simplex virus genome comprising deletions of the coding sequences of ICP4 (both copies), UL41, and ICP22, with an expression cassette containing a nucleic acid encoding a human CFTR polypeptide integrated at each of the ICP4 loci. FIG. 1H shows a modified herpes simplex virus genome comprising deletions of the coding sequences of ICP4 (both copies), UL41, and ICP22, with an expression cassette containing a nucleic acid encoding a CFTR polypeptide integrated at the UL41 locus. FIG. 1I shows a modified herpes simplex virus genome comprising deletions of the coding sequences of ICP4 (both copies), UL41, and ICP22, with an expression cassette containing a nucleic acid encoding a CFTR polypeptide integrated at the ICP22 locus.

FIG. 4A shows the dose-dependent increase in human CFTR protein expression upon infection of primary CF SAECs with increasing MOIs of HSV-CFTR. FIG. 4B shows the relative cellular localization of human CFTR protein in HSV-CFTR infected (MOI 3) or mock infected (MOI 0) primary CF SAECs. DAPI staining was used to visualize nuclei.

FIGS. 6A-6C show analyses of G542X/G542X cystic fibrosis patient-derived intestinal organoids (PDOs) infected with HSV-CFTR at the indicated MOIs. Vehicle alone or an mCherry-encoding HSV vector (mCherry) were used as negative controls; G418 was used as a positive control. FIG. 6A shows representative brightfield images of G542X/G542X PDOs 24 hours after vehicle treatment, or after transduction with either HSV-CFTR or HSV-mCherry at an MOI of 10. Vehicle-treated PDOs isolated from a healthy individual (wild-type) were included and imaged as a comparator. FIG. 6B shows representative images of calcein-stained organoids and the quantification of average organoid size prior to forskolin (Frsk) addition (t=0). FIG. 6C shows representative images of calcein-stained organoids and the quantification of average organoid size 60 minutes after 2 µM Frsk addition (t=60). *p<0.001; **p<0.0001.

FIG. 7A shows representative images of calcein-stained organoids and the quantification of average organoid size prior to forskolin (Frsk) addition (t=0). FIG. 7B shows representative images of calcein-stained organoids and the quantification of average organoid size 60 minutes after 2 µM Frsk addition (t=60). *p<0.05; p<0.01; *p<0.001; ****p<0.0001.

FIG. 8A shows representative images of calcein-stained organoids and the quantification of average organoid size prior to forskolin (Frsk) addition (t=0). FIG. 8B shows representative images of calcein-stained organoids and the quantification of average organoid size 60 minutes after 2 µM Frsk addition (t=60). *p<0.05; ***p<0.001.

FIG. 9A shows representative images of calcein-stained organoids and the quantification of average organoid size prior to forskolin (Frsk) addition (t=0). FIG. 9B shows representative images of calcein-stained organoids and the quantification of average organoid size 60 minutes after 2 µM Frsk addition (t=60). ****p<0.0001.

FIGS. 10A-C show mCherry nucleic acid and protein analyses in lung and trachea biopsies harvested 48 hours after intranasal or intratracheal administration of an mCherry-encoding HSV vector (HSV-mCherry) or vehicle control (mock). FIG. 10A shows the levels of mCherry transcripts present in lung and trachea biopsies, as assessed by qRT-PCR analysis. Data is presented as the average of six replicates±SEM for HSV-mCherry; data is presented as the average of four replicates±SEM for vehicle control. FIG. 10B shows representative immunofluorescence images of mCherry protein expression in lung biopsies after intranasal administration of HSV-mCherry or vehicle control. DAPI staining was used to visualize nuclei; cytokeratin staining was used to visualize epithelial cells. FIG. 10C shows representative immunofluorescence images of mCherry protein expression in lung biopsies after intratracheal administration of HSV-mCherry or vehicle control. DAPI staining was used to visualize nuclei; cytokeratin staining was used to visualize epithelial cells.

DETAILED DESCRIPTION

Figure 1C:
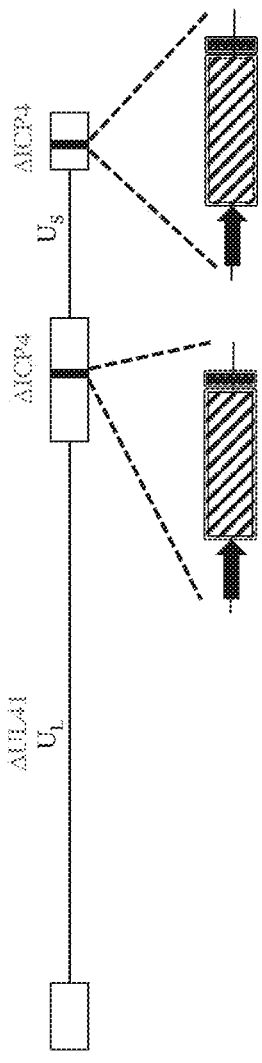

The following description sets forth exemplary methods, parameters, and the like. It should be recognized, however, that such a description is not intended as a limitation on the scope of the present disclosure but is instead provided as a description of exemplary embodiments.

All references cited herein, including patent applications, patent publications, non-patent literature, and NCBI/UniProtKB/Swiss-Prot accession numbers are herein incorporated by reference in their entirety, as if each individual reference were specifically and individually indicated to be incorporated by reference.

I. General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series Methods in Enzymology (Academic Press, Inc.): *PCR 2: A Practical Approach* (M. J. MacPherson, B. D. Hames and G. R. Taylor eds. (1995)), Harlow and Lane, eds. (1988); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Gene Transfer Vectors for Mammalian Cells* (J. M. Miller and M. P. Calos, eds., 1987); *PCR: The Polymerase Chain Reaction*, (Mullis et al., eds., 1994); *Short Protocols in Molecular Biology* (Wiley and Sons, 1999).

II. Definitions

Before describing the present disclosure in detail, it is to be understood that the present disclosure is not limited to particular compositions or biological systems, which can, of course, vary. It is also to be understood that the terminology used herein is for the purpose of describing particular embodiments only and is not intended to be limiting.

As used herein, the singular forms "a", "an" and "the" include plural referents unless the content clearly dictates otherwise. Thus, for example, reference to "a molecule" optionally includes a combination of two or more such molecules, and the like.

As used herein, the term "and/or" may include any and all combinations of one or more of the associated listed items. For example, the term "a and/or b" may refer to "a alone", "b alone", "a or b", or "a and b"; the term "a, b, and/or c" may refer to "a alone", "b alone", "c alone", "a or b", "a or c", "b or c", "a, b, or c", "a and b", "a and c", "b and c", or "a, b, and c"; etc.

As used herein, the term "about" refers to the usual error range for the respective value readily known to the skilled person in this technical field. Reference to "about" a value or parameter herein includes (and describes) embodiments that are directed to that value or parameter per se.

It is understood that aspects and embodiments of the present disclosure include "comprising", "consisting", and "consisting essentially of" aspects and embodiments.

As used herein, the terms "polynucleotide", "nucleic acid sequence", "nucleic acid", and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications.

As used herein, a nucleic acid is "operatively linked" or "operably linked" when it is placed into a functional relationship with another nucleic acid sequence. For example, a promoter or enhancer is operably linked to a coding sequence if it affects the transcription of the sequence, or a ribosome binding site is operably linked to a coding sequence if it is positioned so as to facilitate translation. Generally, "operatively linked" or "operably linked" means that the DNA or RNA sequences being linked are contiguous.

As used herein, the term "vector" refers to discrete elements that are used to introduce heterologous nucleic acids into cells for either expression or replication thereof. An expression vector includes vectors capable of expressing nucleic acids that are operatively linked with regulatory sequences, such as promoter regions, that are capable of effecting expression of such nucleic acids. Thus, an expression vector may refer to a DNA or RNA construct, such as a plasmid, a phage, recombinant virus or other vector that, upon introduction into an appropriate host cell, results in expression of the nucleic acids. Appropriate expression vectors are well known to those of skill in the art and include those that are replicable in eukaryotic cells and those that remain episomal or those which integrate into the host cell genome.

As used herein, an "open reading frame" or "ORF" refers to a continuous stretch of nucleic acids, either DNA or RNA, that encode a protein or polypeptide. Typically, the nucleic acids comprise a translation start signal or initiation codon, such as ATG or AUG, and a termination codon.

As used herein, an "untranslated region" or "UTR" refers to untranslated nucleic acids at the 5' and/or 3' ends of an open reading frame. The inclusion of one or more UTRs in a polynucleotide may affect post-transcriptional regulation, mRNA stability, and/or translation of the polynucleotide.

As used herein, the term "transgene" refers to a polynucleotide that is capable of being transcribed into RNA and translated and/or expressed under appropriate conditions after being introduced into a cell. In some embodiments, it confers a desired property to a cell into which it was introduced, or otherwise leads to a desired therapeutic or diagnostic outcome.

As used herein, the terms "polypeptide," "protein," and "peptide" are used interchangeably and may refer to a polymer of two or more amino acids.

As used herein, a "subject", "host", or an "individual" refers to any animal classified as a mammal, including humans, domestic and farm animals, and zoo, sports, or pet animals, such as dogs, horses, cats, cows, as well as animals used in research, such as mice, rats, hamsters, rabbits, and non-human primates, etc. In some embodiments, the mammal is human.

As used herein, the terms "pharmaceutical formulation" or "pharmaceutical composition" refer to a preparation which is in such a form as to permit the biological activity of the active ingredient(s) to be effective, and which contains no additional components which are unacceptably toxic to a subject to which the composition or formulation would be administered. "Pharmaceutically acceptable" excipients (e.g., vehicles, additives) are those which can reasonably be administered to a subject mammal to provide an effective dose of the active ingredient(s) employed.

As used herein, an "effective amount" is at least the minimum amount required to affect a measurable improvement or prevention of one or more symptoms of a particular disorder. An "effective amount" may vary according to factors such as the disease state, age, sex, and weight of the patient. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications used to treat symptoms of the disease, delaying the progression of the disease, and/or prolonging survival. An effective amount can be administered in one or more administrations. For purposes of the present disclosure, an effective amount of a recombinant nucleic acid, virus, and/or pharmaceutical composition is an amount sufficient to accomplish prophylactic or therapeutic treatment either directly or indirectly. As is understood in the clinical context, an effective amount of a recombinant nucleic acid, virus, and/or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "treatment" refers to clinical intervention designed to alter the natural course of the individual or cell being treated during the course of clinical pathology. Desirable effects of treatment include decreasing the rate of disease/disorder/defect progression, ameliorating or palliating the disease/disorder/defect state, and remission or improved prognosis. For example, an individual is successfully "treated" if one or more symptoms associated with a chronic lung disease (e.g., cystic fibrosis or COPD) are mitigated or eliminated.

As used herein, the term "delaying progression of" a disease/disorder/defect refers to deferring, hindering, slowing, retarding, stabilizing, and/or postponing development of the disease/disorder/defect (e.g., cystic fibrosis or COPD). This delay can be of varying lengths or time, depending on the history of the disease/disorder/defect and/or the individual being treated. As is evident to one of ordinary skill in the art, a sufficient or significant delay can, in effect, encompass prevention, in that the individual does not develop the disease.

III. Recombinant Nucleic Acids

Certain aspects of the present disclosure relate to recombinant nucleic acids (e.g., isolated recombinant nucleic acids) comprising one or more (e.g., one or more, two or more, three or more, four or more, five or more, ten or more, etc.) polynucleotides encoding a CFTR polypeptide (e.g., a human CFTR polypeptide). In some embodiments, the recombinant nucleic acid comprises one polynucleotide encoding a CFTR polypeptide. In some embodiments, the recombinant nucleic acid comprises two polynucleotides encoding a CFTR polypeptide. In some embodiments, the recombinant nucleic acid comprises three polynucleotides encoding a CFTR polypeptide.

In some embodiments, the recombinant nucleic acid is a vector. In some embodiments, the recombinant nucleic acid is a viral vector. In some embodiments, the recombinant nucleic acid is a herpes viral vector. In some embodiments, the recombinant nucleic acid is a herpes simplex virus amplicon. In some embodiments, the recombinant nucleic acid is a recombinant herpes virus genome. In some embodiments, the recombinant nucleic acid is a recombinant herpes simplex virus genome. In some embodiments, the recombinant nucleic acid is a recombinant herpes simplex virus type 1 (HSV-1) genome.

Polynucleotides encoding Cystic fibrosis transmembrane conductance regulator (CFTR) polypeptides In some embodiments, the present disclosure relates to a recombinant nucleic acid comprising one or more polynucleotides comprising the coding sequence of a CFTR gene (e.g., a human CFTR gene), or any portions thereof. The sequence of any suitable CFTR gene (including any isoform thereof) known in the art may be encoded by a polynucleotide of the present disclosure, including, for example, a human CFTR gene (see e.g., NCBI Gene ID: 1080; SEQ ID NO: 1 or SEQ ID NO: 3), a chimpanzee CFTR gene (see e.g., NCBI Gene ID: 463674), a mouse CFTR gene (see e.g., NCBI Gene ID: 12638), a rat CFTR gene (see e.g., NCBI Gene ID: 24255), a dog CFTR gene (see e.g., NCBI Gene ID: 492302), a rabbit CFTR gene (see e.g., NCBI Gene ID: 100009471), a cow CFTR gene (see e.g., NCBI Gene ID: 281067), a rhesus monkey CFTR gene (see e.g., NCBI Gene ID: 574346), etc. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the CFTR genes described herein or known in the art (and/or the coding sequences thereof). Methods of identifying CFTR gene homologs/orthologs from additional species are known to one of ordinary skill in the art, including, for example, using a nucleic acid sequence alignment program such as the BLAST® blastn suite.

In some embodiments, a polynucleotide of the present disclosure comprises a codon-optimized variant of any of the CFTR genes described herein or known in the art. In some embodiments, a polynucleotide of the present disclosure comprises a codon-optimized variant of the coding sequence of any of the CFTR genes described herein or known in the art. In some embodiments, use of a codon-optimized variant of a CFTR gene increases stability and/or yield of heterologous expression (RNA and/or protein) of the encoded CFTR polypeptide in a target cell (e.g., a target human cell such as a human airway epithelial cell), as compared to the stability and/or yield of heterologous expression of a corresponding non-codon-optimized, wild-type sequence. Any suitable method known in the art for performing codon optimization of a sequence for expression in one or more target cells (e.g., one or more cells of the lung) may be used, including, for example, by the methods described by Fath et al. (PLoS One. 2011 Mar. 3; 6(3): e17596).

In some embodiments, one or more polynucleotides of the present disclosure comprise the coding sequence of a human CFTR gene.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 1. In some embodiments, a polynucleotide of the present disclosure comprises the sequence of SEQ ID NO: 1.

In some embodiments, a polynucleotide of the present disclosure comprises a 5' truncation, a 3' truncation, or a fragment of the sequence of SEQ ID NO: 1. In some embodiments, the 5' truncation, 3' truncation, or fragment of the sequence of SEQ ID NO: 1 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2250, at least 2500, at least 2750, at least 3000, at least 3250, at least 3500, at least 3750, at least 4000, at least 4250, but fewer than 4443 consecutive nucleotides of SEQ ID NO: 1. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-4440 of SEQ ID NO: 1. In some embodiments, a polynucleotide of the present disclosure comprises the sequence of nucleic acids 1-4440 of SEQ ID NO: 1.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 3. In some embodiments, a polynucleotide of the present disclosure comprises the sequence of SEQ ID NO: 3.

In some embodiments, a polynucleotide of the present disclosure comprises a 5' truncation, a 3' truncation, or a fragment of the sequence of SEQ ID NO: 3. In some embodiments, the 5' truncation, 3' truncation, or fragment of the sequence of SEQ ID NO: 3 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2250, at least 2500, at least 2750, at least 3000, at least 3250, at least 3500, at least 3750, at least 4000, at least 4250, but fewer than 4260 consecutive nucleotides of SEQ ID NO: 3. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-4257 of SEQ ID NO: 3. In some embodiments, a polynucleotide of the present disclosure comprises the sequence of nucleic acids 1-4257 of SEQ ID NO: 3.

In some embodiments, a polynucleotide of the present disclosure comprises the coding sequence of a codon-optimized variant of a human CFTR gene.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 2. In some embodiments, a polynucleotide of the present disclosure comprises the sequence of SEQ ID NO: 2.

In some embodiments, a polynucleotide of the present disclosure comprises a 5' truncation, a 3' truncation, or a fragment of the sequence of SEQ ID NO: 2. In some embodiments, the 5' truncation, 3' truncation, or fragment of the sequence of SEQ ID NO: 2 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2250, at least 2500, at least 2750, at least 3000, at least 3250, at least 3500, at least 3750, at least 4000, at least 4250, but fewer than 4443 consecutive nucleotides of SEQ ID NO: 2. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-4440 of SEQ ID NO: 2. In some embodiments, a polynucleotide of the present disclosure comprises the sequence of nucleic acids 1-4440 of SEQ ID NO: 2.

In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 4. In some embodiments, a polynucleotide of the present disclosure comprises the sequence of SEQ ID NO: 4.

In some embodiments, a polynucleotide of the present disclosure comprises a 5' truncation, a 3' truncation, or a fragment of the sequence of SEQ ID NO: 4. In some embodiments, the 5' truncation, 3' truncation, or fragment of the sequence of SEQ ID NO: 4 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2250, at least 2500, at least 2750, at least 3000, at least 3250, at least 3500, at least 3750, at least 4000, at least 4250, but fewer than 4260 consecutive nucleotides of SEQ ID NO: 4. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-4257 of SEQ ID NO: 4. In some embodiments, a polynucleotide of the present disclosure comprises the sequence of nucleic acids 1-4257 of SEQ ID NO: 4.

In some embodiments, a polynucleotide of the present disclosure comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-4. In some embodiments, a polynucleotide of the present disclosure comprises a sequence selected from SEQ ID NOS: 1-4. In some embodiments, a polynucleotide of the present disclosure comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NO: 1 or SEQ ID NO: 2. In some embodiments, a polynucleotide of the present disclosure comprises a sequence selected from SEQ ID NO: 1 or SEQ ID NO: 2. In some embodiments, a polynucleotide of the present disclosure comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NO: 3 or SEQ ID NO: 4. In some embodiments, a polynucleotide of the present disclosure comprises a sequence selected from SEQ ID NO: 3 or SEQ ID NO: 4.

A polynucleotide of the present disclosure (e.g., encoding a human CFTR polypeptide) may further encode additional coding and non-coding sequences. Examples of additional coding and non-coding sequences may include, but are not limited to, sequences encoding additional polypeptide tags (e.g., encoded in-frame with the CFTR protein in order to produce a fusion protein), introns (e.g., native, modified, or heterologous introns), 5' and/or 3' UTRs (e.g., native, modified, or heterologous 5' and/or 3' UTRs), and the like. Examples of suitable polypeptide tags may include, but are not limited to, any combination of purification tags, such as his-tags, flag-tags, maltose binding protein and glutathione-S-transferase tags, detection tags, such as tags that may be detected photometrically (e.g., green fluorescent protein, red fluorescent protein, etc.) and tags that have a detectable enzymatic activity (e.g., alkaline phosphatase, etc.), tags containing secretory sequences, signal sequences, leader sequences, and/or stabilizing sequences, protease cleavage sites (e.g., furin cleavage sites, TEV cleavage sites, Thrombin cleavage sites, etc.), and the like. In some embodiments, the 5' and/or 3'UTRs increase the stability, localization, and/or translational efficiency of the polynucleotides. In some embodiments, the 5' and/or 3'UTRs improve the level and/or duration of protein expression. In some embodiments, the 5' and/or 3'UTRs include elements (e.g., one or more miRNA binding sites, etc.) that may block or reduce off-target expression (e.g., inhibiting expression in specific cell types (e.g., neuronal cells), at specific times in the cell cycle, at specific developmental stages, etc.). In some embodiments, the 5' and/or 3'UTRs include elements (e.g., one or more miRNA binding sites, etc.) that may enhance CFTR expression in specific cell types.

In some embodiments, a polynucleotide of the present disclosure (e.g., encoding a human CFTR polypeptide) is operably linked to one or more (e.g., one or more, two or more, three or more, four or more, five or more, ten or more, etc.) regulatory sequences. The term "regulatory sequence" may include enhancers, insulators, promoters, and other expression control elements (e.g., polyadenylation signals). Any suitable enhancer(s) known in the art may be used, including, for example, enhancer sequences from mammalian genes (such as globin, elastase, albumin, α-fetoprotein, insulin and the like), enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like), and any combinations thereof. Any suitable insulator(s) known in the art may be used, including, for example, herpes simplex virus (HSV) chromatin boundary (CTRL/CTCF-binding/insulator) elements CTRL1 and/or CTRL2, chicken hypersensitive site 4 insulator (cHS4), human HNRPA2B1-CBX3 ubiquitous chromatin opening element (UCOE), the scaffold/matrix attachment region (S/MAR) from the human interferon beta gene (IFNB1), and any combinations thereof. Any suitable promoter (e.g., suitable for transcription in mammalian host cells) known in the art may be used, including, for example, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), promoters from heterologous mammalian genes (such as the actin promoter (e.g., the (3-actin promoter), a ubiquitin promoter (e.g., a ubiquitin C (UbC) promoter), a phosphoglycerate kinase (PGK) promoter, an immunoglobulin promoter, from heat-shock protein promoters, and the like), promoters from native and/or homologous mammalian genes (e.g., a human CFTR gene promoter), synthetic promoters (such as the CAGG promoter), and any combinations thereof, provided such promoters are compatible with the host cells. Regulatory sequences may include those which direct constitutive expression of a nucleic acid, as well as tissue-specific regulatory and/or inducible or repressible sequences.

In some embodiments, a polynucleotide of the present disclosure is operably linked to one or more heterologous promoters. In some embodiments, the one or more heterologous promoters are one or more of constitutive promoters, tissue-specific promoters, temporal promoters, spatial promoters, inducible promoters and repressible promoters. In some embodiments, the one or more heterologous promoters are one or more of the human cytomegalovirus (HCMV) immediate early promoter, the human elongation factor-1 (EF1) promoter, the human β-actin promoter, the human UbC promoter, the human PGK promoter, the synthetic CAGG promoter, and any combinations thereof. In some embodiments, a polynucleotide of the present disclosure (e.g., encoding a human CFTR polypeptide) is operably linked to an HCMV promoter.

In some embodiments, a polynucleotide of the present disclosure does not comprise the coding sequence of (e.g., a transgene encoding) a Collagen alpha-1 (VII) chain polypeptide (COLT). In some embodiments, a polynucleotide of the present disclosure does not comprise the coding sequence of (e.g., a transgene encoding) a Lysyl hydroxylase 3 polypeptide (LH3). In some embodiments, a polynucleotide of the present disclosure does not comprise the coding sequence of (e.g., a transgene encoding) a Keratin type I cytoskeletal 17 polypeptide (KRT17). In some embodiments, a polynucleotide of the present disclosure does not comprise the coding sequence of (e.g., a transgene encoding) a transglutaminase (TGM) polypeptide (e.g., a human transglutaminase polypeptide such as a human TGM1 polypeptide and/or a human TGM5 polypeptide). In some embodiments, a polynucleotide of the present disclosure does not comprise the coding sequence of (e.g., a transgene encoding) a cosmetic protein (e.g., collagen proteins, fibronectins, elastins, lumicans, vitronectins/vitronectin receptors, laminins, neuromodulators, fibrillins, additional dermal extracellular matrix proteins, etc.). In some embodiments, a polynucleotide of the present disclosure does not comprise the coding sequence of (e.g., a transgene encoding) an antibody (e.g., a full-length antibody, an antibody fragment, etc.). In some embodiments, a polynucleotide of the present disclosure does not comprise the coding sequence of (e.g., a transgene encoding) a Serine Protease Inhibitor Kazal-type (SPINK) polypeptide (e.g., a human SPINK polypeptide, such as a SPINK5 polypeptide). In some embodiments, a polynucleotide of the present disclosure does not comprise the coding sequence of (e.g., a transgene encoding) a filaggrin or filaggrin 2 polypeptide (e.g., a human filaggrin or filaggrin 2 polypeptide). In some embodiments, a polynucleotide of the present disclosure does not comprise the coding sequence of (e.g., a transgene encoding) a Collagen alpha-1 (VII) chain polypeptide, a Lysyl hydroxylase 3 polypeptide, a Keratin type I cytoskeletal 17 polypeptide, and/or any chimeric polypeptides thereof. In some embodiments, a polynucleotide of the present disclosure does not comprise the coding sequence of (e.g., a transgene encoding) a Collagen alpha-1 (VII) chain polypeptide, a Lysyl hydroxylase 3 polypeptide, a Keratin type I cytoskeletal 17 polypeptide, a transglutaminase (TGM) polypeptide, a filaggrin polypeptide, a cosmetic protein, an antibody, a SPINK polypeptide, and/or any chimeric polypeptides thereof.

Cystic Fibrosis Transmembrane Conductance Regulator (CFTR) Polypeptides

In some embodiments, the present disclosure relates to one or more polynucleotides encoding a CFTR polypeptide (e.g., a human CFTR polypeptide), or any portions thereof. Any suitable CFTR polypeptide known in the art may be encoded by a polynucleotide of the present disclosure, including, for example, a human CFTR polypeptide (see e.g., UniProt accession number P13569; SEQ ID NO: 5 or SEQ ID NO: 6), a chimpanzee CFTR polypeptide (see e.g., UniProt accession number Q2QLE5), a mouse CFTR polypeptide (see e.g., UniProt accession number P26361), a rat CFTR polypeptide (see e.g., UniProt accession number P34158), a rabbit CFTR polypeptide (see e.g., UniProt accession number Q00554), a rhesus monkey CFTR polypeptide (see e.g., UniProt accession number Q00553), etc. In some embodiments, a CFTR polypeptide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of any of the CFTR polypeptides described herein or known in the art. Methods of identifying CFTR polypeptide homologs/orthologs from additional species are known to one of ordinary skill in the art, including, for example, using an amino acid sequence alignment program such as the BLAST® blastp suite or OrthoDB.

In some embodiments, a CFTR polypeptide of the present disclosure is a human CFTR polypeptide.

In some embodiments, a polynucleotide encoding a human CFTR polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 5. In some embodiments, a polynucleotide encoding a human CFTR polypeptide is a polynucleotide that encodes a polypeptide comprising the amino acid sequence of SEQ ID NO: 5.

In some embodiments, a polynucleotide encoding a human CFTR polypeptide is a polynucleotide that encodes an N-terminal truncation, a C-terminal truncation, or a fragment of the amino acid sequence of SEQ ID NO: 5. N-terminal truncations, C-terminal truncations, or fragments may comprise at least 10, at least 12, at least 14, at least 16, at least 18, at least 20, at least 30, at least 40, at least 50, at least 75, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1100, at least 1200, at least 1300, at least 1400, but fewer than 1480, consecutive amino acids of SEQ ID NO: 5.

In some embodiments, a polynucleotide encoding a human CFTR polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to the sequence of SEQ ID NO: 6. In some embodiments, a polynucleotide encoding a human CFTR polypeptide is a polynucleotide that encodes a polypeptide comprising the amino acid sequence of SEQ ID NO: 6.

In some embodiments, a polynucleotide encoding a human CFTR polypeptide is a polynucleotide that encodes an N-terminal truncation, a C-terminal truncation, or a fragment of the amino acid sequence of SEQ ID NO: 6. N-terminal truncations, C-terminal truncations, or fragments may comprise at least 10, at least 12, at least 14, at least 16, at least 18, at least 20, at least 30, at least 40, at least 50, at least 75, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1100, at least 1200, at least 1300, at least 1400, but fewer than 1419, consecutive amino acids of SEQ ID NO: 6.

In some embodiments, a polynucleotide of the present disclosure encoding a CFTR polypeptide is a polynucleotide that encodes a polypeptide comprising a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 5 or SEQ ID NO: 6. In some embodiments, a polynucleotide of the present disclosure encoding a CFTR polypeptide is a polynucleotide that encodes a polypeptide comprising the amino acid sequence of SEQ ID NO: 5 or SEQ ID NO: 6.

In some embodiments, a polynucleotide of the present disclosure encoding a CFTR polypeptide (e.g., a human CFTR polypeptide) expresses the CFTR polypeptide when the polynucleotide is delivered into one or more target cells of a subject (e.g., one or more cells of the airway and/or lungs of the subject). In some embodiments, expression of the CFTR polypeptide (e.g., a human CFTR polypeptide) enhances, increases, augments, and/or supplements the levels, function, and/or activity of a CFTR polypeptide in one or more target cells of a subject (e.g., as compared to prior to expression of the CFTR polypeptide). In some embodiments, expression of the CFTR polypeptide (e.g., a human CFTR polypeptide) reduces mucus secretion by one or more cells and/or in one or more organs (e.g., the lungs) of the subject (e.g., as compared to prior to expression of the CFTR polypeptide). In some embodiments, expression of the CFTR polypeptide (e.g., a human CFTR polypeptide) reduces and/or inhibits mucus buildup in one or more organs (e.g., the lungs) of the subject (e.g., as compared to prior to expression of the CFTR polypeptide). In some embodiments, expression of the CFTR polypeptide (e.g., a human CFTR polypeptide) reduces, prevents, or treats airway obstruction in a subject (e.g., as compared to prior to expression of the CFTR polypeptide). In some embodiments, expression of the CFTR polypeptide (e.g., a human CFTR polypeptide) reduces, prevents, or treats chronic bacterial infections and/or the associated chronic inflammation in the lungs of a subject (e.g., as compared to prior to expression of the CFTR polypeptide). In some embodiments, expression of the CFTR polypeptide (e.g., a human CFTR polypeptide) reduces, inhibits, prevents, or treats bronchiectasis in a subject (e.g., as compared to prior to expression of the CFTR polypeptide). In some embodiments, expression of the CFTR polypeptide (e.g., a human CFTR polypeptide) reduces, inhibits, prevents, or treats progressive lung destruction in a subject (e.g., as compared to prior to expression of the CFTR polypeptide). In some embodiments, expression of the CFTR polypeptide (e.g., a human CFTR polypeptide) provides prophylactic, palliative, or therapeutic relief of a chronic lung disease (e.g., cystic fibrosis, chronic obstructive pulmonary disorder) in a subject (e.g., as compared to prior to expression of the CFTR polypeptide). In some embodiments, expression of the CFTR polypeptide (e.g., a human CFTR polypeptide) provides prophylactic, palliative, or therapeutic relief of one or more signs or symptoms of cystic fibrosis in a subject (e.g., as compared to prior to expression of the CFTR polypeptide).

Recombinant Nucleic Acids

In some embodiments, the present disclosure relates to recombinant nucleic acids comprising any one or more of the polynucleotides described herein. In some embodiments, the recombinant nucleic acid is a vector (e.g., an expression vector, a display vector, etc.). In some embodiments, the vector is a DNA vector or an RNA vector. Generally, vectors suitable to maintain, propagate, and/or express polynucleotides to produce one or more polypeptides in a subject may be used. Examples of suitable vectors may include, for example, plasmids, cosmids, episomes, transposons, and viral vectors (e.g., adenoviral vectors, adeno-associated viral vectors, vaccinia viral vectors, Sindbis-viral vectors, measles vectors, herpes viral vectors, lentiviral vectors, retroviral vectors, etc.). In some embodiments, the vector is a herpes viral vector. In some embodiments, the vector is capable of autonomous replication in a host cell. In some embodiments, the vector is incapable of autonomous replication in a host cell. In some embodiments, the vector can integrate into a host DNA. In some embodiments, the vector cannot integrate into a host DNA (e.g., is episomal). Methods of making vectors containing one or more polynucleotides of interest are well known to one of ordinary skill in the art, including, for example, by chemical synthesis or by artificial manipulation of isolated segments of nucleic acids (e.g., by genetic engineering techniques).

In some embodiments, a recombinant nucleic acid of the present disclosure is a herpes simplex virus (HSV) amplicon. Herpes virus amplicons, including the structural features and methods of making the same, are generally known to one of ordinary skill in the art (see e.g., de Silva S. and Bowers W. "Herpes Virus Amplicon Vectors". *Viruses* 2009, 1, 594-629). In some embodiments, the herpes simplex virus amplicon is an HSV-1 amplicon. In some embodiments, the herpes simplex virus amplicon is an HSV-1 hybrid amplicon. Examples of HSV-1 hybrid amplicons may include, but are not limited to, HSV/AAV hybrid amplicons, HSV/EBV hybrid amplicons, HSV/EBV/RV hybrid amplicons, and/or HSV/Sleeping Beauty hybrid amplicons. In some embodiments, the amplicon is an HSV/AAV hybrid amplicon. In some embodiments, the amplicon is an HSV/Sleeping Beauty hybrid amplicon.

In some embodiments, a recombinant nucleic acid of the present disclosure is a recombinant herpes virus genome. The recombinant herpes virus genome may be a recombinant genome from any member of the Herpesviridae family of DNA viruses known in the art, including, for example, a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any combinations or derivatives thereof. As used herein, an "inactivating mutation" may refer to any mutation that results in a gene or regulon product (RNA or protein) having reduced, undetectable, or eliminated quantity and/or function (e.g., as compared to a corresponding sequence lacking the inactivating mutation). Examples of inactivating mutations may include, but are not limited to, deletions, insertions, point mutations, and rearrangements in transcriptional control sequences (promoters, enhancers, insulators, etc.) and/or coding sequences of a given gene or regulon. Any suitable method of measuring the quantity of a gene or regulon product known in the art may be used, including, for example, qPCR, Northern blots, RNAseq, western blots, ELISAs, etc. In some embodiments, the recombinant herpes virus genome comprises one or more (e.g., one or more, two or more, three or more, four or more, five or more, six or more, seven or more, eight or more, nine or more, ten or more, etc.) inactivating mutations. In some embodiments, the one or more inactivating mutations are in one or more (e.g., one or more, two or more, three or more, four or more, five or more, six or more, seven or more, eight or more, nine or more, ten or more, etc.) herpes virus genes. In some embodiments, the recombinant herpes virus genome is attenuated (e.g., as compared to a corresponding wild-type herpes virus genome). In some embodiments, the recombinant herpes virus genome is replication competent. In some embodiments, the recombinant herpes virus genome is replication defective.

In some embodiments, the recombinant nucleic acid is a recombinant herpes simplex virus (HSV) genome. In some embodiments, the recombinant herpes simplex virus genome is a recombinant herpes simplex virus type 1 (HSV-1) genome, a recombinant herpes simplex virus type 2 (HSV-2) genome, or any derivatives thereof. In some embodiments, the recombinant herpes simplex virus genome comprises one or more (e.g., one or more, two or more, three or more, four or more, five or more, six or more, seven or more, eight or more, nine or more, ten or more, etc.) inactivating mutations. In some embodiments, the one or more inactivating mutations are in one or more (e.g., one or more, two or more, three or more, four or more, five or more, six or more, seven or more, eight or more, nine or more, ten or more, etc.) herpes simplex virus genes. In some embodiments, the recombinant herpes simplex virus genome is attenuated (e.g., as compared to a corresponding, wild-type herpes simplex virus genome). In some embodiments, the recombinant herpes simplex virus genome is replication competent. In some embodiments, the recombinant herpes simplex virus genome is replication defective.

In some embodiments, the recombinant herpes simplex virus genome is a recombinant HSV-1 genome. In some embodiments, the recombinant HSV-1 genome may be from any HSV-1 strain known in the art, including, for example, strains 17, Ty25, R62, S25, Ku86, S23, R11, Ty148, Ku47, H166syn, 1319-2005, F-13, M-12, 90237, F-17, KOS, 3083-2008, F12g, L2, CD38, H193, M-15, India 2011, 0116209, F-11I, 66-207, 2762, 369-2007, 3355, MacIntyre, McKrae, 7862, 7-hse, HF10, 1394, 2005, 270-2007, OD4, SC16, M-19, 4J1037, 5J1060, J1060, KOS79, 132-1988, 160-1982, H166, 2158-2007, RE, 78326, F18g, F11, 172-2010, H129, F, E4, CJ994, F14g, E03, E22, E10, E06, E11, E25, E23, E35, E15, E07, E12, E14, E08, E19, E13, ATCC 2011, etc. (see e.g., Bowen et al. J Virol. 2019 Apr. 3; 93(8)). In some embodiments, the recombinant HSV-1 genome is from the KOS strain. In some embodiments, the recombinant HSV-1 genome is not from the McKrae strain. In some embodiments, the recombinant HSV-1 genome is attenuated. In some embodiments, the recombinant HSV-1 genome is replication competent. In some embodiments, the recombinant HSV-1 genome is replication defective. In some embodiments, the recombinant HSV-1 genome comprises one or more (e.g., one or more, two or more, three or more, four or more, five or more, six or more, seven or more, eight or more, nine or more, ten or more, etc.) inactivating mutations. In some embodiments, the one or more inactivating mutations are in one or more (e.g., one or more, two or more, three or more, four or more, five or more, six or more, seven or more, eight or more, nine or more, ten or more, etc.) HSV-1 genes.

In some embodiments, the recombinant herpes simplex virus genome comprises an inactivating mutation in at least one, at least two, at least three, at least four, at least five, at least six, at least seven, or all eight of the Infected Cell Protein (ICP) 0 (one or both copies), ICP4 (one or both copies), ICP22, ICP27, ICP47, thymidine kinase (tk), Long Unique Region (UL) 41 and/or UL55 herpes simplex virus genes. In some embodiments, the recombinant herpes simplex virus genome does not comprise an inactivating mutation in (e.g., is capable of expressing) the ICP0 (one or both copies) herpes simplex virus gene. In some embodiments, the recombinant herpes simplex virus genome does not comprise an inactivating mutation in (e.g., is capable of expressing) in the ICP27 herpes simplex virus gene. In some embodiments, the recombinant herpes simplex virus genome does not comprise an inactivating mutation in (e.g., is capable of expressing) the ICP47 herpes simplex virus gene. In some embodiments, the recombinant herpes simplex virus genome does not comprise an inactivating mutation in (e.g., is capable of expressing) the ICP0 (one or both copies), ICP27, and/or ICP47 herpes simplex virus genes. In some embodiments, the recombinant herpes simplex virus genome does not comprise an inactivating mutation in the Joint region. In some embodiments, the recombinant herpes simplex virus genome does not comprise an inactivating mutation in the ICP34.5 (one or both copies) and/or ICP47 herpes simplex virus genes (e.g., to avoid production of an immune-stimulating virus). In some embodiments, the recombinant herpes simplex virus genome does not comprise an inactivating mutation in the ICP34.5 herpes simplex virus gene (one or both copies). In some embodiments, the recombinant herpes simplex virus genome does not comprise an inactivating mutation in the ICP47 herpes simplex virus gene. In some embodiments, the recombinant herpes simplex virus genome does not comprise an inactivating mutation in the ICP34.5 (one or both copies) and ICP47 herpes simplex virus genes. In some embodiments, the recombinant herpes simplex virus genome is not oncolytic.

In some embodiments, the recombinant herpes simplex virus genome comprises an inactivating mutation in the ICP0 gene (one or both copies). In some embodiments, the recombinant herpes simplex virus genome comprises an inactivating mutation in the ICP0 gene (one or both copies), and further comprises an inactivating mutation in the ICP4 (one or both copies), ICP22, ICP27, ICP47, UL41, and/or UL55 genes. In some embodiments, the recombinant herpes simplex virus genome comprises an inactivating mutation in the ICP0 gene (one or both copies), and an inactivating mutation in the ICP4 gene (one or both copies). In some embodiments, the recombinant herpes simplex virus genome comprises an inactivating mutation in the ICP0 gene (one or both copies), and an inactivating mutation in the ICP22 gene. In some embodiments, the recombinant herpes simplex virus genome comprises an inactivating mutation in the ICP0 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), and an inactivating mutation in the ICP22 gene. In some embodiments, the recombinant herpes simplex virus genome comprises an inactivating mutation in the ICP0 gene (one or both copies), an inactivating mutation in the ICP4 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP22 gene, and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP0 (one or both copies), ICP4 (one or both copies), ICP22, and/or UL41 genes. In some embodiments, the recombinant herpes simplex virus genome further comprises an inactivating mutation in the ICP27, ICP47, and/or UL55 genes.

In some embodiments, the recombinant herpes simplex virus genome comprises an inactivating mutation in the ICP4 gene (one or both copies). In some embodiments, the recombinant herpes simplex virus genome comprises an inactivating mutation in the ICP4 gene (one or both copies), and further comprises an inactivating mutation in the ICP0 (one or both copies), ICP22, ICP27, ICP47, UL41, and/or UL55 genes. In some embodiments, the recombinant herpes simplex virus genome comprises an inactivating mutation in the ICP4 gene (one or both copies), and an inactivating mutation in the ICP22 gene. In some embodiments, the recombinant herpes simplex virus genome comprises an inactivating mutation in the ICP4 gene (one or both copies), and an inactivating mutation in the UL41 gene. In some embodiments, the recombinant herpes simplex virus genome comprises an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP4 (one or both copies), ICP22, and/or UL41 genes. In some embodiments, the recombinant herpes simplex virus genome further comprises an inactivating mutation in the ICP0 (one or both copies), ICP27, ICP47, and/or UL55 genes.

In some embodiments, the recombinant herpes simplex virus genome comprises an inactivating mutation in the ICP22 gene. In some embodiments, the recombinant herpes simplex virus genome comprises an inactivating mutation in the ICP22 gene, and further comprises an inactivating mutation in the ICP0 (one or both copies), ICP4 (one or both copies), ICP27, ICP47, UL41, and/or UL55 genes. In some embodiments, the recombinant herpes simplex virus genome comprises an inactivating mutation in the ICP22 gene, and an inactivating mutation UL41 gene. In some embodiments, the inactivating mutation is a deletion of the coding sequence of the ICP22 and/or UL41 genes. In some embodiments, the recombinant herpes simplex virus genome further comprises an inactivating mutation in the ICP0 (one or both copies), ICP4 (one or both copies), ICP27, ICP47, and/or UL55 genes.

In some embodiments, the recombinant herpes simplex virus genome comprises an inactivating mutation in the ICP27 gene. In some embodiments, the recombinant herpes simplex virus genome comprises an inactivating mutation in the ICP27 gene, and further comprises an inactivating mutation in the ICP0 (one or both copies), ICP4 (one or both copies), ICP22, ICP47, UL41, and/or UL55 genes. In some embodiments, the inactivating mutation is a deletion of the coding sequence of the ICP27 gene.

In some embodiments, the recombinant herpes simplex virus genome comprises an inactivating mutation in the ICP47 gene. In some embodiments, the recombinant herpes simplex virus genome comprises an inactivating mutation in the ICP47 gene, and further comprises an inactivating mutation in the ICP0 (one or both copies), ICP4 (one or both copies), ICP22, ICP27, UL41, and/or UL55 genes. In some embodiments, the inactivating mutation is a deletion of the coding sequence of the ICP47 gene.

In some embodiments, the recombinant herpes simplex virus genome comprises an inactivating mutation in the UL41 gene. In some embodiments, the recombinant herpes simplex virus genome comprises an inactivating mutation in the UL41 gene, and further comprises an inactivating mutation in the ICP0 (one or both copies), ICP4 (one or both copies), ICP22, ICP27, ICP47, and/or UL55 genes. In some embodiments, the inactivating mutation is a deletion of the coding sequence of the UL41 gene.

In some embodiments, the recombinant herpes simplex virus genome comprises an inactivating mutation in the UL55 gene. In some embodiments, the recombinant herpes simplex virus genome comprises an inactivating mutation in the UL55 gene, and further comprises an inactivating mutation in the ICP0 (one or both copies), ICP4 (one or both copies), ICP22, ICP27, ICP47, and/or UL41 genes. In some embodiments, the inactivating mutation is a deletion of the coding sequence of the UL55 gene.

In some embodiments, the recombinant herpes simplex virus genome comprises an inactivating mutation in (e.g., a deletion of) the internal repeat (Joint) region comprising the internal repeat long ($IR_L$) and internal repeat short ($IR_S$) regions. In some embodiments, inactivation (e.g., deletion) of the Joint region eliminates one copy each of the ICP4 and ICP0 genes. In some embodiments, inactivation (e.g., deletion) of the Joint region further inactivates (e.g., deletes) the promoter for the ICP22 and ICP47 genes. If desired, expression of one or both of these genes can be restored by insertion of an immediate early promoter into the recombinant herpes simplex virus genome (see e.g., Hill et al. (1995). Nature 375(6530): 411-415; Goldsmith et al. (1998). J Exp Med 187(3): 341-348). Without wishing to be bound by theory, it is believed that inactivating (e.g., deleting) the Joint region may contribute to the stability of the recombinant herpes simplex virus genome and/or allow for the recombinant herpes simplex virus genome to accommodate more and/or larger transgenes.

In some embodiments, the recombinant herpes simplex virus genome comprises an inactivating mutation in the ICP4 (one or both copies), ICP22, and ICP27 genes. In some embodiments, the recombinant herpes simplex virus genome comprises an inactivating mutation in the ICP4 (one or both copies), ICP27, and UL55 genes. In some embodiments, the recombinant herpes simplex virus genome comprises an inactivating mutation in the ICP4 (one or both copies), ICP22, ICP27, ICP47, and UL55 genes. In some embodiments, the inactivating mutation in the ICP4 (one or both copies), ICP27, and/or UL55 genes is a deletion of the coding sequence of the ICP4 (one or both copies), ICP27, and/or UL55 genes. In some embodiments, the inactivating mutation in the ICP22 and ICP47 genes is a deletion in the promoter region of the ICP22 and ICP47 genes (e.g., the ICP22 and ICP47 coding sequences are intact but are not transcriptionally active). In some embodiments, the recombinant herpes simplex virus genome comprises a deletion in the coding sequence of the ICP4 (one or both copies), ICP27, and UL55 genes, and a deletion in the promoter region of the ICP22 and ICP47 genes. In some embodiments, the recombinant herpes simplex virus genome further comprises an inactivating mutation in the ICP0 (one or both copies) and/or UL41 genes.

In some embodiments, the recombinant herpes simplex virus genome comprises an inactivating mutation in the ICP0 (one or both copies) and ICP4 (one or both copies) genes. In some embodiments, the recombinant herpes simplex virus genome comprises an inactivating mutation in the ICP0 (one or both copies), ICP4 (one or both copies), and ICP22 genes. In some embodiments, the recombinant herpes simplex virus genome comprises an inactivating mutation in the ICP0 (one or both copies), ICP4 (one or both copies), ICP22, and ICP27 genes. In some embodiments, the recombinant herpes simplex virus genome comprises an inactivating mutation in the ICP0 (one or both copies), ICP4 (one or both copies), ICP22, ICP27 and UL55 genes. In some embodiments, the inactivating mutation in the ICP0 (one or both copies), ICP4 (one or both copies), ICP22, ICP27 and/or UL55 genes comprises a deletion of the coding sequence of the ICP0 (one or both copies), ICP4 (one or both copies), ICP22, ICP27 and/or UL55 genes. In some embodiments, the recombinant herpes simplex virus genome further comprises an inactivating mutation in the ICP47 and/or the UL41 genes.

In some embodiments, a recombinant herpes simplex virus genome comprises one or more polynucleotides of the present disclosure within one, two, three, four, five, six, seven or more viral gene loci. Examples of suitable viral loci may include, without limitation, the ICP0 (one or both copies), ICP4 (one or both copies), ICP22, ICP27, ICP47, tk, UL41 and/or UL55 herpes simplex viral gene loci. In some embodiments, a recombinant herpes simplex virus genome comprises one or more polynucleotides of the present disclosure within one or both of the viral ICP4 gene loci (e.g., a recombinant virus carrying a polynucleotide encoding a human CFTR polypeptide in one or both of the ICP4 loci). In some embodiments, a recombinant herpes simplex virus genome comprises one or more polynucleotides of the present disclosure within the viral ICP22 gene locus (e.g., a recombinant virus carrying a polynucleotide encoding a human CFTR polypeptide in the ICP22 locus). In some embodiments, a recombinant herpes simplex virus genome comprises one or more polynucleotides of the present disclosure within the viral UL41 gene locus (e.g., a recombinant virus carrying a polynucleotide encoding a human CFTR polypeptide in the UL41 locus). In some embodiments, a recombinant herpes simplex virus genome comprises one or more polynucleotides of the present disclosure within one or both of the viral ICP0 gene loci (e.g., a recombinant virus carrying a polynucleotide encoding a human CFTR polypeptide in one or both of the ICP0 loci). In some embodiments, a recombinant herpes simplex virus genome comprises one or more polynucleotides of the present disclosure within the viral ICP27 gene locus (e.g., a recombinant virus carrying a polynucleotide encoding a human CFTR polypeptide in the ICP27 locus). In some embodiments, a recombinant herpes simplex virus genome comprises one or more polynucleotides of the present disclosure within the viral ICP47 gene locus (e.g., a recombinant virus carrying a polynucleotide encoding a human CFTR polypeptide in the ICP47 locus). In some embodiments, a recombinant herpes simplex virus genome comprises one or more polynucleotides of the present disclosure within one or both of the viral ICP4 gene loci, and one or more polynucleotides of the present disclosure within the viral ICP22 gene locus (e.g., a recombinant virus carrying a polynucleotide encoding a human CFTR polypeptide in one or both of the ICP4 loci, and a polynucleotide encoding a human CFTR polypeptide in the ICP22 locus). In some embodiments, a recombinant herpes simplex virus genome comprises one or more polynucleotides of the present disclosure within one or both of the viral ICP4 gene loci, and one or more polynucleotides of the present disclosure within the viral UL41 gene locus (e.g., a recombinant virus carrying a polynucleotide encoding a human CFTR polypeptide in one or both of the ICP4 loci, and a polynucleotide encoding a human CFTR polypeptide in the UL41 locus). In some embodiments, a recombinant herpes simplex virus genome comprises one or more polynucleotides of the present disclosure within the viral ICP22 gene locus, and one or more polynucleotides of the present disclosure within the viral UL41 gene locus (e.g., a recombinant virus carrying a polynucleotide encoding a human CFTR polypeptide in the ICP22 locus, and a polynucleotide encoding a human CFTR polypeptide in the UL41 locus). In some embodiments, a recombinant herpes simplex virus genome comprises one or more polynucleotides of the present disclosure within one or both of the viral ICP4 gene loci, one or more polynucleotides of the present disclosure within the viral ICP22 gene locus, and one or more polynucleotides of the present disclosure within the viral UL41 gene locus (e.g., a recombinant virus carrying a polynucleotide encoding a human CFTR polypeptide in one or both of the ICP4 loci, a polynucleotide encoding a human CFTR polypeptide in the ICP22 locus, and a polynucleotide encoding a human CFTR polypeptide in the UL41 locus). In some embodiments, a recombinant herpes simplex virus genome comprises one or more polynucleotides of the present disclosure within one or both of the viral ICP4 gene loci, one or more polynucleotides of the present disclosure within the viral ICP22 gene locus, one or more polynucleotides of the present disclosure within the viral UL41 gene locus, one or more polynucleotides of the present disclosure within one or both of the viral ICP0 gene loci, one or more polynucleotides of the present disclosure within the viral ICP27 gene locus, and/or one or more polynucleotides of the present disclosure within the viral ICP47 gene locus.

In some embodiments, the recombinant herpes virus genome (e.g., a recombinant herpes simplex virus genome) has been engineered to decrease or eliminate expression of one or more herpes virus genes (e.g., one or more toxic herpes virus genes), such as one or both copies of the HSV ICP0 gene, one or both copies of the HSV ICP4 gene, the HSV ICP22 gene, the HSV UL41 gene, the HSV ICP27 gene, the HSV ICP47 gene, etc. In some embodiments, the recombinant herpes virus genome (e.g., a recombinant herpes simplex virus genome) has been engineered to reduce cytotoxicity of the recombinant genome (e.g., when introduced into a target cell) as compared to a corresponding wild-type herpes virus genome. In some embodiments, the target cell is a human cell (primary cells or a cell line derived therefrom). In some embodiments, the target cell is a cell of the mucosa. In some embodiments, the target cell is a cell of the respiratory tract (primary cells or a cell line derived therefrom). In some embodiments, the target cell is an airway epithelial cell (primary cells or a cell line derived therefrom). In some embodiments, the target cell is a cell of the lung (primary cells or a cell line derived therefrom). In some embodiments, cytotoxicity of the recombinant herpes virus genome is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% as compared to a corresponding wild-type herpes virus genome (e.g., measuring the relative cytotoxicity of a recombinant ΔICP4 (one or both copies) herpes simplex virus genome vs. a wild-type herpes simplex virus genome in a target cell; measuring the relative cytotoxicity of a recombinant ΔICP4 (one or both copies)/ΔICP22 herpes simplex virus genome vs. a wild-type herpes simplex virus genome in a target cell, etc.). In some embodiments, cytotoxicity of the recombinant herpes virus genome is reduced by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more as compared to a corresponding wild-type herpes virus genome (e.g., measuring the relative cytotoxicity of a recombinant ΔICP4 (one or both copies) herpes simplex virus genome vs. a wild-type herpes simplex virus genome in a target cell; measuring the relative cytotoxicity of a recombinant ΔICP4 (one or both copies)/ΔICP22 herpes simplex virus genome vs. a wild-type herpes simplex virus genome in a target cell, etc.). Methods of measuring cytotoxicity are known to one of ordinary skill in the art, including, for example, through the use of vital dyes (formazan dyes), protease biomarkers, an MTT assay (or an assay using related tetrazolium salts such as XTT, MTS, water-soluble tetrazolium salts, etc.), measuring ATP content, etc.

In some embodiments, the recombinant herpes virus genome (e.g., a recombinant herpes simplex virus genome) has been engineered to reduce its impact on target cell proliferation after exposure of a target cell to the recombinant genome, as compared to a corresponding wild-type herpes virus genome. In some embodiments, the target cell is a human cell (primary cells or a cell line derived therefrom). In some embodiments, the target cell is a cell of the mucosa. In some embodiments, the target cell is a cell of the respiratory tract (primary cells or a cell line derived therefrom). In some embodiments, the target cell is an airway epithelial cell (primary cells or a cell line derived therefrom). In some embodiments, the target cell is a cell of the lung (primary cells or a cell line derived therefrom). In some embodiments, target cell proliferation after exposure to the recombinant genome is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% faster as compared to target cell proliferation after exposure to a corresponding wild-type herpes virus genome (e.g., measuring the relative cellular proliferation after exposure to a recombinant ΔICP4 (one or both copies) herpes simplex virus genome vs. cellular proliferation after exposure to a wild-type herpes simplex virus genome in a target cell; measuring the relative cellular proliferation after exposure to a recombinant ΔICP4 (one or both copies)/ΔICP22 herpes simplex virus genome vs. a wild-type herpes simplex virus genome in a target cell, etc.). In some embodiments, target cell proliferation after exposure to the recombinant genome is at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, or at least about 1000-fold faster as compared to target cell proliferation after exposure to a corresponding wild-type herpes virus genome (e.g., measuring the relative cellular proliferation after exposure to a recombinant ΔICP4 (one or both copies) herpes simplex virus genome vs. cellular proliferation after exposure to a wild-type herpes simplex virus genome in a target cell; measuring the relative cellular proliferation after exposure to a recombinant ΔICP4 (one or both copies)/ΔICP22 herpes simplex virus genome vs. a wild-type herpes simplex virus genome in a target cell, etc.). Methods of measuring cellular proliferation are known to one of ordinary skill in the art, including, for example, through the use of a Ki67 cell proliferation assay, a BrdU cell proliferation assay, etc.

A vector (e.g., herpes viral vector) may include one or more polynucleotides of the present disclosure in a form suitable for expression of the polynucleotide in a host cell. Vectors may include one or more regulatory sequences operatively linked to the polynucleotide to be expressed (e.g., as described above).

In some embodiments, a recombinant nucleic acid (e.g., a recombinant herpes simplex virus genome) of the present disclosure comprises one or more of the polynucleotides described herein inserted in any orientation in the recombinant nucleic acid. If the recombinant nucleic acid comprises two or more polynucleotides described herein (e.g., two or more, three or more, etc.), the polynucleotides may be inserted in the same orientation or opposite orientations to one another. Without wishing to be bound be theory, incorporating two polynucleotides (e.g., two transgenes) into a recombinant nucleic acid (e.g., a vector) in an antisense orientation may help to avoid read-through and ensure proper expression of each polynucleotide.

IV. Viruses

Certain aspects of the present disclosure relate to viruses comprising any of the polynucleotides and/or recombinant nucleic acids described herein. In some embodiments, the virus is capable of infecting one or more target cells of a subject (e.g., a human). In some embodiments, the virus is suitable for delivering the polynucleotides and/or recombinant nucleic acids into one or more target cells of a subject (e.g., a human). In some embodiments, the one or more target cells are human cells. In some embodiments, the one or more target cells are one or more cells with a CFTR deficiency (e.g., one or more cells comprising a genomic mutation in native CFTR gene). In some embodiments, the one or more target cells are one or more cells of the mucosa. In some embodiments, the one or more target cells are one or more airway epithelial cells. In some embodiments, the one or more target cells are one or more cells of the respiratory tract (e.g., airway epithelial cells (such as goblet cells, ciliated cells, Clara cells, neuroendocrine cells, basal cells, intermediate or parabasal cells, Serous cells, brush cells, oncocytes, non-ciliated columnar cells, and/or metaplastic cells); alveolar cells (such as type 1 pneumocytes, type 2 pneumocytes, and/or cuboidal non-ciliated cells); salivary gland cells in bronchi (such as Serous cells, mucous cells, and/or ductal cells); etc.). In some embodiments, the one or more target cells are one or more cells of the lung.

Any suitable virus known in the art may be used, including, for example, adenovirus, adeno-associated virus, retrovirus, lentivirus, sendai virus, herpes virus, vaccinia virus, and/or any hybrid or derivative viruses thereof. In some embodiments, the virus is attenuated. In some embodiments, the virus is replication competent. In some embodiments, the virus is replication defective. In some embodiments, the virus has been modified to alter its tissue tropism relative to the tissue tropism of a corresponding unmodified, wild-type virus. In some embodiments, the virus has reduced cytotoxicity (e.g., in a target cell) as compared to a corresponding wild-type virus. Methods of producing a virus comprising recombinant nucleic acids are well known to one of ordinary skill in the art.

In some embodiments, the virus is a member of the Herpesviridae family of DNA viruses, including, for example, a herpes simplex virus, a varicella zoster virus, a human cytomegalovirus, a herpesvirus 6A, a herpesvirus 6B, a herpesvirus 7, and a Kaposi's sarcoma-associated herpesvirus, etc. In some embodiments, the herpes virus is attenuated. In some embodiments, the herpes virus is replication defective. In some embodiments, the herpes virus is replication competent. In some embodiments, the herpes virus has been engineered to reduce or eliminate expression of one or more herpes virus genes (e.g., one or more toxic herpes virus genes). In some embodiments, the herpes virus has reduced cytotoxicity as compared to a corresponding wild-type herpes virus. In some embodiments, the herpes virus is not oncolytic.

In some embodiments, the herpes virus is a herpes simplex virus. Herpes simplex viruses comprising recombinant nucleic acids may be produced by a process disclosed, for example, in WO2015/009952, WO2017/176336, WO2019/200163, WO2019/210219, and/or WO2020/006486. In some embodiments, the herpes simplex virus is attenuated. In some embodiments, the herpes simplex virus is replication defective. In some embodiments, the herpes simplex virus is replication competent. In some embodiments, the herpes simplex virus has been engineered to reduce or eliminate expression of one or more herpes simplex virus genes (e.g., one or more toxic herpes simplex virus genes). In some embodiments, the herpes simplex virus has reduced cytotoxicity as compared to a corresponding wild-type herpes simplex virus. In some embodiments, the herpes simplex virus is not oncolytic. In some embodiments, the herpes simplex virus is an HSV-1 virus, an HSV-2, or any derivatives thereof. In some embodiments, the herpes simplex virus is an HSV-1 virus. In some embodiments, the herpes simplex virus is an HSV-1. In some embodiments, the HSV-1 is attenuated. In some embodiments, the HSV-1 is replication defective. In some embodiments, the HSV-1 is replication competent. In some embodiments, the HSV-1 has been engineered to reduce or eliminate expression of one or more HSV-1 genes (e.g., one or more toxic HSV-1 genes). In some embodiments, the HSV-1 has reduced cytotoxicity as compared to a corresponding wild-type HSV-1. In some embodiments, the HSV-1 is not oncolytic.

In some embodiments, the herpes simplex virus has been modified to alter its tissue tropism relative to the tissue tropism of an unmodified, wild-type herpes simplex virus. In some embodiments, the herpes simplex virus comprises a modified envelope. In some embodiments, the modified envelope comprises one or more (e.g., one or more, two or more, three or more, four or more, etc.) mutant herpes simplex virus glycoproteins. Examples of herpes simplex virus glycoproteins may include, but are not limited to, the glycoproteins gB, gC, gD, gH, and gL. In some embodiments, the modified envelope alters the herpes simplex virus tissue tropism relative to a wild-type herpes simplex virus.

In some embodiments, the transduction efficiency (in vitro and/or in vivo) of a virus of the present disclosure (e.g., a herpes virus) for one or more target cells (e.g., one or more cells of the respiratory tract) is at least about 25%. For example, the transduction efficiency of the virus for one or more target cells may be at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 99.5%, or more. In some embodiments, the virus is a herpes simplex virus and the transduction efficiency of the virus for one or more target cells (e.g., one or more cells of the respiratory tract) is about 85% to about 100%. In some embodiments, the virus is a herpes simplex virus and the transduction efficiency of the virus for one or more target cells (e.g., one or more cells of the respiratory tract) is at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100%. Methods of measuring viral transduction efficiency in vitro or in vivo are well known to one of ordinary skill in the art, including, for example, qPCR analysis, deep sequencing, western blotting, fluorometric analysis (such as fluorescent in situ hybridization (FISH), fluorescent reporter gene expression, immunofluorescence, FACS), etc.

V. Pharmaceutical Compositions and Formulations

Certain aspects of the present disclosure relate to pharmaceutical compositions or formulations comprising any of the recombinant nucleic acids (e.g., a recombinant herpes virus genome) and/or viruses (e.g., a herpes virus comprising a recombinant genome) described herein (such as a herpes simplex virus comprising a recombinant herpes simplex virus genome), and a pharmaceutically acceptable excipient or carrier.

In some embodiments, the pharmaceutical composition or formulation comprises any one or more of the viruses (e.g., herpes viruses) described herein. In some embodiments, the pharmaceutical composition or formulation comprises from about $10^4$ to about $10^{12}$ plaque forming units (PFU)/mL of the virus. For example, the pharmaceutical composition or formulation may comprise from about $10^4$ to about $10^{12}$, about $10^5$ to about $10^{12}$, about $10^6$ to about $10^{12}$, about $10^7$ to about $10^{12}$, about $10^8$ to about $10^{12}$, about $10^9$ to about $10^{12}$, about $10^{10}$ to about $10^{12}$, about $10^{11}$ to about $10^{12}$, about $10^4$ to about $10^{11}$, about $10^5$ to about $10^{11}$, about $10^6$ to about $10^{11}$, about $10^7$ to about $10^{11}$, about $10^8$ to about $10^{11}$, about $10^9$ to about $10^{11}$, about $10^{10}$ to about $10^{11}$, about $10^4$ to about $10^{10}$, about $10^5$ to about $10^{10}$, about $10^6$ to about $10^{10}$, about $10^7$ to about $10^{10}$, about $10^8$ to about $10^{10}$, about $10^9$ to about $10^{10}$, about $10^4$ to about $10^9$, about $10^5$ to about $10^9$, about $10^6$ to about $10^9$, about $10^7$ to about $10^9$, about $10^8$ to about $10^9$, about $10^4$ to about $10^8$, about $10^5$ to about $10^8$, about $10^6$ to about $10^8$, about $10^7$ to about $10^8$, about $10^4$ to about $10^7$, about $10^5$ to about $10^7$, about $10^6$ to about $10^7$, about $10^4$ to about $10^6$, about $10^5$ to about $10^6$, or about $10^4$ to about $10^5$ PFU/mL of the virus. In some embodiments, the pharmaceutical composition or formulation comprises about $10^4$, about $10^5$, about $10^6$, about $10^7$, about $10^8$, about $10^9$, about $10^{10}$, about $10^{11}$, or about $10^{12}$ PFU/mL of the virus.

Pharmaceutical compositions and formulations can be prepared by mixing the active ingredient(s) (such as a recombinant nucleic acid and/or a virus) having the desired degree of purity with one or more pharmaceutically acceptable carriers or excipients. Pharmaceutically acceptable carriers or excipients are generally nontoxic to recipients at the dosages and concentrations employed, and may include, but are not limited to: buffers (such as phosphate, citrate, acetate, and other organic acids); antioxidants (such as ascorbic acid and methionine); preservatives (such as octadecyldimethylbenzyl ammonium chloride, benzalkonium chloride, benzethonium chloride, phenol, butyl or benzyl alcohol, alkyl parabens, catechol, resorcinol, cyclohexanol, 3-pentanol, and m-cresol); amino acids (such as glycine, glutamine, asparagine, histidine, arginine, or lysine); low molecular weight (less than about 10 residues) polypeptides; proteins (such as serum albumin, gelatin, or immunoglobulins); polyols (such as glycerol, e.g., formulations including 10% glycerol); hydrophilic polymers (such as polyvinylpyrrolidone); monosaccharides, disaccharides, and other carbohydrates (including glucose, mannose, or dextrins); chelating agents (such as EDTA); sugars (such as sucrose, mannitol, trehalose, or sorbitol); salt-forming counter-ions (such as sodium); metal complexes (such as Zn-protein complexes); and/or non-ionic surfactants (such as polyethylene glycol (PEG)). A thorough discussion of pharmaceutically acceptable carriers is available in REMINGTON'S PHARMACEUTICAL SCIENCES (Mack Pub. Co., N.J. 1991).

In some embodiments, the pharmaceutical composition or formulation comprises one or more lipid (e.g., cationic lipid) carriers. In some embodiments, the pharmaceutical composition or formulation comprises one or more nanoparticle carriers. Nanoparticles are submicron (less than about 1000 nm) sized drug delivery vehicles that can carry encapsulated drugs (such as synthetic small molecules, proteins, peptides, cells, viruses, and nucleic acid-based biotherapeutics) for rapid or controlled release. A variety of molecules (e.g., proteins, peptides, recombinant nucleic acids, etc.) can be efficiently encapsulated in nanoparticles using processes well known in the art. In some embodiments, a molecule "encapsulated" in a nanoparticle may refer to a molecule (such as a virus) that is contained within the nanoparticle or attached to and/or associated with the surface of the nanoparticle, or any combination thereof. Nanoparticles for use in the compositions or formulations described herein may be any type of biocompatible nanoparticle known in the art, including, for example, nanoparticles comprising poly(lactic acid), poly(glycolic acid), PLGA, PLA, PGA, and any combinations thereof (see e.g., Vauthier et al. Adv Drug Del Rev. (2003) 55: 519-48; US2007/0148074; US2007/0092575; US2006/0246139; U.S. Pat. Nos. 5,753,234; 7,081,483; and WO2006/052285).

In some embodiments, the pharmaceutically acceptable carrier or excipient may be adapted for or suitable for any administration route known in the art, including, for example, intravenous, intramuscular, subcutaneous, cutaneous, oral, intranasal, intratracheal, sublingual, buccal, topical, transdermal, intradermal, intraperitoneal, intraorbital, intravitreal, subretinal, transmucosal, intraarticular, by implantation, by inhalation, intrathecal, intraventricular, and/or intranasal administration. In some embodiments, the pharmaceutically acceptable carrier or excipient is adapted for or suitable for oral, intranasal, intratracheal, and/or inhaled administration. In some embodiments, the pharmaceutically acceptable carrier or excipient is adapted for or suitable for inhaled administration. In some embodiments, the pharmaceutically acceptable carrier or excipient is adapted for or suitable for non-invasive inhaled administration. In some embodiments, the pharmaceutically acceptable carrier or excipient is adapted for or suitable for nebulization (e.g., using a vibrating mesh nebulizer).

In some embodiments, the pharmaceutical composition or formulation is adapted for or suitable for any administration route known in the art, including, for example, intravenous, intramuscular, subcutaneous, cutaneous, oral, intranasal, intratracheal, sublingual, buccal, topical, transdermal, intradermal, intraperitoneal, intraorbital, intravitreal, subretinal, transmucosal, intraarticular, by implantation, by inhalation, intrathecal, intraventricular, or intranasal administration. In some embodiments, the pharmaceutical composition or formulation is adapted for or suitable for oral, intranasal, intratracheal, or inhaled administration. In some embodiments, the pharmaceutical composition or formulation is adapted for or suitable for inhaled administration. In some embodiments, the pharmaceutical composition or formulation is adapted for or suitable for non-invasive inhaled administration. In some embodiments, the pharmaceutical composition or formulation is adapted for or suitable for nebulization (e.g., using a vibrating mesh nebulizer).

In some embodiments, the pharmaceutical composition or formulation further comprises one or more additional components. Examples of additional components may include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); wetting agents (e.g., sodium lauryl sulphate, etc.); salt solutions; alcohols; polyethylene glycols; gelatin; lactose; amylase; magnesium stearate; talc; silicic acid; viscous paraffin; hydroxymethylcellulose; polyvinylpyrrolidone; sweetenings; flavorings; perfuming agents; colorants; moisturizers; sunscreens; antibacterial agents; agents able to stabilize polynucleotides or prevent their degradation, and the like. In some embodiments, the pharmaceutical composition or formulation comprises a phosphate buffer. In some embodiments, the pharmaceutical composition or formulation comprises glycerol (e.g., at about 1%, about 2%, about 3%, about 4%, about 5%, about 6%, about 7%, about 8%, about 9%, about 10%, about 15%, etc.). In some embodiments, the pharmaceutical composition or formulation comprises a phosphate buffer and glycerol. In some embodiments, the pharmaceutical composition or formulation comprises less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, less than about 0.5%, or less than about 0.1% glycerol. In some embodiments, the pharmaceutical composition or formulation does not comprise glycerol.

Pharmaceutical compositions and formulations to be used for in vivo administration are generally sterile. Sterility may be readily accomplished, e.g., by filtration through sterile filtration membranes.

In some embodiments, any of the recombinant nucleic acids, viruses, and/or pharmaceutical compositions or formulations described herein may be used to deliver one or more polynucleotides encoding a CFTR polypeptide into one or more cells of a subject (e.g., one or more CFTR-deficient cells, one or more cells harboring a CFTR gene mutation, one or more cells of the respiratory tract, etc.). In some embodiments, any of the recombinant nucleic acids, viruses, and/or pharmaceutical compositions or formulations described herein may be used in the treatment of a disease or condition that would benefit from the expression of a CFTR polypeptide (e.g., a disease associated with a CFTR deficiency and/or a disease associated with a CFTR gene mutation). In some embodiments, any of the recombinant nucleic acids, viruses, and/or pharmaceutical compositions or formulations described herein may be used in the prevention or treatment of a chronic lung disease (such as cystic fibrosis, COPD, etc.). In some embodiments, any of the recombinant nucleic acids, viruses, and/or pharmaceutical compositions or formulations described herein may be used in the prevention or treatment of cystic fibrosis.

In some embodiments, any of the recombinant nucleic acids, viruses, and/or pharmaceutical compositions or formulations described herein may be used in the preparation of a medicament useful for delivering one or more polynucleotides encoding a CFTR polypeptide into one or more cells of a subject (e.g., one or more CFTR-deficient cells, one or more cells harboring a CFTR gene mutation, one or more cells of the respiratory tract, etc.). In some embodiments, any of the recombinant nucleic acids, viruses, and/or pharmaceutical compositions or formulations described herein may be used in the preparation of a medicament useful for the prevention or treatment of a disease or condition that would benefit from the expression of a CFTR polypeptide (e.g., a disease associated with a CFTR deficiency and/or a disease associated with a CFTR gene mutation). In some embodiments, any of the recombinant nucleic acids, viruses, and/or pharmaceutical compositions or formulations described herein may be used in the preparation of a medicament useful for the prevention or treatment of a chronic lung disease (such as cystic fibrosis, COPD, etc.). In some embodiments, any of the recombinant nucleic acids, viruses, and/or pharmaceutical compositions or formulations described herein may be used in the preparation of a medicament useful for the prevention or treatment of cystic fibrosis.

VI. Methods

Certain aspects of the present disclosure relate to enhancing, increasing, augmenting, and/or supplementing the levels of a CFTR polypeptide in one or more cells of a subject comprising administering to the subject any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation) in an endogenous CFTR gene (one or both copies). In some embodiments, the subject suffers from a chronic lung disease, e.g., cystic fibrosis, COPD, etc. In some embodiments, the subject suffers from cystic fibrosis.

In some embodiments, administration of the recombinant nucleic acid, virus, medicament, and/or pharmaceutical composition or formulation to the subject increases CFTR levels (transcript or protein levels) by at least about 2-fold in one or more contacted or treated cells of the subject, as compared to the endogenous levels of CFTR in one or more corresponding untreated cells in the subject. For example, administration of the recombinant nucleic acid, virus, medicament, and/or pharmaceutical composition or formulation may increase CFTR levels (transcript or protein levels) by at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more in one or more contacted or treated cells of the subject, as compared to the endogenous levels of CFTR in one or more corresponding untreated cells in the subject. In some embodiments, the one or more contacted or treated cells are one or more cells of the respiratory tract (e.g., one or more cells of the airway epithelia and/or one or more cells of the submucosal glands). Methods of measuring transcript or protein levels from a sample are well known to one of ordinary skill in the art, including, for example, qPCR, western blot, mass spectrometry, etc.

Other aspects of the present disclosure relate to a method of reducing cellular sodium levels in a subject in need thereof comprising administering to the subject any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation) in an endogenous CFTR gene (one or both copies). In some embodiments, the subject suffers from a chronic lung disease, e.g., cystic fibrosis, COPD, etc. In some embodiments, the subject suffers from cystic fibrosis.

In some embodiments, administration of the recombinant nucleic acid, virus, medicament, and/or pharmaceutical composition or formulation to the subject decreases intracellular sodium levels by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% or more in one or more contacted or treated cells, as compared to the intracellular sodium levels in one or more corresponding untreated cells in the subject. Methods of measuring intracellular sodium levels are generally known to one of ordinary skill in the art.

Other aspects of the present disclosure relate to a method of improving a measure of at least one respiratory volume in a subject in need thereof comprising administering to the subject any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation) in an endogenous CFTR gene (one or both copies). In some embodiments, the subject suffers from a chronic lung disease, e.g., cystic fibrosis, COPD, etc.

In some embodiments, administration of the recombinant nucleic acid, virus, medicament, and/or pharmaceutical composition or formulation to the subject improves a measure of at least one respiratory volume by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% or more as compared to at least one reference respiratory volume measured in the subject prior to treatment. Examples of suitable respiratory volumes that may be measured include, for example: Total Lung Capacity (TLC), the volume in the lungs at maximal inflation; Tidal Volume (TV), the volume of air moved into or out of the lungs during quiet breathing; Residual Volume (RV), the volume of air remaining in the lungs after a maximal exhalation; Expiratory Reserve Volume (ERV), the maximal volume of air that can be exhaled (above tidal volume) during a forceful breath out; Inspiratory Reserve Volume (ERV), the maximal volume of air that can be inhaled from the end-inspiratory position; Inspiratory Capacity (IC), the sum of IRV and TV; Inspiratory vital capacity (IVC), the maximum volume of air inhaled form the point of maximum expiration; Vital Capacity (VC), the volume of air breathed our after the deepest inhalation; Functional Residual Capacity (FRC), the volume in the lungs at the end-expiratory position; Forced vital capacity (FVC), the determination of the vital capacity from a maximally forced expiratory effort; Forced Expiratory Volume (time) (FEVt), the volume of air exhaled under forced conditions in the first t seconds; Forced Inspiratory Flow (FIF), a specific measurement of the forced inspiratory curve; Peak Expiratory Flow (PEF), the highest forced expiratory flow measured with a peak flow meter; Maximal Voluntary Ventilation (MVV), the volume of air expired in a specific period during repetitive maximal effort; etc. Methods of measuring respiratory volumes are generally known to one of ordinary skill in the art.

Other aspects of the present disclosure relate to a method of reducing or preventing chronic bacterial infections in the lungs of a subject in need thereof comprising administering to the subject any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation) in an endogenous CFTR gene (one or both copies). In some embodiments, the subject suffers from a chronic lung disease, e.g., cystic fibrosis, COPD, etc. In some embodiments, the subject suffers from cystic fibrosis. Direct and indirect methods of monitoring bacterial infections in the lungs, including improvements thereto, are known to one of ordinary skill in the art, including, for example, by performing: blood tests or cultures, oximetry, arterial blood gas measurements, bronchoscopy, transtracheal mucus cultures, lung biopsies, thoracentesis, computed tomography scans, etc.

Other aspects of the present disclosure relate to a method of reducing, preventing, or treating chronic inflammation of the lungs of a subject in need thereof comprising administering to the subject any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation) in an endogenous CFTR gene (one or both copies). In some embodiments, the subject suffers from a chronic lung disease, e.g., cystic fibrosis, COPD, etc. In some embodiments, the subject suffers from cystic fibrosis. Methods of measuring lung inflammation, including improvements thereto, are well known to one of ordinary skill in the art, including, for example, by measuring exhaled nitric oxide, determining the percentage of eosinophils in the sputum and/or blood, etc.

Other aspects of the present disclosure relate to a method of reducing, inhibiting, or treating progressive lung destruction in a subject in need thereof comprising administering to the subject any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation) in an endogenous CFTR gene (one or both copies). In some embodiments, the subject suffers from a chronic lung disease, e.g., cystic fibrosis, COPD, etc. In some embodiments, the subject suffers from cystic fibrosis. Methods of measuring lung destruction are well known to one of ordinary skill in the art, including, for example, by the methods described by Saetta et al. (Am Rev Respir Dis. 1985 May; 131(5): 764-9).

Other aspects of the present disclosure relate to a method of providing prophylactic, palliative, or therapeutic relief to one or more signs or symptoms of cystic fibrosis in a subject in need thereof comprising administering to the subject an effective amount of any of the recombinant nucleic acids, viruses, medicaments, and/or pharmaceutical compositions or formulations described herein. In some embodiments, the subject is a human. In some embodiments, the subject's genome comprises a mutation (e.g., a loss-of-function mutation) in an endogenous CFTR gene (one or both copies).

Signs and symptoms of cystic fibrosis may include, without limitation: persistent cough that produces thick mucus; thick sticky mucus that builds up in the airways; wheezing; breathlessness; sinusitis; repeated lung infections; inflamed nasal passages; bronchiectasis; nasal polyps; hemoptysis; pneumothorax; pancreatitis; recurring pneumonia; respiratory failure; and any combinations thereof.

Other aspects of the present disclosure relate to a method of providing prophylactic, palliative, or therapeutic relief to one or more signs or symptoms of COPD in a subject in need thereof comprising administering to the subject an effective amount of any of the recombinant nucleic acids, viruses, medicaments, and/or pharmaceutical compositions or formulations described herein. In some embodiments, the subject is a human. In some embodiments, the subject is a smoker or an ex-smoker.

Signs and symptoms of COPD may include, without limitation: shortness of breath; wheezing; chest tightness; excess mucus in the lungs; a chronic cough; cyanosis; frequent respiratory infections; and any combinations thereof.

The recombinant nucleic acids, viruses, medicaments, and/or pharmaceutical compositions or formulations described herein may be administered by any suitable method or route known in the art, including, without limitation, orally, intranasally, intratracheally, sublingually, buccally, topically, rectally, via inhalation, transdermally, subcutaneously, intradermally, intravenously, intraarterially, intramuscularly, intracardially, intraosseously, intraperitoneally, transmucosally, vaginally, intravitreally, intraorbitally, subretinally, intraarticularly, peri-articularly, locally, epicutaneously, or any combinations thereof. The present disclosure thus encompasses methods of delivering any of the recombinant nucleic acids, viruses, medicaments, or pharmaceutical compositions or formulations described herein to an individual (e.g., an individual having, or at risk of developing, a chronic lung disease such as cystic fibrosis).

In some embodiments, the recombinant nucleic acids, viruses, medicaments, and/or pharmaceutical compositions or formulations described herein are administered orally, intranasally, intratracheally, and/or via inhalation. Methods of delivering drugs to the lungs via oral, intranasal, intratracheal, and or inhaled routes of administration or generally known to one of ordinary skill in the art (see e.g., Gardenhire et al. A Guide to Aerosol Delivery Devices for Respiratory Therapists, $4^{th}$ Edition, American Association for Respiratory care, 2017; Patil et al. Pulmonary Drug Delivery Strategies: A Concise, Systematic Review, Lung India. 2012. 29(1):44-9; Marx et al. Intranasal Drug Administration—An Attractive Delivery Route for Some Drugs, 2015).

In some embodiments, the recombinant nucleic acids, viruses, medicaments, and/or pharmaceutical compositions or formulations are delivered to the lungs by inhalation of an aerosolized formulation. Inhalation may occur through the nose and/or the mouth of the subject. Exemplary devices for delivering the recombinant nucleic acids, viruses, medicaments, and/or pharmaceutical compositions or formulations to the lung may include, without limitation, dry powder inhalers, pressurized metered dose inhalers, soft mist inhalers, nebulizers (e.g., jet nebulizers, ultrasonic nebulizers, vibrating mesh nebulizers), colliding jets, extruded jets, surface wave microfluidic atomization, capillary aerosol generation, electrohydrodynamic aerosol devices, etc. (see e.g., Carvalho and McConville. The function and performance of aqueous devices for inhalation therapy. (2016) Journal of Pharmacy and Pharmacology.

Liquid formulations may be administered to the lungs of a subject, e.g., using a pressurized metered dose inhaler (pMDI). pMDIs generally include at least two components: a canister in which the liquid formulation is held under pressure in combination with one or more propellants, and a receptacle used to hold and actuate the canister. The canister may contain a single dose or multiple doses of the formulation. The canister may include a valve, typically a metering valve, from which the contents of the canister may be discharged. Aerosolized drug is dispensed from the pMDI by applying a force on the canister to push it into the receptacle, thereby opening the valve and causing the drug particles to be conveyed from the valve through the receptacle outlet. Upon discharge from the canister, the liquid formulation is atomized, forming an aerosol. pMDIs typically employ one or more propellants to pressurize the contents of the canister and to propel the liquid formulation out of the receptacle outlet, forming an aerosol. Any suitable propellants may be utilized, and may take a variety of forms, including, for example, a compressed gas or a liquified gas.

Liquid formulations may be administered to the lungs of a subject, e.g., using a nebulizer. Nebulizers are liquid aerosol generators that convert the liquid formulation into mists or clouds of small droplets, often having diameters less than about 5 microns mass median aerodynamic diameter, which can be inhaled into the lower respiratory tract. The droplets carry the active agent(s) into the nose, upper airways, and/or deep lungs when the aerosol cloud is inhaled. Any type of nebulizer known in the art may be used to administer the formulation to a patient, including, without limitation, pneumatic (jet) nebulizers, electromechanical nebulizers (e.g., ultrasonic nebulizers, vibrating mesh nebulizers, etc.), etc. Pneumatic (jet) nebulizers use a pressurized gas supply as a driving force for atomization of the liquid formulation. Compressed gas is delivered through a nozzle or jet to create a low-pressure field which entrains a surrounding liquid formulation and shears it into a thin film or filaments. The film or filaments are unstable and break up into small droplets that are carried by the compressed gas flow into the inspiratory breath. Baffles inserted into the droplet plume screen out the larger droplets and return them to the bulk liquid reservoir. Electromechanical nebulizers use electrically generated mechanical force to atomize liquid formulations. The electromechanical driving force can be applied, for example, by vibrating the liquid formulation at ultrasonic frequencies, or by forcing the bulk liquid through small holes in a thin film. The forces generate thin liquid films or filament streams which break up into small droplets to form a slow-moving aerosol stream which can be entrained in an inspiratory flow. In some embodiments, the nebulizer is a vibrating mesh nebulizer. Examples of vibrating mesh nebulizers include, for example, the Phillips InnoSpire, the Aerogen Solo, the PARI eFlow, etc.

Liquid formulations may be administered to the lungs of a subject, e.g., using an electrohydrodynamic (EHD) aerosol device. EHD aerosol devices use electrical energy to aerosolize liquid drug solutions or suspensions.

Dry powder formulations may be administered to the lungs of a subject, e.g., using a dry powder inhaler (DPI). DPIs typically use a mechanism such as a burst of gas to create a cloud of dry powder inside a container, which can then be inhaled by the subject. In a DPI, the dose to be administered is stored in the form of a non-pressurized dry powder and, upon actuation of the inhaler, the particles of the powder are inhaled by the subject. In some cases, a compressed gas may be used to dispense the powder, similar to pMDIs. In some cases, the DPI may be breath actuated (an aerosol is created in precise response to inspiration). Typically, dry powder inhalers administer a dose of less than a few tens of milligrams per inhalation to avoid provocation of cough. Examples of DPIs include, for example, the Turbohaler® inhaler (AstraZeneca), the Clickhaler® inhaler (Innovata), the Diskus® inhaler (Glaxo), the EasyHaler® (Orion), the Exubera® inhaler (Pfizer), etc.

In some embodiments, the recombinant nucleic acids, viruses, medicaments, and/or pharmaceutical compositions or formulations are administered once to the subject. In some embodiments, the recombinant nucleic acids, viruses, medicaments, and/or pharmaceutical compositions are administered at least twice (e.g., at least 2 times, at least 3 times, at least 4 times, at least 5 times, at least 10 times, etc.) to the subject. In some embodiments, at least about 1 hour (e.g., at least about 1 hour, at least about 6 hours, at least about 12 hours, at least about 18 hours, at least about 1 day, at least about 2 days, at least about 3 days, at least about 4 days, at least about 5 days, at least about 6 days, at least about 7 days, at least about 15 days, at least about 20 days, at least about 30 days, at least about 40 days, at least about 50 days, at least about 60 days, at least about 70 days, at least about 80 days, at least about 90 days, at least about 100 days, at least about 120 days, etc.) pass between administrations (e.g., between the first and second administrations, between the second and third administrations, etc.). In some embodiments, the recombinant nucleic acids, viruses, medicaments, and/or pharmaceutical compositions or formulations are administered one, two, three, four, five or more times per day to the subject. In some embodiments, the recombinant nucleic acids, viruses, medicaments, and/or pharmaceutical compositions or formulations are administered one, two, three, four, five or more times per month to the subject. In some embodiments, the recombinant nucleic acids, viruses, medicaments, and/or pharmaceutical compositions or formulations are administered one, two, three, four, five or more times per year to the subject.

VII. Host Cells

Certain aspects of the present disclosure relate to one or more host cells comprising any of the recombinant nucleic acids described herein. Any suitable host cell (prokaryotic or eukaryotic) known in the art may be used, including, for example: prokaryotic cells including eubacteria, such as Gram-negative or Gram-positive organisms, for example Enterobacteriaceae such as *Escherichia* (e.g., *E. coli*), *Enterobacter, Erminia, Klebsiella, Proteus, Salmonella* (e.g., *S. typhimurium*), *Serratia* (e.g., *S. marcescans*), and *Shigella*, as well as Bacilli such as *B. subtilis* and *B. licheniformis*; fungal cells (e.g., *S. cerevisiae*); insect cells (e.g., S2 cells, etc.); and mammalian cells, including monkey kidney CV1 line transformed by SV40 (COS-7, ATCC CRL 1651), human embryonic kidney line (293 or 293 cells subcloned for growth in suspension culture), baby hamster kidney cells (BHK, ATCC CCL 10), mouse Sertoli cells (TM4), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TRI cells, MRC 5 cells, FS4 cells, human hepatoma line (Hep G2), Chinese hamster ovary (CHO) cells, including DHFR" CHO cells, and myeloma cell lines such as NSO and Sp2/0. In some embodiments, the host cell is a human or non-human primate cell. In some embodiments, the host cells are cells from a cell line. Examples of suitable host cells or cell lines may include, but are not limited to, 293, HeLa, SH-Sy5y, Hep G2, CACO-2, A549, L929, 3T3, K562, CHO-K1, MDCK, HUVEC, Vero, N20, COS-7, PSN1, VCaP, CHO cells, and the like.

In some embodiments, the recombinant nucleic acid is a herpes simplex viral vector. In some embodiments, the recombinant nucleic acid is a herpes simplex virus amplicon. In some embodiments, the recombinant nucleic acid is an HSV-1 amplicon or HSV-1 hybrid amplicon. In some embodiments, a host cell comprising a helper virus is contacted with an HSV-1 amplicon or HSV-1 hybrid amplicon described herein, resulting in the production of a virus comprising one or more recombinant nucleic acids described herein. In some embodiments, the virus is collected from the supernatant of the contacted host cell. Methods of generating virus by contacting host cells comprising a helper virus with an HSV-1 amplicon or HSV-1 hybrid amplicon are known in the art.

In some embodiments, the host cell is a complementing host cell. In some embodiments, the complementing host cell expresses one or more genes that are inactivated in any of the viral vectors described herein. In some embodiments, the complementing host cell is contacted with a recombinant herpes virus genome (e.g., a recombinant herpes simplex virus genome) described herein. In some embodiments, contacting a complementing host cell with a recombinant herpes virus genome results in the production of a herpes virus comprising one or more recombinant nucleic acids described herein. In some embodiments, the virus is collected from the supernatant of the contacted host cell. Methods of generating virus by contacting complementing host cells with a recombinant herpes simplex virus are generally described in WO2015/009952, WO2017/176336, WO2019/200163, WO2019/210219, and/or WO2020/006486.

VIII. Articles of Manufacture or Kits

Certain aspects of the present disclosure relate to an article of manufacture or a kit comprising any of the recombinant nucleic acids, viruses, medicaments, and/or pharmaceutical compositions or formulations described herein. In some embodiments, the article of manufacture or kit comprises a package insert comprising instructions for administering the recombinant nucleic acid, virus, medicament, and/or pharmaceutical composition or formulation to treat a CFTR deficiency (e.g., in a subject harboring homozygous CFTR loss-of-function gene mutations) and/or to provide prophylactic, palliative, or therapeutic relief of a one or more signs or symptoms of a chronic lung disease (such as cystic fibrosis or COPD). In some embodiments, the article or manufacture or kit further comprises a device for administering (e.g., aerosolizing) the recombinant nucleic acid, virus, medicament, and/or pharmaceutical composition or formulation. In some embodiments, the device is a nebulizer (e.g., a vibrating mesh nebulizer).

Suitable containers for the recombinant nucleic acids, viruses, medicaments, and/or pharmaceutical compositions or formulations may include, for example, bottles, vials, bags, tubes, and syringes. The container may be formed from a variety of materials such as glass, plastic (such as polyvinyl chloride or polyolefin), or metal alloy (such as stainless steel or hastelloy). In some embodiments, the container comprises a label on, or associated with the container, wherein the label indicates directions for use. The article of manufacture or kit may further include other materials desirable from a commercial and user standpoint, including other buffers, diluents, filters, inhalers, nebulizers, intranasal administration devices, a package insert, and the like.

IX. Enumerated Embodiments

Embodiment 1 a recombinant herpes virus genome comprising one or more polynucleotide encoding a cystic fibrosis transmembrane conductance regulator (CFTR) polypeptide.

Embodiment 2 the recombinant herpes virus genome of embodiment 1, wherein the recombinant herpes virus genome is replication competent.

Embodiment 3 the recombinant herpes virus genome of embodiment 1, wherein the recombinant herpes virus genome is replication defective.

Embodiment 4 the recombinant herpes virus genome of any one of embodiments 1-3, wherein the recombinant herpes virus genome comprises the one or more polynucleotides encoding the CFTR polypeptide within one or more viral gene loci.

Embodiment 5 the recombinant herpes virus genome of any one of embodiments 1-4, wherein the recombinant herpes virus genome is selected from the group consisting of a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any derivatives thereof.

Embodiment 6 the recombinant herpes virus genome of any one of embodiments 1-5, wherein the CFTR polypeptide is a human CFTR polypeptide.

Embodiment 7 the recombinant herpes virus genome of any one of embodiments 1-6, wherein the CFTR polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 5 or SEQ ID NO: 6.

Embodiment 8 the recombinant herpes virus genome of any one of embodiments 1-7, wherein the CFTR polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 5.

Embodiment 9 the recombinant herpes virus genome of any one of embodiments 1-8, wherein the recombinant herpes virus genome is a recombinant herpes simplex virus genome.

Embodiment 10 the recombinant herpes virus genome of embodiment 9, wherein the recombinant herpes simplex virus genome is a recombinant type 1 herpes simplex virus (HSV-1) genome, a recombinant type 2 herpes simplex virus (HSV-2) genome, or any derivatives thereof.

Embodiment 11 the recombinant herpes virus genome of embodiment 9 or embodiment 10, wherein the recombinant herpes simplex virus genome is a recombinant HSV-1 genome.

Embodiment 12 the recombinant herpes virus genome of any one of embodiments 9-11, wherein the recombinant herpes simplex virus genome has been engineered to reduce or eliminate expression of one or more toxic herpes simplex virus genes.

Embodiment 13 the recombinant herpes virus genome of any one of embodiments 9-12, wherein the recombinant herpes simplex virus genome comprises an inactivating mutation.

Embodiment 14 the recombinant herpes virus genome of embodiment 13, wherein the inactivating mutation is in a herpes simplex virus gene.

Embodiment 15 the recombinant herpes virus genome of embodiment 14, wherein the inactivating mutation is a deletion of the coding sequence of the herpes simplex virus gene.

Embodiment 16 the recombinant herpes virus genome of embodiment 14 or embodiment 15, wherein the herpes simplex virus gene is selected from the group consisting of Infected Cell Protein (ICP) 0, ICP4, ICP22, ICP27, ICP47, thymidine kinase (tk), Long Unique Region (UL) 41, and UL55.

Embodiment 17 the recombinant herpes virus genome of embodiment 16, wherein the recombinant herpes simplex virus genome comprises an inactivating mutation in one or both copies of the ICP4 gene.

Embodiment 18 the recombinant herpes virus genome of embodiment 16 or embodiment 17, wherein the recombinant herpes simplex virus genome comprises an inactivating mutation in the ICP22 gene.

Embodiment 19 the recombinant herpes virus genome of any one of embodiments 16-18, wherein the recombinant herpes simplex virus genome comprises an inactivating mutation in the UL41 gene.

Embodiment 20 the recombinant herpes virus genome of any one of embodiment 16-19, wherein the recombinant herpes simplex virus genome comprises an inactivating mutation in one or both copies of the ICP0 gene.

Embodiment 21 the recombinant herpes virus genome of any one of embodiments 16-20, wherein the recombinant herpes simplex virus genome comprises an inactivating mutation in the ICP27 gene.

Embodiment 22 the recombinant herpes virus genome of any one of embodiments 16-21, wherein the recombinant herpes simplex virus genome comprises an inactivating mutation in the ICP47 gene.

Embodiment 23 the recombinant herpes virus genome of any one of embodiments 16-22, wherein the recombinant herpes simplex virus genome comprises an inactivating mutation in the UL55 gene.

Embodiment 24 the recombinant herpes virus genome of any one of embodiments 9-23, wherein the recombinant herpes simplex virus genome comprises the one or more polynucleotides encoding the CFTR polypeptide within one or both of the ICP4 viral gene loci.

Embodiment 25 the recombinant herpes virus genome of any one of embodiments 9-24, wherein the recombinant herpes simplex virus genome comprises the one or more polynucleotides encoding the CFTR polypeptide within the ICP22 viral gene locus.

Embodiment 26 the recombinant herpes virus genome of any one of embodiments 9-25, wherein the recombinant herpes simplex virus genome comprises the one or more polynucleotides encoding the CFTR polypeptide within the UL41 viral gene locus.

Embodiment 27 the recombinant herpes virus genome of any one of embodiments 9-26, wherein the recombinant herpes simplex virus genome comprises the one or more polynucleotides encoding the CFTR polypeptide within one or both of the ICP0 viral gene loci.

Embodiment 28 the recombinant herpes virus genome of any one of 9-27, wherein the recombinant herpes simplex virus genome comprises the one or more polynucleotides encoding the CFTR polypeptide within the ICP27 viral gene locus.

Embodiment 29 the recombinant herpes virus genome of any one of embodiments 9-28, wherein the recombinant herpes simplex virus genome comprises the one or more polynucleotides encoding the CFTR polypeptide within the ICP47 viral gene locus.

Embodiment 30 the recombinant herpes virus genome of any one of embodiments 9-29, wherein the recombinant herpes simplex virus genome comprises the one or more polynucleotides encoding the CFTR polypeptide within the UL55 viral gene locus.

Embodiment 31 the recombinant herpes virus genome of any one of embodiment 1-30, wherein the recombinant herpes virus genome has reduced cytotoxicity when introduced into a target cell as compared to a corresponding wild-type herpes virus genome.

Embodiment 32 the recombinant herpes virus genome of embodiment 31, wherein the target cell is a human cell.

Embodiment 33 the recombinant herpes virus genome of embodiment 31 or embodiment 32, wherein the target cell is an airway epithelial cell.

Embodiment 34 the recombinant herpes virus genome of embodiment 31 or embodiment 32, wherein the target cell is a cell of the respiratory tract.

Embodiment 35 a herpes virus comprising the recombinant herpes virus genome of any one of embodiments 1-34.

Embodiment 36 the herpes virus of embodiment 35, wherein the herpes virus is replication competent.

Embodiment 37 the herpes virus of embodiment 35, wherein the herpes virus is replication defective.

Embodiment 38 the herpes virus of any one of embodiments 35-37, wherein the herpes virus has reduced cytotoxicity as compared to a corresponding wild-type herpes virus.

Embodiment 39 the herpes virus of any one of embodiments 35-38, wherein the herpes virus is selected from the group consisting of a herpes simplex virus, a varicella zoster virus, a human cytomegalovirus, a herpesvirus 6A, a herpesvirus 6B, a herpesvirus 7, and a Kaposi's sarcoma-associated herpesvirus.

Embodiment 40 the herpes virus of any one of embodiments 35-39, wherein the herpes virus is a herpes simplex virus.

Embodiment 41 the herpes virus of embodiment 39 or embodiment 40, wherein the herpes simplex virus is a type 1 herpes simplex virus (HSV-1), a type 2 herpes simplex virus (HSV-2), or any derivatives thereof.

Embodiment 42 the herpes virus of any one of embodiments 39-41, wherein the herpes simplex virus is an HSV-1.

Embodiment 43 a pharmaceutical composition comprising the recombinant herpes virus genome of any one of embodiments 1-34 or the herpes virus of any one of embodiments 35-42 and a pharmaceutically acceptable excipient.

Embodiment 44 the pharmaceutical composition of embodiment 43, wherein the pharmaceutical composition is suitable for topical, transdermal, subcutaneous, intradermal, oral, intranasal, intratracheal, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, or epicutaneous administration.

Embodiment 45 the pharmaceutical composition of embodiment 43 or embodiment 44, wherein the pharmaceutical composition is suitable for oral, intranasal, intratracheal, or inhaled administration.

Embodiment 46 the pharmaceutical composition of any one of embodiments 43-45, wherein the pharmaceutical composition is suitable for inhaled administration.

Embodiment 47 the pharmaceutical composition of any one of embodiments 43-46, wherein the pharmaceutical composition is suitable for non-invasive inhaled administration.

Embodiment 48 the pharmaceutical composition of any one of embodiments 43-47, wherein the pharmaceutical composition is suitable for use in a dry powder inhaler, a pressurized metered dose inhaler, a soft mist inhaler, a nebulizer, an electrohydrodynamic aerosol device, or any combinations thereof.

Embodiment 49 the pharmaceutical composition of any one of embodiments 43-48 wherein the pharmaceutical composition is suitable for use in a nebulizer.

Embodiment 50 the pharmaceutical composition of embodiment 49, wherein the nebulizer is a vibrating mesh nebulizer.

Embodiment 51 the pharmaceutical composition of any one of embodiments 43-50, wherein the pharmaceutical composition comprises a phosphate buffer.

Embodiment 52 the pharmaceutical composition of any one of embodiments 43-51, wherein the pharmaceutical composition comprises glycerol.

Embodiment 53 the pharmaceutical composition of any one of embodiments 43-52, wherein the pharmaceutical composition comprises a lipid carrier.

Embodiment 54 the pharmaceutical composition of any one of embodiments 43-53, wherein the pharmaceutical composition comprises a nanoparticle carrier.

Embodiment 55 a method of enhancing, increasing, augmenting, and/or supplementing the levels of a CFTR polypeptide in one or more cells of a subject, the method comprising administering to the subject an effective amount of the herpes virus of any one of embodiments 35-42 or the pharmaceutical composition of any one of embodiments 43-54.

Embodiment 56 the method of embodiment 55, wherein the one or more cells are one or more cells of the respiratory tract.

Embodiment 57 the method of embodiment 55 or embodiment 56, wherein the one or more cells are one or more airway epithelial cells or one or more cells of the submucosal glands.

Embodiment 58 a method of reducing or inhibiting progressive lung destruction in a subject in need thereof, the method comprising administering to the subject an effective amount of the herpes virus of any one of embodiments 35-42 or the pharmaceutical composition of any one of embodiments 43-54.

Embodiment 59 the method of any one of embodiments 55-58, wherein the subject suffers from a chronic lung disease.

Embodiment 60 the method of embodiment 59, wherein the chronic lung disease is cystic fibrosis or chronic obstructive pulmonary disease (COPD).

Embodiment 61 a method of providing prophylactic, palliative, or therapeutic relief of one or more signs or symptoms of cystic fibrosis in a subject in need thereof, the method comprising administering to the subject an effective amount of the herpes virus of any one embodiments 35-42 or the pharmaceutical composition of any one of embodiments 43-54.

Embodiment 62 the method of embodiment 61, wherein the one or more signs or symptoms of cystic fibrosis are selected from the group consisting of a persistent cough that produces thick mucus, thick sticky mucus that builds up in the airways, wheezing, breathlessness, sinusitis, repeated lung infections, inflamed nasal passages, bronchiectasis, nasal polyps, hemoptysis, pneumothorax, pancreatitis, recurring pneumonia, respiratory failure, and any combinations thereof.

Embodiment 63 a method of providing prophylactic, palliative, or therapeutic relief of one or more signs or symptoms of COPD in a subject in need thereof, the method comprising administering to the subject an effective amount of the herpes virus of any one of embodiments 35-42 or the pharmaceutical composition of any one of embodiments 43-54.

Embodiment 64 the method of embodiment 63, wherein the one or more signs or symptoms of COPD are selected from the group consisting of shortness of breath, wheezing, chest tightness, excess mucus in the lungs, a chronic cough, cyanosis, frequent respiratory infections, and any combinations thereof.

Embodiment 65 the method of any one of embodiments 55-64, wherein the subject is a human.

Embodiment 66 the method of any one of embodiments 55-65, wherein the subject's genome comprises a loss-of-function mutation in a CFTR gene.

Embodiment 67 the method of any one of embodiments 55-66, wherein the herpes virus or pharmaceutical composition is administered orally, intranasally, intratracheally, or via inhalation to the subject.

Embodiment 68 the method of any one of embodiments 55-67, wherein the herpes virus or pharmaceutical composition is administered via inhalation to the subject.

Embodiment 69 the method of any one of embodiments 55-68, wherein the herpes virus or pharmaceutical composition is administered via non-invasive inhaled administration.

Embodiment 70 the method of any one of embodiments 55-69, wherein the herpes virus or pharmaceutical composition is administered using a dry powder inhaler, a pressurized metered dose inhaler, a soft mist inhaler, a nebulizer, or an electrohydrodynamic aerosol device.

Embodiment 71 the method of any one of embodiments 55-70, wherein the herpes virus or pharmaceutical composition is administered using a nebulizer.

Embodiment 72 the method of embodiment 71, wherein the nebulizer is a vibrating mesh nebulizer.

The specification is considered to be sufficient to enable one skilled in the art to practice the present disclosure. Various modifications of the present disclosure in addition to those shown and described herein will become apparent to those skilled in the art from the foregoing description and fall within the scope of the appended claims.

EXAMPLES

The present disclosure will be more fully understood by reference to the following examples. It should not, however, be construed as limiting the scope of the present disclosure. It is understood that the examples and embodiments described herein are for illustrative purposes only and that various modifications or changes in light thereof will be suggested to persons skilled in the art, and are to be included within the spirit and purview of this application and scope of the appended claims.

Figure 1D:
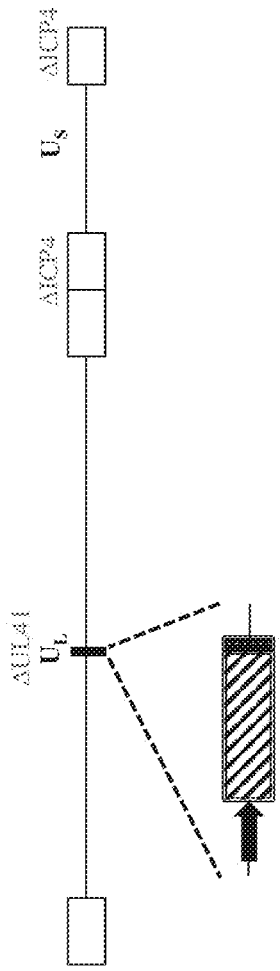
Figure 1E:
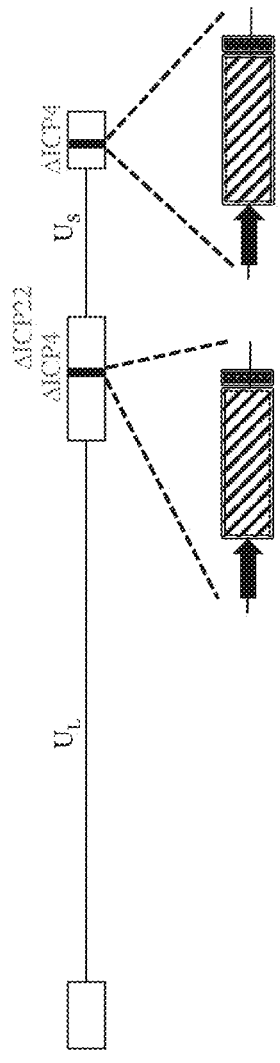
Figure 1F:
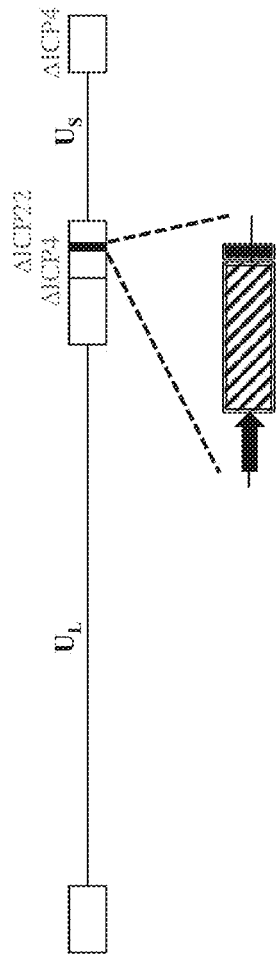
Figure 1I:
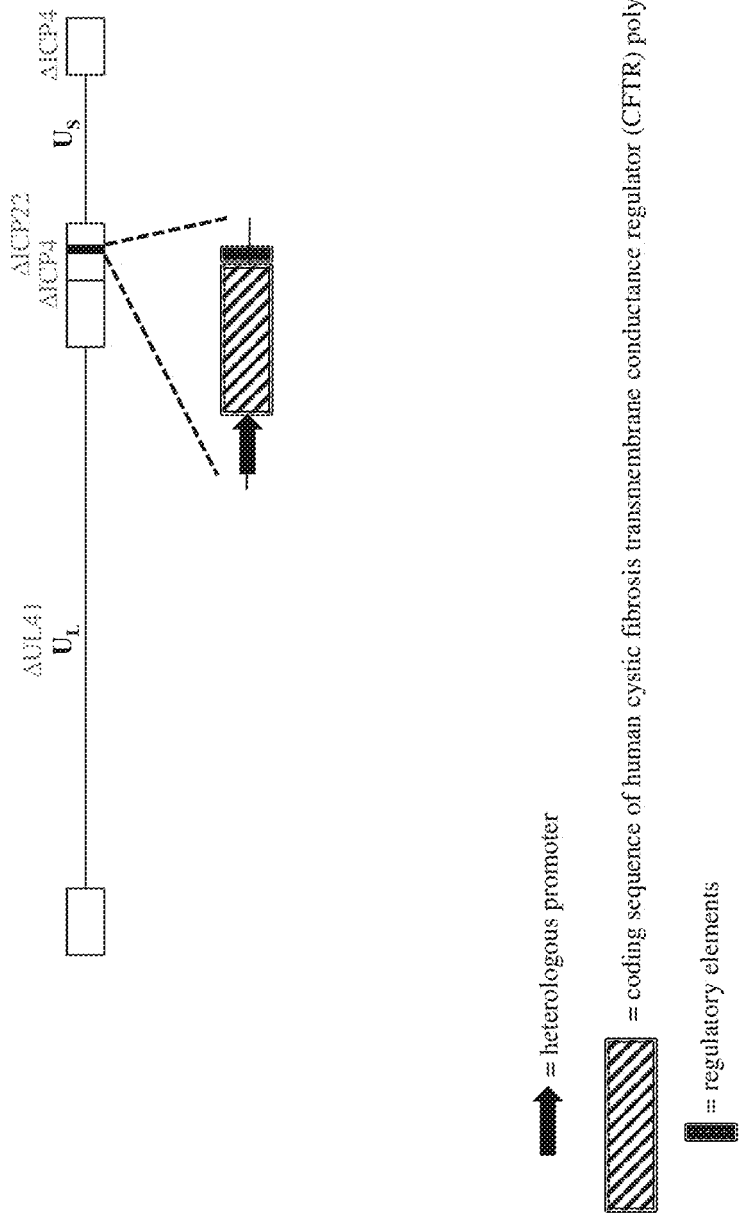

Example 1: Modified Herpes Simplex Virus Vectors Encoding a Human CFTR Protein To make modified herpes simplex virus genome vectors capable of expressing CFTR polypeptides in a target mammalian cell (such as cells of the lung), a herpes simplex virus genome (FIG. 1A) is first modified to inactivate one or more herpes simplex virus genes. Such modifications may decrease the toxicity of the genome in mammalian cells. Next, variants of these modified/attenuated recombinant viral constructs are generated such that they carry one or more polynucleotides encoding the desired CFTR polypeptide. These variants include: 1) a recombinant ΔICP4-modified HSV-1 genome comprising expression cassettes containing the coding sequence (e.g., SEQ ID NO: 2) of a human CFTR polypeptide (e.g., SEQ ID NO: 5) under the control of a heterologous promoter integrated at each ICP4 locus (FIG. 1B); 2) a recombinant ΔICP4/ΔUL41-modified HSV-1 genome comprising expression cassettes containing the coding sequence of a human CFTR polypeptide under the control of a heterologous promoter integrated at each ICP4 locus (FIG. 1C); 3) a recombinant ΔICP4/ΔUL41-modified HSV-1 genome comprising an expression cassette containing the coding sequence of a human CFTR polypeptide under the control of a heterologous promoter integrated at the UL41 locus (FIG. 1D); 4) a recombinant ΔICP4/ΔICP22-modified HSV-1 genome comprising expression cassettes containing the coding sequence of a human CFTR polypeptide under the control of a heterologous promoter integrated at each ICP4 locus (FIG. 1E); 5) a recombinant ΔICP4/ΔICP22-modified HSV-1 genome comprising an expression cassette containing the coding sequence of a human CFTR polypeptide under the control of a heterologous promoter integrated at the ICP22 locus (FIG. 1F); 6) a recombinant ΔICP4/ΔUL41/ΔICP22-modified HSV-1 genome comprising expression cassettes containing the coding sequence of a human CFTR polypeptide under the control of a heterologous promoter integrated at each ICP4 locus (FIG. 1G); 7) a recombinant ΔICP4/ΔUL41/ΔICP22-modified HSV-1 genome comprising an expression cassette containing the coding sequence of a human CFTR polypeptide under the control of a heterologous promoter integrated at the UL41 locus (FIG. 1H); and 8) a recombinant ΔICP4/ΔUL41/ΔICP22-modified HSV-1 genome comprising an expression cassette containing the coding sequence of a human CFTR polypeptide under the control of a heterologous promoter integrated at the ICP22 locus (FIG. 1I)

These modified herpes simplex virus genome vectors are transfected into engineered cells that are modified to express one or more herpes virus genes. These engineered cells secrete into the supernatant of the cell culture a replication defective herpes simplex virus with the modified genomes packaged therein. The supernatant is then collected, concentrated, and sterile filtered through a 5 µm filter.

Example 2: Construction and In Vitro Characterization of an HSV-1 Vector Encoding Human CFTR in 2D Cultures Initial lung gene therapy clinical trials occurred in the early 1990s following the discovery of the genetic defect responsible for cystic fibrosis. Recombinant adenovirus was one of the early vectors tested for CFTR delivery; however, adeno-based vectors failed these trials mainly due to the paucity of viral receptors on the apical lung surface and the severity of the host-immune response to repeated viral delivery. The other viral gene therapy vectors administered to CF patients were based on adeno-associated virus (numerous AAV serotypes have been tested in the CF clinical setting). Large repeat administration studies of AAV-based gene therapy vectors provided disappointing results in improving CF lung function in dosed patients. Much like adenovirus, recombinant AAV vectors do not efficiently infect the apical lung surface, and due to physical limitations of the size of encoded cargo, AAV vectors do not efficiently delivery full length human CFTR. Despite more than two decades of intensive effort, viral-based gene therapies have yet to help patients with CF (or any other obstructive lung disease).

At present, according to the US Cystic Fibrosis Foundation, there are no ongoing clinical trials of viral gene therapies in CF, and only two virus-based gene therapy vectors are in preclinical development (both of which are based on AAV, a vector that, as noted above, has already failed multiple clinical trials in CF patients). Instead, focus has shifted away from virus-based vectors to non-viral methods of CFTR delivery (e.g., DNA plasmids or mRNAs complexed with liposomes). Unfortunately, these non-viral vectors have seen only limited success, due, at least in part, to the significant hurdles faced by product instability and/or inefficient delivery/transfection of liposomal formulations. All-in-all, over 25 clinical trials involving more than 470 patients testing viral and non-viral gene vectors have failed to show clinical benefit, largely due to inefficient gene transfer to target cells and host immune-mediated clearance after repeated exposure.

To this end, a recombinant herpes simplex virus type 1 (HSV-1) vector encoding full-length human CFTR (HSV-CFTR) was developed as a novel gene therapy for the treatment of CF patients. Without wishing to be bound by theory, it is believed that an HSV-based approach overcomes many of the hurdles experienced by other gene therapy vectors for CF, including the capacity to encode full-length human CFTR, the high efficiency of target cell transduction (HSV preferentially infects the apical membrane of polarized epithelial cells), the stability of the virus, and the established clinical safety of repeated administration of a product employing the same viral backbone as HSV-CFTR in the context of the highly inflammatory environment of wounded skin (ClinicalTrials.gov Identifier: NCT03536143). The following example describes experiments showing that this novel HSV-based gene therapy vector was capable of expressing functional, full-length human CFTR in cystic fibrosis patient-derived small airway epithelial cells (SAECs) in a dose-dependent manner.

Figure 2:
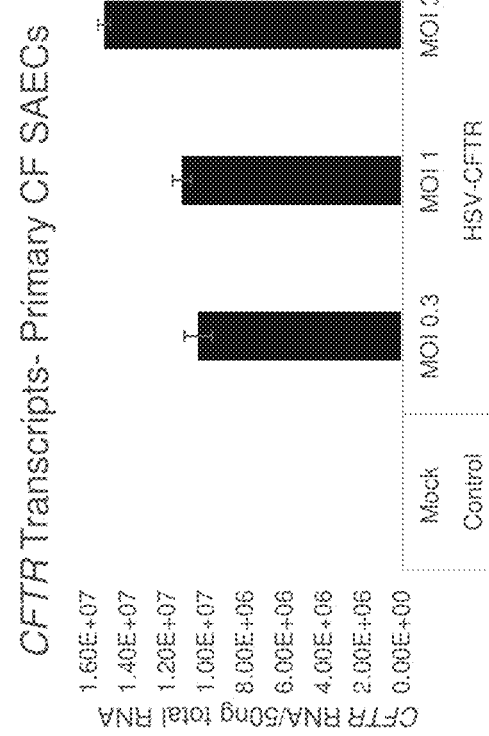
FIG. 2 shows expression of human CFTR in cystic fibrosis (CF) patient-derived primary small airway epithelial cells (SAECs) infected at the indicated multiplicities of infection (MOIs) with an HSV-CFTR vector, as assessed by qRT-PCR analysis. Mock infected CF SAECs were used as a negative control. Data is presented as the average of two replicates ±SEM.

HSV-CFTR was constructed as described in Example 1 above. Primary CF patient SAECs grown in 2D culture were left uninfected (mock) or were infected with HSV-CFTR at multiplicities of infection (MOIs) of 0.3, 1, or 3. Human CFTR expression was evaluated 48 hours post-infection in harvested cells by quantitative reverse transcription PCR (qRT-PCR). Codon-optimized CFTR transcripts were detected in infected primary CF SAECs at an MOI as low as 0.3, and appeared to show a dose-dependent increase in transgene expression up to an MOI of 3.0 (FIG. 2). Little-to-no exogenous CFTR RNA was observed in mock infected control samples, demonstrating specificity of the assay for the HSV-encoded human transgene.

Figure 3:
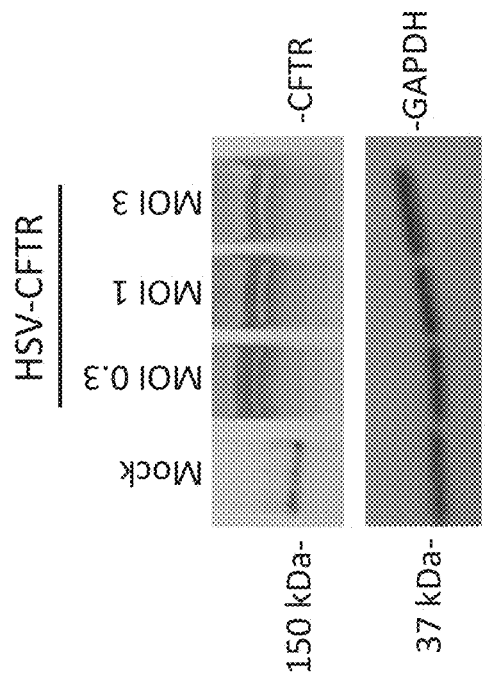
FIG. 3 shows expression of human CFTR protein in CF patient-derived primary SAECs infected at the indicated MOIs with an HSV-CFTR vector, as assessed by western blot analysis. Mock infected CF SAECs were used as a negative control. GAPDH was used as a loading control.

CFTR protein expression in HSV-CFTR-infected primary CF SAECs was assessed via western blot analysis. GAPDH was used as a control to ensure consistent loading of samples. CF patient SAECs overexpressed human CFTR when infected with HSV-CFTR, as compared to mock-infected control cells (FIG. 3). Interestingly, while the endogenous CFTR protein in mock infected cells resolved as a single band slightly larger than 150 kDa (the predicted size of full-length human CFTR is 168 kDa), the exogenous CFTR protein expressed in HSV-CFTR-transduced cells appeared as a doublet of significantly larger size. Human CFTR is known to exist in three different forms depending on glycosylation status: (1) nonglycosylated; (2) core glycosylated; and (3) complex glycosylated, fully mature (Scanlin, 2001, *Respir Res*, 2(5), pp. 276-9). The appearance of the single lower molecular weight band in mock infected CF patient cells suggested that the endogenous (mutant) protein solely exists in the nonglycosylated form, indicative of an immature protein variant that does not properly traffic through the endoplasmic reticulum (ER) to the cell surface. In stark contrast, the appearance of the two larger forms of CFTR in HSV-CFTR infected cells revealed extensive post-translation modification of the human transgene, likely representing the core glycosylated and complex glycosylated variants of CFTR, suggesting proper maturation and trafficking of the exogenous protein through the ER.

Figure 4B:
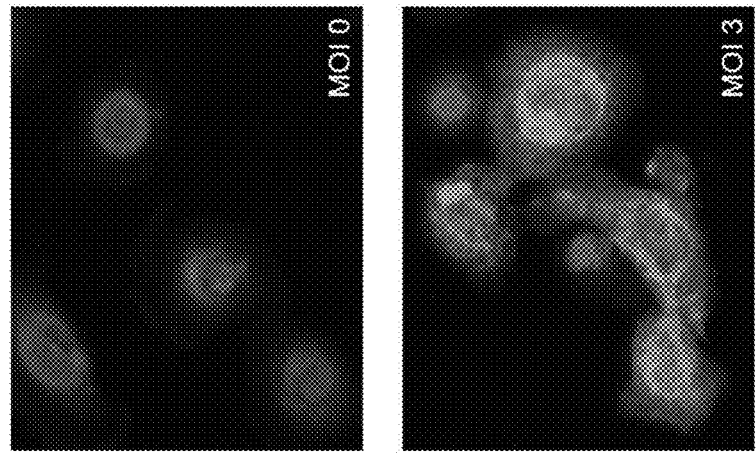
FIGS. 4A-4B show representative immunofluorescence images of human CFTR protein expression in mock infected or HSV-CFTR infected primary CF patient SAECs.
Figure 4A:
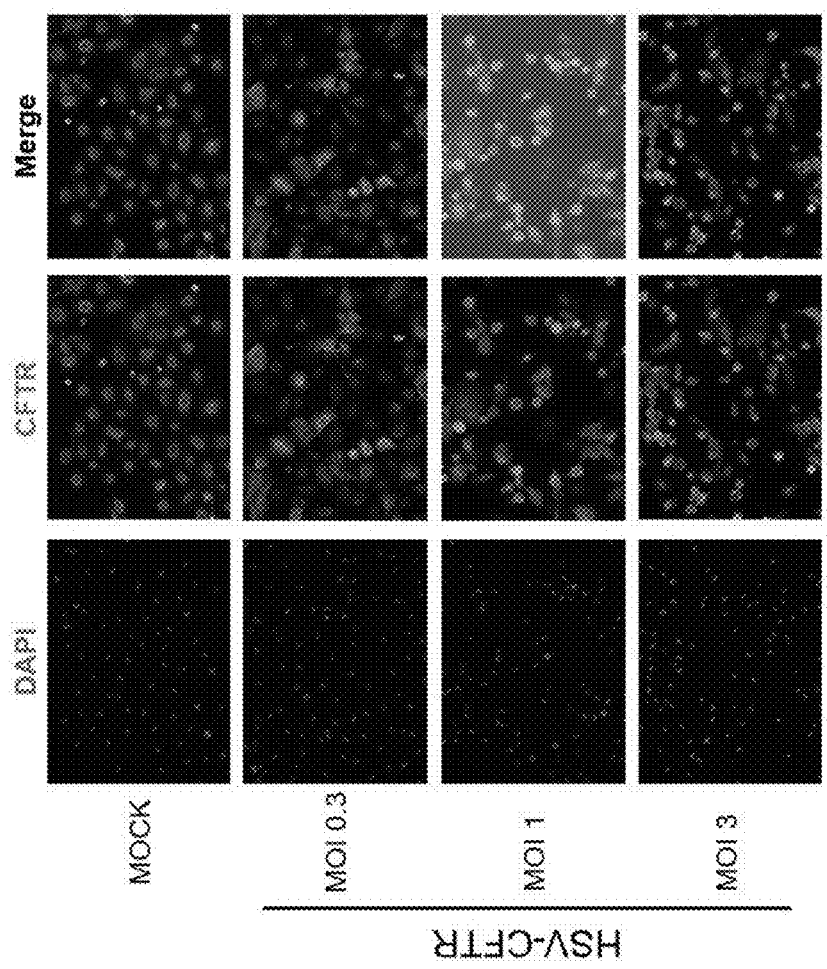

CFTR protein expression and relative localization was next examined by immunofluorescence. Primary CF patient SAECs were transduced with HSV-CFTR at the indicated MOIs for 48 hours, and immunofluorescence staining for human CFTR was performed. A mock infected control sample was added to show baseline levels and cellular localization of the endogenous mutant CFTR protein in these diseased cells. When analyzed in the context of the control cells, the immunofluorescence data demonstrated that transduced SAECs displayed an HSV-CFTR dose-dependent increase in CFTR protein expression (FIG. 4A). When comparing the relative cellular localization of CFTR expressed in mock-infected vs. HSV-CFTR-infected CF patient SAECs (FIG. 4B), the CFTR expressed in uninfected cells appeared to be relegated to the perinuclear region (suggestive of entrapment and turnover in the ER), while CFTR was found throughout the cytoplasm and at the cell surface of HSV-CFTR transduced cells (indicative of proper maturation in, and trafficking through, the ER). This data was in agreement with the western blot data that suggested that the wild-type, HSV-CFTR-expressed CFTR was fully glycosylated while the endogenous, mutant CFTR was non-glycosylated (FIG. 3).

Figure 5:
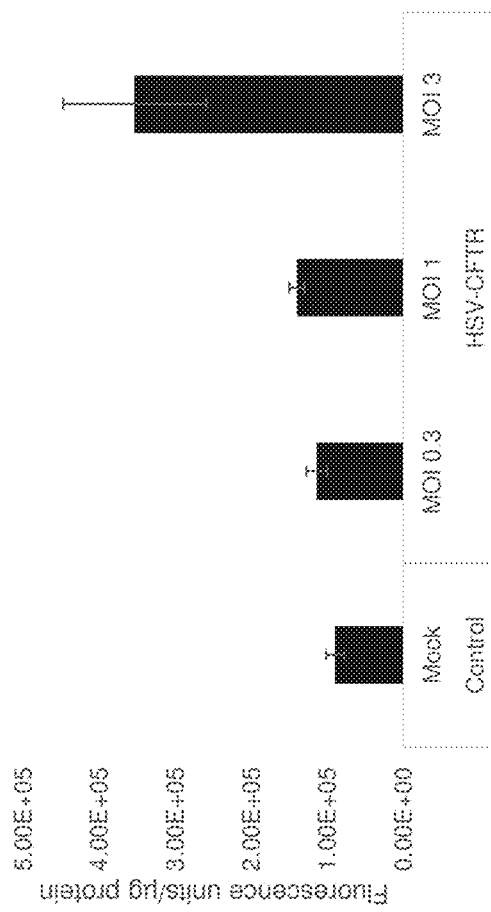
FIG. 5 shows human CFTR protein functionality in CF patient-derived primary SAECs infected at the indicated MOIs with an HSV-CFTR vector, as assessed by a fluorescent dye uptake assay. Mock infected CF SAECs were used as a negative control. Data is presented as the average±SEM.

Finally, functionality of the HSV-CFTR-expressed human CFTR in infected CF patient SAECs was confirmed using a dihydrorhodamine 6G (dR6G) fluorescent dye uptake assay which was previously validated as a functional endpoint for virus-mediated CFTR restoration in 2D CF patient epithelial cell culture (Wersto, 1996, *Proc Natl Acad Sci USA*, 93(3), pp. 1167-72). Briefly, HSV-CFTR or mock-infected primary CF patient SAECs were incubated with dR6G-containing cell culture medium for 15 minutes, washed four times with PBS, lysed in RIPA buffer, and 526 nm excitation/555 nm emission fluorescence was read for each sample on a plate reader. dR6G is itself non-fluorescent, but is converted to the fluorescent compound rhodamine 6G upon cellular uptake and exposure to intracellular dehydrogenases, a process that depends on the presence of functional CFTR (Wersto, 1996, *Proc Natl Acad Sci USA*, 93(3), pp. 1167-72). A BCA assay was performed on each cell lysate to quantify total protein content, and relative fluorescence per µg total protein was calculated for each sample (FIG. 5). HSV-CFTR infection of primary CF patient SAECs caused a modest, dose-dependent increase in dR6G uptake as compared to mock infected controls, indicating that HSV-CFTR was capable of restoring CFTR function in these diseased primary epithelial cells.

Example 3: In Vitro HSV-CFTR Dose-Ranging and Pharmacology in 3D Organotypic Cultures Using CF Patient-Derived Organoids Mutations in the CFTR gene are classified into one of six classes by the primary mechanism leading to CFTR malfunction. Mutations affecting synthesis and processing result in more severe disease because little-to-no protein reaches the cell surface; mutations that do not interfere with luminal trafficking but reduce CFTR-mediated anion efflux often lead to less severe symptoms due to the retention of some residual CFTR function at the apical membrane (Foundation, 2019, 2018 *Annual Data Report*, Bethesda: Cystic Fibrosis Foundation). Because CFTR mutations affect distinctive stages of protein synthesis and function, recent drug development efforts have focused on small molecule modulator therapies targeting a specific source of the protein's defect. For example, ivacaftor, subclassified as a CFTR protein "potentiator", augments chloride secretion of membranal CFTR (providing clinical benefit for persons with specific class III and IV CFTR gating and conductance mutations), while elexacaftor, subclassified as a CFTR protein "corrector", acts by facilitating the proper folding and cellular processing of CFTR that would otherwise be degraded by the endoplasmic reticulum's quality control pathway (providing clinical benefit for persons with specific class II CFTR trafficking mutations) (Clancy, 2019, *Am J Respir Crit Care Med*, 186(7), pp. 593-7). While recent FDA approval of four of these modulator therapies has been a boon to CF patients harboring the specific mutations responsive to these drugs, these modulators only treat a subset of the CF population. In particular need for effective drug intervention are patients harboring class I mutations (responsible for ~10% of CF cases worldwide), encompassing frameshift, splicing, and nonsense mutations that result in severely reduced or absent CFTR expression, as these patients suffer from the harshest and deadliest forms of CF (Wilschanski, 2012, *Front Pharmacol*, 20(3), pp. 1-3).

Due to a lack of adequate CF animal models, efficacy studies in air-liquid-interface-differentiated bronchial epithelial cells derived from CF patient lung explant materials have been used for some drug development efforts following proof-of-concept experimentation in heterologous 2D cell systems (Neuberger, 2011, *Methods Mol Biol*, 741(1), pp. 39-54) (Randell, 2011, *Methods Mol Biol*, 742(1), pp. 285-310). However, the limited availability of lung explant tissues and the invasive procedures necessary to obtain bronchial cells from CF patients without end-stage disease has led to development of 3D organotypic systems derived from "easy access" tissues harvested from CFTR mutant patients, for testing novel therapeutics to treat CF. One such technology, using a forskolin-induced swelling (FIS) assay, employs CF patient-derived intestinal organoids (PDOs) to study CFTR protein function alone or in response to pharmaceutical intervention (Dekkers, 2013, *Nat Med*, 19(7), pp. 939-45), and has proven to be a breakthrough in CF drug development. When exposed to forskolin, organoids rapidly increase their cyclic AMP content, which in turn results in the opening of the CFTR channel. Organoids derived from biopsies taken from healthy individuals swell as a consequence of ion and water transport into the organoid lumen mediated by CFTR, while organoids derived from CFTR mutant patient biopsies (or wild-type organoids exposed to specific pharmacological inhibition of CFTR protein function) have reduced or completely inhibited swelling capacity (Boj, 2017, *J Vis Exp*, 120(1), p. e55159). Use of CF PDOs allows for the quantitative measure of CFTR protein function (via detection of organoid swelling) upon treatment with novel therapeutics, and positive results from this 3D organotypic system have been shown to directly correlate with clinical benefit, including both changes in pulmonary responses and sweat chloride concentration in treated CF patients (Berkers, 2019, *Cell Rep*, 26(7), pp. 1701-1708).

The following example describes experiments showing that the recombinant HSV-1 vector HSV-CFTR, characterized in Example 2 above, was capable of rescuing the cystic phenotype of CF PDOs, irrespective of the underlying CFTR mutation.

HSV-CFTR's ability to restore functional CFTR expression was tested in clinically relevant 3D organotypic cultures using intestinal organoids derived from four different CF patients; (1) a female patient homozygous for an F508del CFTR mutation (class II mutation), (2) a male patient also homozygous for the F508del mutation, (3) a female patient homozygous for a G542X nonsense CFTR mutation (class I mutation), and (4) a female patient homozygous for a W1282X nonsense CFTR mutation (class I mutation). To assess CFTR activity in transduced organoids, organoid morphology and size were assessed 24- or 48-hours post-infection, and a FIS assay was conducted as described previously (Boj, 2017, *J Vis Exp*, 120(1), p. e55159). For efficient infection of the CF organoids, the organoids were sheared into small fragments, incubated in solution with HSV-CFTR at the indicated MOIs for 1 hour, and seeded in 96-well clear bottom plates for analysis. The FIS assay was conducted 24- or 48-hours after seeding, as described in more detail below.

Figure 6A:
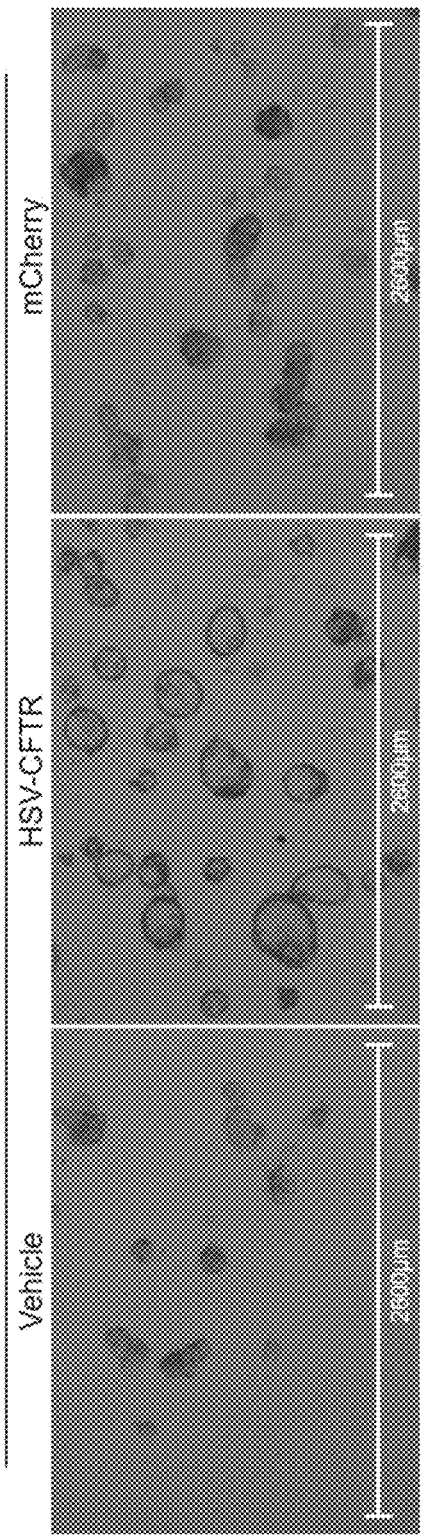
Figure 6A:
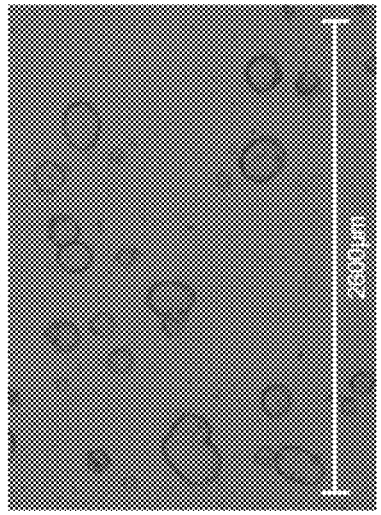
Figure 6C:
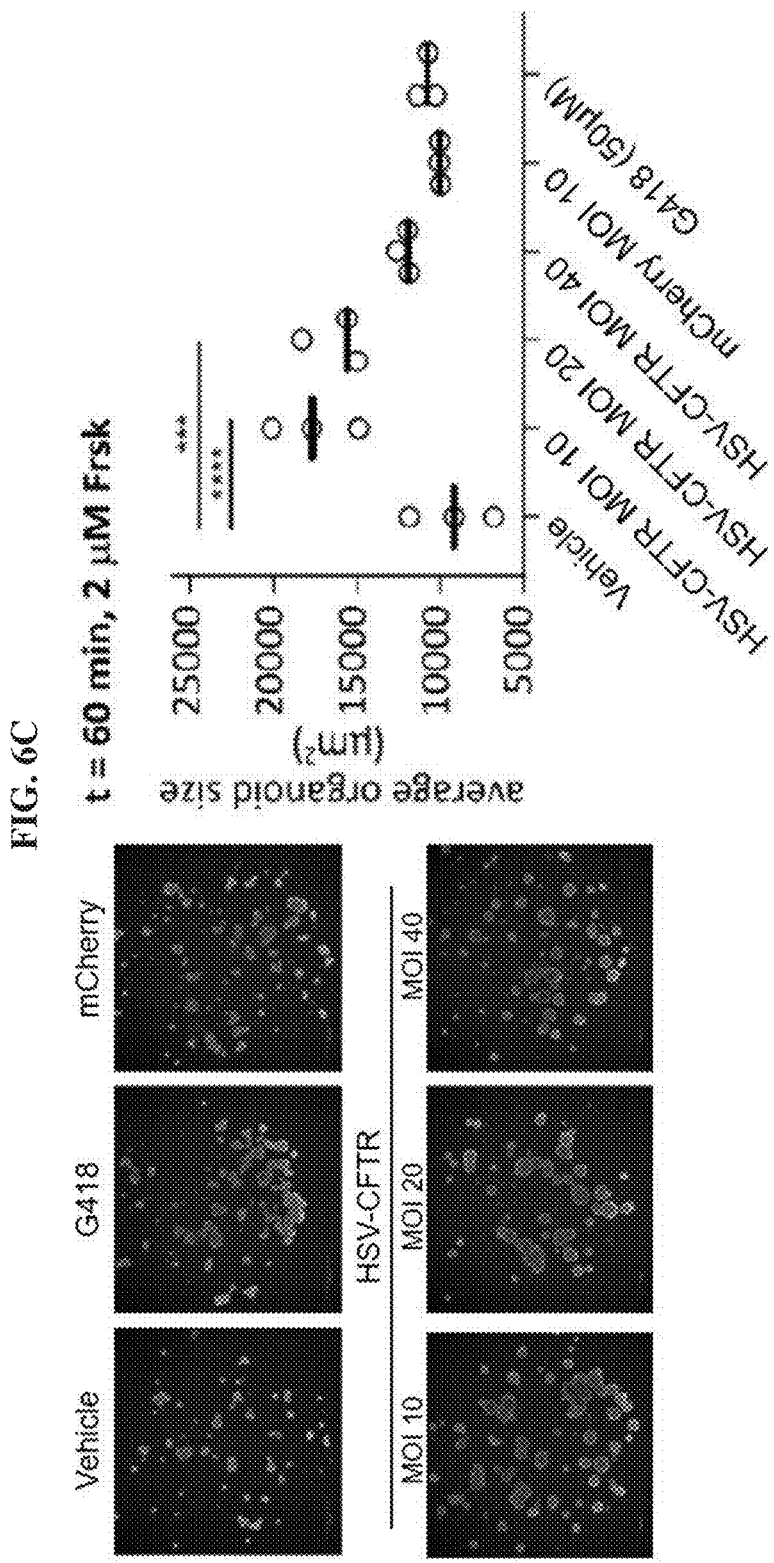

First, the G542X/G542X PDO was infected at MOIs of 10, 20, and 40 to evaluate both the vector's impact on organoid swelling and cell viability. Intestinal organoids derived from a healthy patient were plated in parallel as a comparator. Surprisingly, HSV-CFTR-transduced organoids showed lumen formation and a clear cystic morphology mimicking wild-type PDOs 24 hours post-infection, suggesting full functional correction of the diseased phenotype by the engineered vector prior to the addition of forskolin (FIG. 6A). An mCherry-expressing HSV vector was used as a negative control to show that the alterations in PDO morphology observed in the HSV-CFTR treated samples were not due to a non-specific response to viral infection. Next, a FIS assay was performed 48 hours after infection. At t=0, before the addition of forskolin and subsequent activation of CFTR, HSV-CFTR-transduced organoids already possessed a significantly enlarged lumen area, as compared to vehicle-treated or mCherry-infected organoids, in agreement with the observations at 24 hours post-infection (FIG. 6B). Interestingly, only a moderate increase in organoid swelling was observed 60 minutes after the addition of forskolin (t=60) in HSV-CFTR transduced organoids, likely due to these organoids already being close to their maximum swelling potential prior to forskolin exposure (FIG. 6C). The G542X/G542X mutation can be (at least partially) corrected by exposure to the aminoglycoside geneticin (G418) that allows for translational readthrough of the nonsense mutation, and G418 was included in this assay as a positive control. While the G542X/G542X PDOs swelled in the presence of G418 at t=60, the average organoid size in these positive control samples were significantly smaller than those of HSV-CFTR-exposed PDOs (FIGS. 6B and 6C). Slight-to-moderate toxicity of the vector in the G542X/G542X PDOs was observed 48 hours after infection when HSV-CFTR was used at an MOI of 20 or 40, and toxicity at an MOI≥20 is likely causative of the diminished capacity for swelling observed in these organoids, as compared to the samples infected at an MOI of 10. However, even though a cytotoxic effect at high MOIs was observed, the treated organoids still outperformed the positive small molecule control.

Figure 7A:
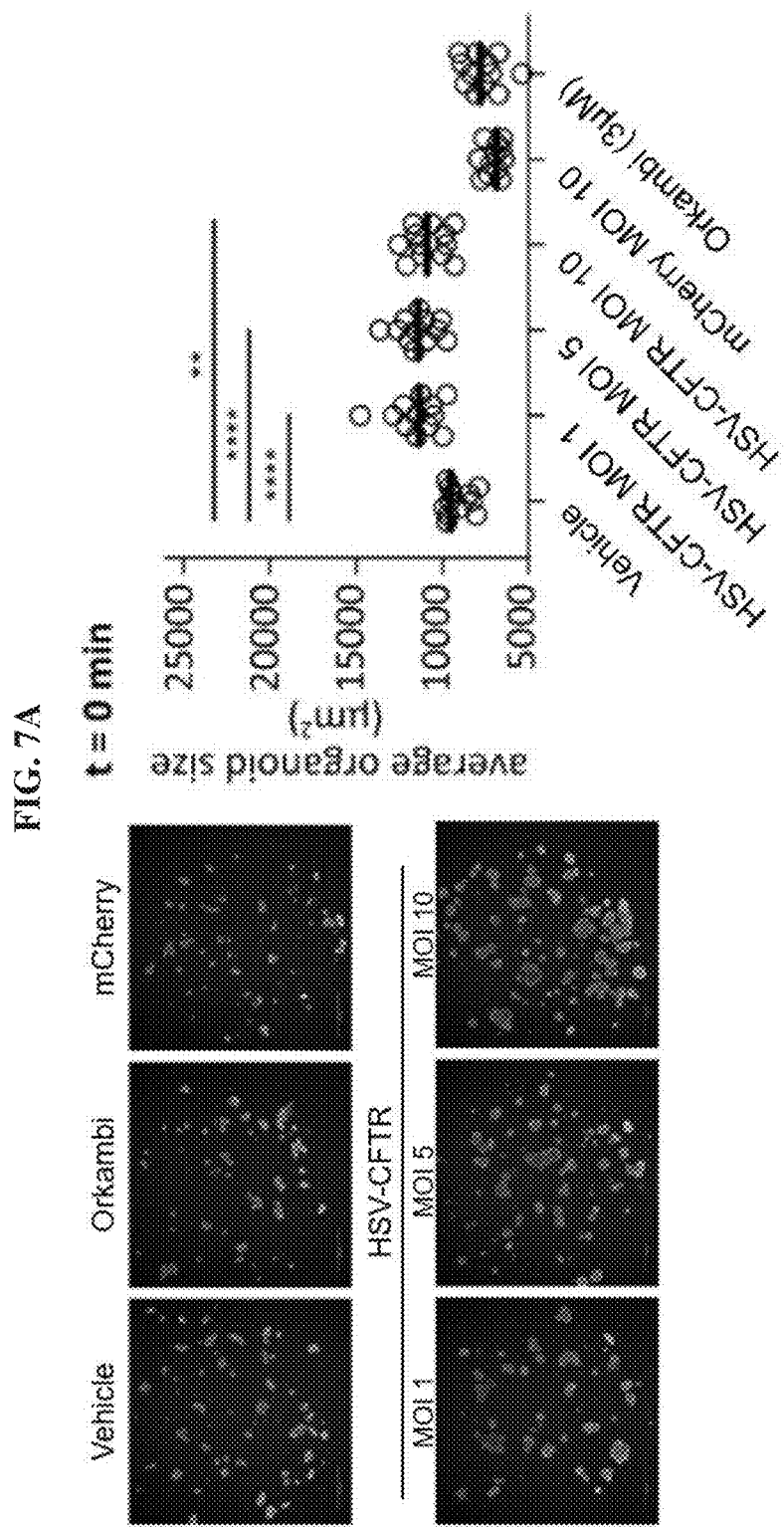
FIGS. 7A-7B show analyses of F508del/F508del cystic fibrosis patient-derived intestinal organoids (PDOs) infected with HSV-CFTR at the indicated MOIs. Vehicle alone or an mCherry-encoding HSV vector (mCherry) were used as negative controls; Orkambi® was used as a positive control.
Figure 7B:
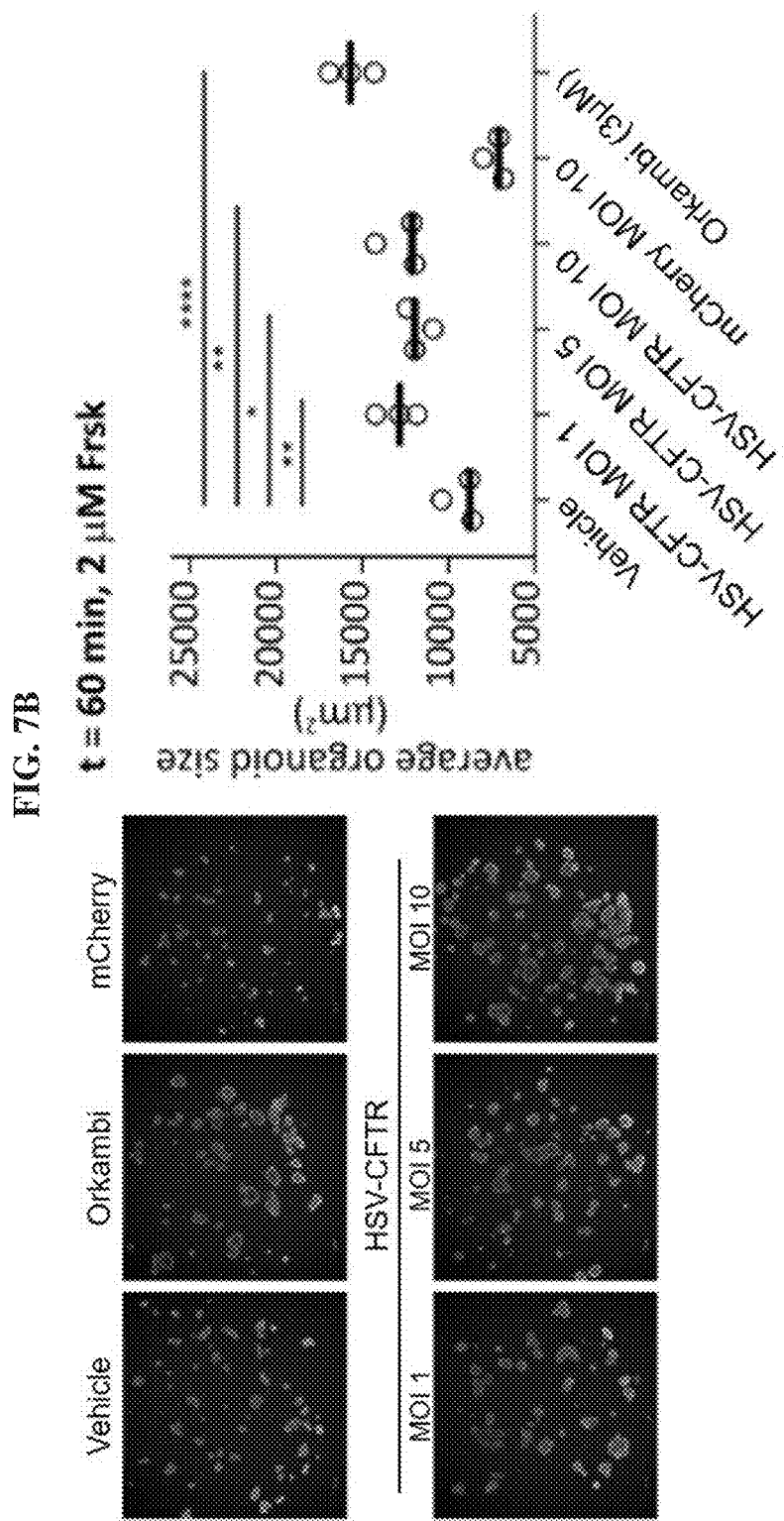

Because HSV-CFTR corrected diseased organoids to the wild-type morphology (large cystic lumen) at all tested MOIs within 24 hours, and the higher HSV-CFTR doses appeared to negatively impact the organoids in the swelling assays, the three remaining cystic fibrosis PDOs were tested at lower HSV-CFTR doses (MOIs of 1, 5, and 10) and were analyzed via FIS assay 24 hours post-infection. First, HSV-CFTR was tested in PDOs derived from a patient that is homozygous for the F508del mutation of CFTR. F508del is the most common mutation in cystic fibrosis patients; at least one copy of this allele is found in approximately 85% of CF patients worldwide, and F508del accounts for about 70% of CFTR loss-of-function mutations (Maiuri, 2015, *Ann Transl Med*, 3(Supple 1), p. S24). The majority of the tested F508del organoid cultures showed a cystic (wild-type) morphology 24 hours after infection with HSV-CFTR, even at the lowest dose tested (MOI of 1). The average size of F508del organoids treated with HSV-CFTR was significantly increased compared to vehicle control or mCherry-infected organoids prior to forskolin addition (FIG. 7A). No significant change in average organoid size was detected after forskolin addition in HSV-CFTR-transduced samples, as these organoids are believed to already be at or near their maximal swelling capacity, i.e., "pre-swollen" (FIG. 7B). Importantly, functional correction of the CFTR defect in F508del organoids was found to be similar between the HSV-CFTR-treated organoids prior to forskolin treatment and the positive control Orkambi®-exposed organoids 60 minutes after forskolin treatment (FIG. 7A vs. FIG. 7B). Orkambi® is a combination therapy of lumacaftor/ivacaftor that is FDA-approved for the treatment of CF patients aged 2 years and older who are homozygous for the F508del mutation. No apparent cytotoxicity attributable to the vector was observed at any of the MOIs tested.

Figure 8A:
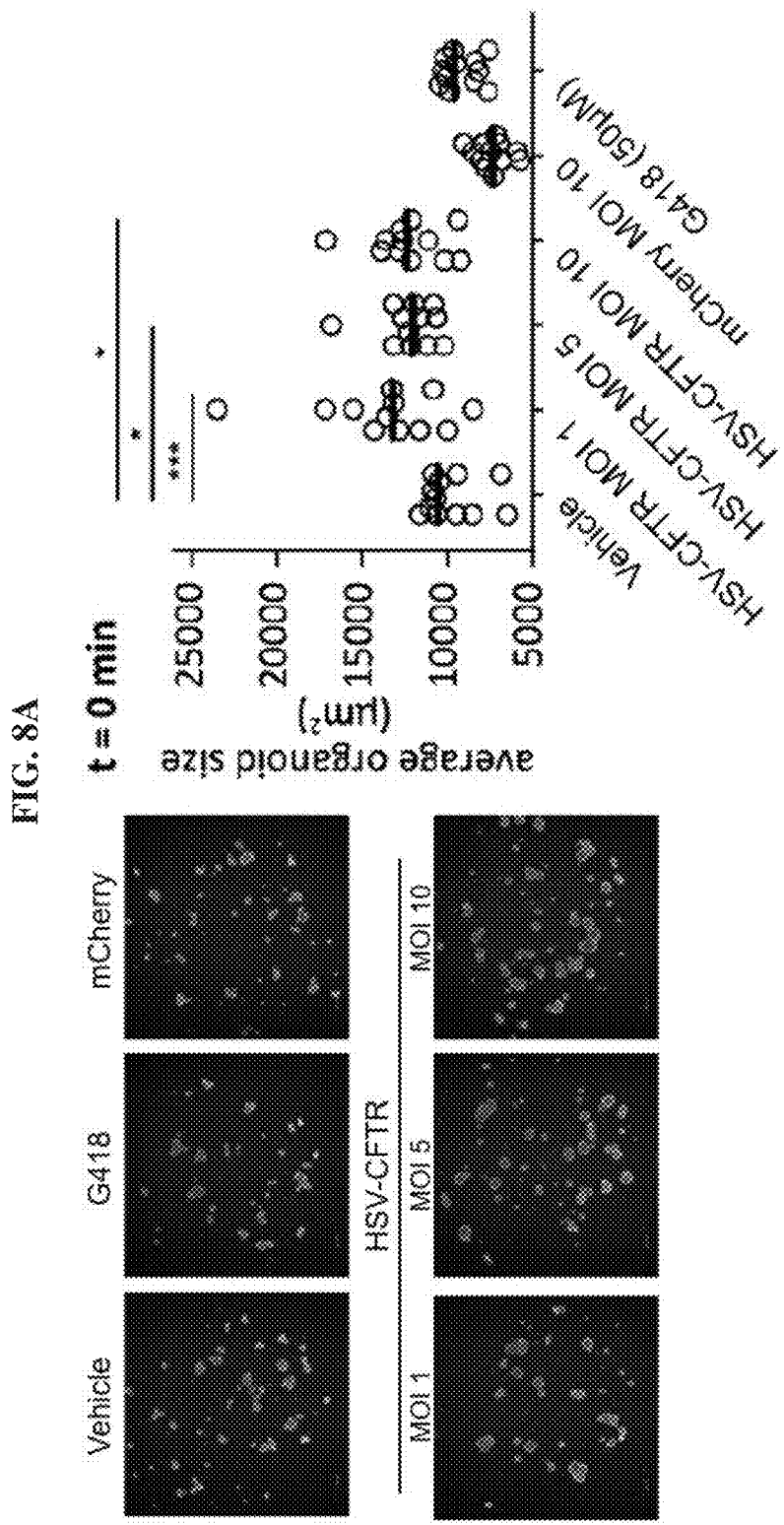
FIGS. 8A-8B show analyses of W1282X/W1282X cystic fibrosis patient-derived intestinal organoids (PDOs) infected with HSV-CFTR at the indicated MOIs. Vehicle alone or an mCherry-encoding HSV vector (mCherry) were used as negative controls.
Figure 8B:
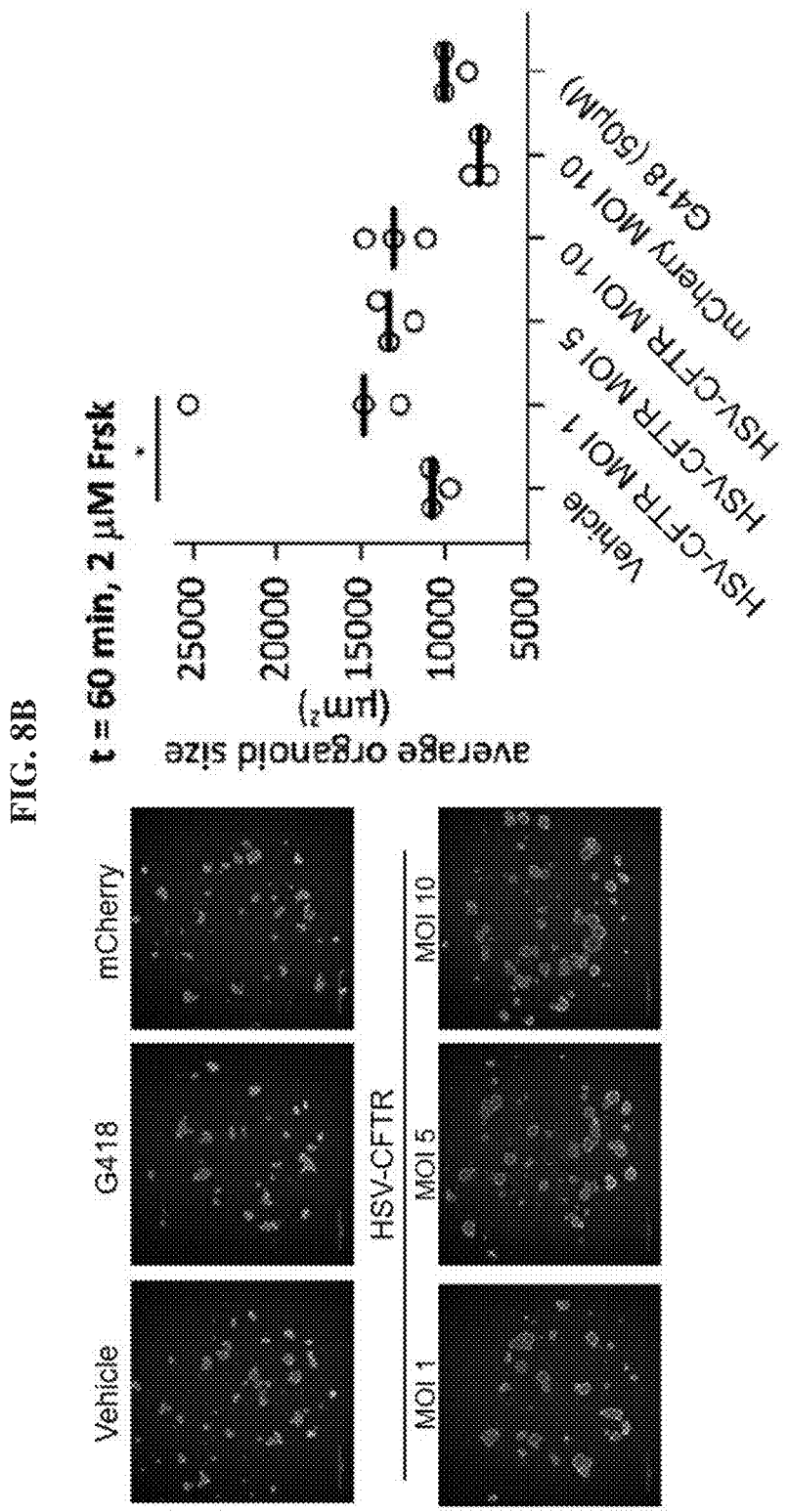

Next, organoids derived from a patient homozygous for a second nonsense CFTR mutation (W1282X) were infected with HSV-CFTR, and organoid size was quantified before and after forskolin addition. In agreement with the data presented in FIG. 6 above, HSV-CFTR efficiently restored the wild-type cystic phenotype and increased the average organoid size 24 hours post-infection in the W1282X/W1282X nonsense CFTR PDOs prior to forskolin addition (FIG. 8A). Again, HSV-CFTR at an MOI as low as 1 appeared to correct the diseased morphology both before and after forskolin addition (FIGS. 8A and 8B). G418 was also included in these experiments; however, the W1282X/W1282X PDOs were found not to respond to this readthrough aminoglycoside, so no positive control could be included in this experiment (as no effective therapy currently exists for all nonsense CFTR mutations). This data suggested that HSV-CFTR could restore CFTR function in both G418-responsive and G418-non-responsive CFTR null patient samples.

Figure 9A:
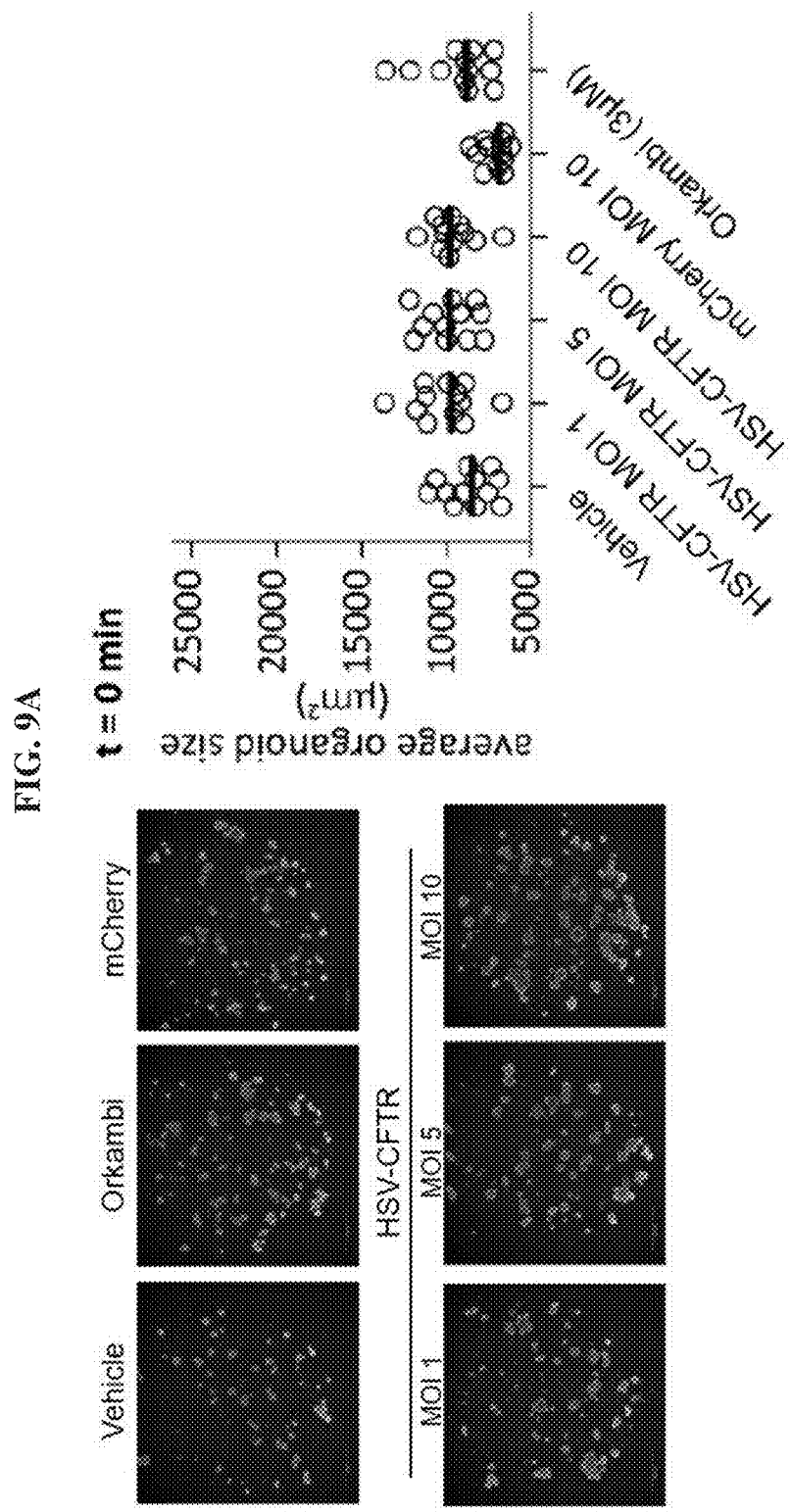
FIGS. 9A-9B show analyses of F508del/F508del cystic fibrosis patient-derived intestinal organoids (PDOs) infected with HSV-CFTR at the indicated MOIs. Vehicle alone or an mCherry-encoding HSV vector (mCherry) were used as negative controls; Orkambi® was used as a positive control.
Figure 9B:
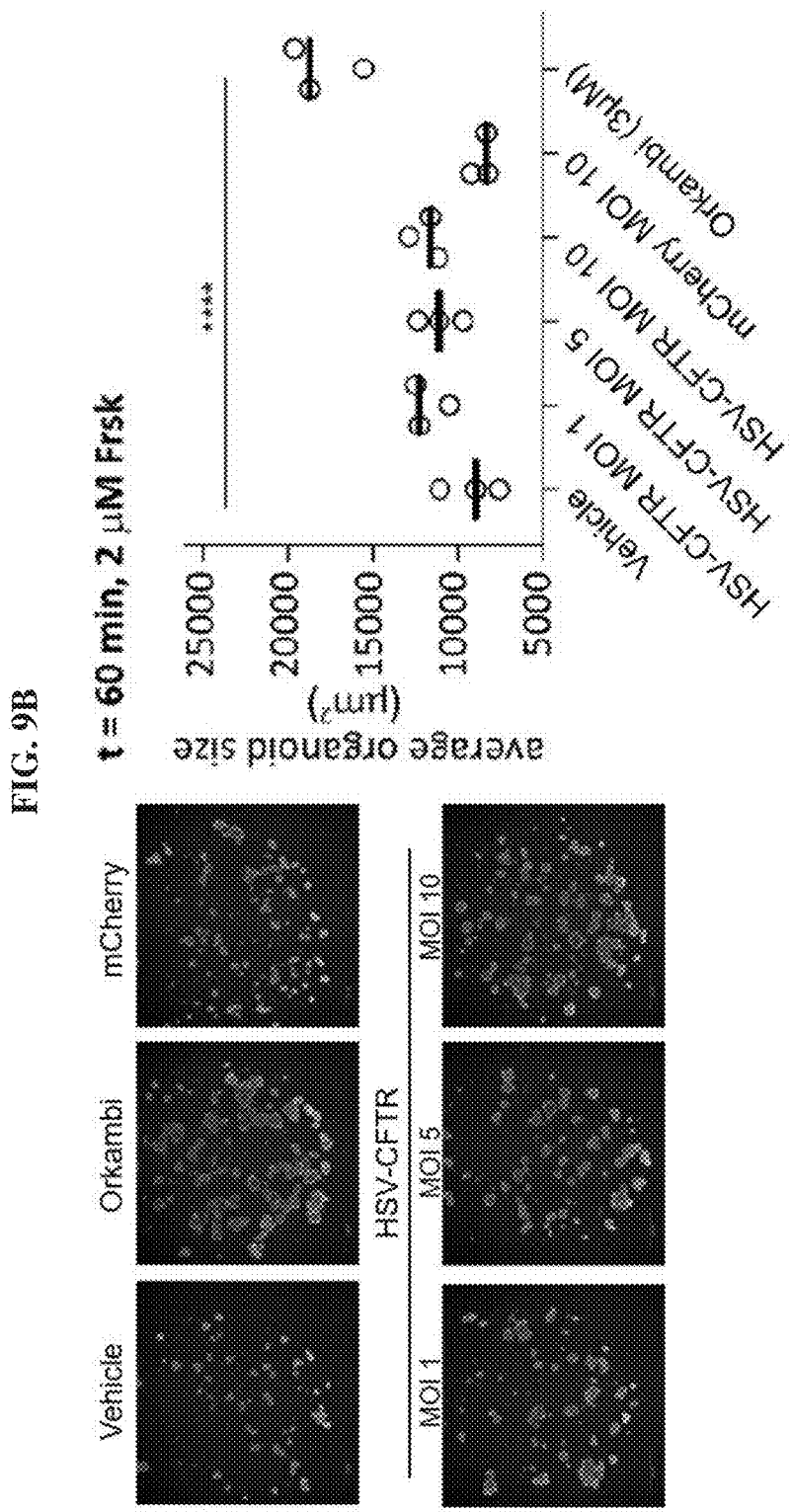

Finally, organoids from a second F508del homozygous patient were tested. PDOs infected with HSV-CFTR had a slightly increased average size compared to vehicle-treated organoids, but this difference was not statistically significant (FIGS. 9A and 9B).

The data from these studies revealed that transduction of intestinal CF organoids with HSV-CFTR resulted in a striking alteration of organoid morphology, from a compact budding CF phenotype to a cystic organoid phenotype containing a well-defined lumen exhibiting wild-type characteristics, within 24 hours of infection at MOIs ranging from 1 to 40. This "pre-swollen" wild-type phenotype was quantitatively demonstrated by measuring total organoid size, before the addition of forskolin and resulting activation of CFTR, in comparison to multiple negative controls. Due to the "pre-swollen" nature of HSV-CFTR-transduced organoids, the capacity for forskolin to stimulate further swelling was limited. The observation of a corrected cystic morphology in CF organoids exposed to low doses of HSV-CFTR suggested that high levels of exogenous wild-type CFTR expressed in a minority of cells was sufficient to establish disease correction, indicating a "dominant" effect of this therapeutic modality. One F508del organoid showed slightly less efficient restoration of the wild-type phenotype as compared to the other examined CF organoid cultures; however, a cystic morphology was observed in all CF organoids infected with HSV-CFTR at an MOI of 5 or higher. The differences observed between the various CF intestinal organoid cultures were most likely due to slight alterations of their proliferative or differentiation status at the time of infection, and thus, it is unlikely that the CFTR genotype itself contributed meaningfully to the efficiency of HSV-CFTR transduction or functional CFTR expression. Put another away, HSV-CFTR corrected the CF diseased phenotype irrespective of the underlying CFTR mutation in this clinically translatable 3D organotypic system.

Taken together, the data provided in these Examples indicate that HSV-CFTR capably infected relevant airway epithelia, efficiently produced functional human CFTR, and molecularly corrected multiple CFTR defects without significant toxicity. Without wishing to be bound by theory, it is believed that these studies represent the first instance of experimental validation of an attenuated HSV-based gene therapy vector for delivering full-length functional human CFTR, supporting the application of HSV-CFTR as a novel, broadly applicable gene therapy for the treatment of CF.

Example 4: Proof-of-Concept In Vivo Administration of an Inhaled HSV-Based Vector The following example describes a proof-of-concept in vivo study examining the feasibility of administering an HSV-based vector to the trachea and/or lungs of immunocompetent animals after intranasal or intratracheal administration of the virus.

All procedures conducted in this example were in compliance with applicable animal welfare acts and were approved by the local Institutional Animal Care and Use Committee (IACUC). 10 five- to six-week old C57BL/6 mice were used in the study, five of which received either HSV-mCherry (described above) or vehicle control by intratracheal administration, and five of which received HSV-mCherry or vehicle control by intranasal administration. Prior to experimental procedures, the animals were sedated with an intraperitoneal injection of a mix of telazol/dexdomitor, and ophthalmic ointment was applied to the eyes to prevent drying of the corneas.

For intratracheal administration, the neck of each mouse was shaved using an electric razor, and depilatory cream was applied to remove all remaining fur. The surgical area was then cleaned twice with 70% ethanol-soaked swabs, and the anesthetized mice were positioned onto an angled restraint stand. A small incision in the neck was performed using surgical scissors, and the thymus, platysma, and anterior tracheal muscles were moved out of the way in order to visualize and access the tracheal rings. A 25 µL intratracheal injection of $4.9375 \times 10^8$ plaque forming units (PFUs) of HSV-mCherry was administered to three animals, while a 25 µL intratracheal injection of vehicle control was administered to two animals, and each mouse was held in a hanging position until its breathing gradually returned to normal. The incision site was closed with simple stitches, individually knotted.

For intranasal administration, mice were anesthetized as described above, and were position onto an angled restraining stand. Three mice were each inoculated intranasally with $4.9375 \times 10^8$ PFUs of virus formulated in 25 µL (12.5 µL per nostril). The rate of formulation release was adjusted to allow the mouse to inhale the inoculum, without forming bubbles, during the inspiration phase of breathing. Two mice were administered 25 µL of vehicle control using the same procedure. After administration, animals were held in a hanging position until breathing returned to normal.

All animals were allowed to recover from anesthesia, and were provided with water and food ad libitum until the time of sacrifice. 48 hours post-administration, mice were euthanized, and bronchoalveolar lavage (BAL) was performed in the left and right lungs using sterile saline. BAL fluid was collected, centrifuged, and the cell pellets were gathered. Next, the upper portions of the trachea were harvested and flash frozen in liquid nitrogen for nucleic acid quantification. The lungs (left lobe, right superior lobe, right middle lobe, and right inferior and post-caval lobes) were individually harvested and either flash frozen in liquid nitrogen for nucleic acid analysis or perfused in 4% neutral buffered formalin and embedded in paraffin for immunofluorescence analysis.

For immunofluorescence staining of paraffin embedded lung tissue, an Alexa Fluor® 488-conjugated pan cytokeratin antibody was used to detect epithelial cells (Invitrogen cat. no. 53-9003-82), and a rabbit anti-mCherry primary antibody (Abcam cat. no. ab213511) and Alexa Fluor® 594-conjugated secondary antibody (Abcam cat. no. ab150080) were used to detect infected cells. Tissue samples were mounted in mounting media containing DAPI to visualize nuclei.

Intranasal vs. intratracheal administration of HSV-mCherry resulted in similar levels of mCherry transcripts being detected in lung tissue of transduced animals (FIG. 10A). Interestingly, while little-to-no transgene transcripts were identified in the tracheas of intranasally-exposed mice, robust mCherry transcription was detected in the tracheas of intratracheally-exposed mice, with no statistically significant difference in transgene expression being observed between the lungs and tracheas of these invasively-treated animals. In addition, a greater average total cell count per mL of BAL fluid was observed in the intratracheally-administered animals (646,667 cells/mL and 393,333 cells/mL for intratracheal and intranasal administration, respectively), suggesting a greater influx of inflammatory cells into the lungs after intratracheal administration of the HSV-based vector. Transgene protein expression in lung epithelial tissue was observed in both intranasally- (FIG. 10B) and intratracheally-exposed (FIG. 10C) animals dosed with HSV-mCherry, but not in the corresponding vehicle controls.

Taken together, this data indicates that an engineered HSV vector can be administered to the lungs of immunocompetent animals via multiple routes of administration, and further, that a non-invasive inhaled route of administration allows for similar levels of transgene expression in the lungs as a more direct, invasive route of administration, while concomitantly inducing less (inflammatory) cell invasion.

Example 5: Nebulization of HSV-CFTR

The following example describes a study examining a non-invasive, nebulizer-based route of delivery for HSV-CFTR into the airways of wild-type and CFTR-deficient immunocompetent mice.

16 mice are used in the study: 12 immunocompetent C57BL/6 animals and 4 immunocompetent gut-corrected CFTR-deficient animals. Table 1 provides a summary of the study. 4 wild-type animals are administered HSV-CFTR via intranasal instillation, while the remaining animals are administered HSV-CFTR (or vehicle control) via nebulization (e.g., employing a vibrating mesh nebulizer). 48 hours after dosing, animals are euthanized, BAL fluid is collected, and tissue samples along the respiratory tract and lungs are harvested, i.e., the upper and lower trachea, the left and right bronchi, the left lung, and the right lung (superior, middle, inferior, and post-caval lobes, individually). Tissues from two animals/group are snap frozen in liquid nitrogen and a processed for nucleic acid analysis. Vector genomes/50 ng total DNA are quantified in each tissue via qPCR analysis; human CFTR transcripts/50 ng total RNA are quantified in each tissue via qRT-PCR analysis. Tissues from the remaining two animals/group are perfused and embedded in paraffin for immunofluorescence/immunohistochemistry. BAL fluid is processed to examine immune cell infiltration into the lungs.

TABLE 1

Study Design

| Group | Treatment | Route | n | Animals | Necropsy |
|---|---|---|---|---|---|
| 1 | Vehicle | Inhalation | 4 | C57BL/6 | 48 hours |
| 2 | HSV-CFTR | Intranasal instillation | 4 | C57BL/6 | |
| 3 | HSV-CFTR | Inhalation | 4 | C57BL/6 | |
| 4 | HSV-CFTR | Inhalation | 4 | $CFTR^{m1Unc}Tg(FABPCFTR)$ | |

What is claimed is:

1. A method of providing prophylactic, palliative, or therapeutic relief of one or more signs or symptoms of cystic fibrosis in a subject in need thereof, the method comprising administering to the subject an effective amount of a pharmaceutical composition comprising:
   (a) a herpes virus comprising a recombinant herpes virus genome, wherein the recombinant herpes virus genome comprises one or more polynucleotides encoding a CFTR polypeptide; and
   (b) a pharmaceutically acceptable excipient,
   wherein the one or more polynucleotides encoding a CFTR polypeptide are operably linked to a promoter,
   wherein the one or more polynucleotides encoding a CFTR polypeptide are expressed from the recombinant herpes virus genome to effect a measurable improvement in or prevention of the one or more signs or symptoms of cystic fibrosis, and
   wherein the pharmaceutical composition is administered to the subject using a nebulizer.

2. The method of claim 1, wherein the subject is a human.

3. The method of claim 1, wherein the nebulizer is a vibrating mesh nebulizer.

4. The method of claim 1, wherein the herpes virus comprising the recombinant herpes virus genome is replication competent.

5. The method of claim 1, wherein the herpes virus comprising the recombinant herpes virus genome is replication defective.

6. The method of claim 1, wherein the recombinant herpes virus genome is selected from the group consisting of a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any derivatives thereof.

7. The method of claim 6, wherein the recombinant herpes simplex virus genome is a recombinant HSV-1 genome.

8. The method of claim 7, wherein the recombinant HSV-1 genome has been engineered to reduce or eliminate expression of one or more toxic herpes simplex virus genes.

9. The method of claim 7, wherein the recombinant HSV-1 genome comprises an inactivating mutation in a herpes simplex virus gene selected from the group consisting of ICP0, ICP4, ICP22, ICP27, ICP47, tk, UL41, and UL55.

10. The method of claim 1, wherein the CFTR polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 5 or SEQ ID NO: 6.

11. A method of reducing or inhibiting progressive lung destruction in a subject in need thereof, the method comprising administering to the subject an effective amount of a pharmaceutical composition comprising:
(a) a herpes virus comprising a recombinant herpes virus genome, wherein the recombinant herpes virus genome comprises one or more polynucleotides encoding a CFTR polypeptide; and
(b) a pharmaceutically acceptable excipient, wherein the one or more polynucleotides encoding a CFTR polypeptide are operably linked to a promoter,
wherein the one or more polynucleotides encoding a CFTR polypeptide are expressed from the recombinant herpes virus genome to reduce or inhibit the progressive lung destruction, and
wherein the pharmaceutical composition is administered to the subject using a nebulizer.

12. The method of claim 11, wherein the subject suffers from a chronic lung disease.

13. The method of claim 12, wherein the chronic lung disease is cystic fibrosis or chronic obstructive pulmonary disease (COPD).

14. The method of claim 11, wherein the subject is a human.

15. The method of claim 11, wherein the nebulizer is a vibrating mesh nebulizer.

16. The method of claim 11, wherein the recombinant herpes virus genome is selected from the group consisting of a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any derivatives thereof.

17. The method of claim 16, wherein the recombinant herpes simplex virus genome is a recombinant HSV-1 genome.

18. The method of claim 11, wherein the CFTR polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 5 or SEQ ID NO: 6.

* * * * *